United States Patent [19]

Studnicka et al.

[11] Patent Number: 5,766,886
[45] Date of Patent: Jun. 16, 1998

[54] MODIFIED ANTIBODY VARIABLE DOMAINS

[75] Inventors: Gary M. Studnicka, Santa Monica; Roger G. Little, II, Benicia; Dianne M. Fishwild, Hayward; Fred R. Kohn, Walnut Creek, all of Calif.

[73] Assignee: Xoma Corporation, Berkeley, Calif.

[21] Appl. No.: 107,669

[22] PCT Filed: Dec. 14, 1992

[86] PCT No.: PCT/US92/10906

§ 371 Date: Aug. 13, 1993

§ 102(e) Date: Aug. 13, 1993

[87] PCT Pub. No.: WO93/11794

PCT Pub. Date: Jun. 24, 1993

Related U.S. Application Data

[63] Continuation-in-part of Ser. No. 808,464, Dec. 13, 1991, abandoned.

[51] Int. Cl.⁶ .......................... C12P 21/04; C12N 15/00; C07K 16/00; A61K 39/395
[52] U.S. Cl. ............... 435/70.21; 435/69.1; 435/172.1; 435/172.3; 424/133.1; 530/387.3; 536/23.53
[58] Field of Search ................ 530/387.3; 424/133.1; 435/69.1

[56] References Cited

U.S. PATENT DOCUMENTS

| | | |
|---|---|---|
| 4,391,904 | 7/1983 | Litman et al. |
| 4,816,397 | 3/1989 | Boss et al. |
| 4,816,567 | 3/1989 | Cabilly et al. |
| 4,853,871 | 8/1989 | Pantoliano et al. |
| 4,888,415 | 12/1989 | Lambert et al. |
| 4,925,673 | 5/1990 | Steiner et al. |
| 4,946,778 | 8/1990 | Ladner et al. |
| 5,101,025 | 3/1992 | Piatak, Jr. et al. |
| 5,225,539 | 7/1993 | Winter. |
| 5,585,089 | 12/1996 | Queen et al. |

FOREIGN PATENT DOCUMENTS

| | | |
|---|---|---|
| 0 120 694 A2 | 10/1984 | European Pat. Off. |
| 0 125 023 A1 | 11/1984 | European Pat. Off. |
| 0 173 494 A2 | 3/1986 | European Pat. Off. |
| 0 239 400 A2 | 9/1987 | European Pat. Off. |
| 0 125 023 B1 | 6/1991 | European Pat. Off. |
| 0 440 351 A2 | 8/1991 | European Pat. Off. |
| 0 519 596 A1 | 12/1992 | European Pat. Off. |
| 0 592 106 A1 | 4/1994 | European Pat. Off. |
| 0 451 216 B1 | 1/1996 | European Pat. Off. |
| 2188638 | 10/1987 | United Kingdom. |
| 2177096 | 5/1989 | United Kingdom. |
| WO 86/01533 | 3/1986 | WIPO. |
| WO 89/00999 | 2/1989 | WIPO. |
| WO 89/01783 | 3/1989 | WIPO. |
| WO 89/09622 | 10/1989 | WIPO. |
| WO 90/07861 | 7/1990 | WIPO. |
| WO 92/04380 | 3/1992 | WIPO. |
| WO 92/07075 | 4/1992 | WIPO. |
| WO 92/15327 | 9/1992 | WIPO. |
| WO 92/22324 | 12/1992 | WIPO. |
| WO 92/22653 | 12/1992 | WIPO. |
| WO 93/05168 | 3/1993 | WIPO. |

OTHER PUBLICATIONS

Ahmed, *BioEssays*, 6(4):175–177 "Structure and Function of Chimaeric Antibodies".

Alegre et al., *J. Immunol.*, 148(11):3461–3468 (1992) "Effect of a Single Amino Acid Mutation on the Activating and Immunosuppressive Properties of a Humanized OKT3 Monoclonal Antibody".

Antin, et al., *Blood*, 78(8):2139–2149 (1991) "Selective Depletion of Bone Marrow T Lymphocytes With Anti–CD5 Monoclonal Antibodies: Effective Prophylaxis for Graft–Versus–Host Disease in Patients With Hematologic Malignancies".

Barry, Dermatological Formulations p. 181 (1983) "Percutaneous Absorption".

Better, et al., *Science*, 240:1041–1043 (1988) "*Escherichia coli* Secretion of an Active Chimeric Antibody Fragment".

Better et al., *J. Biol. Chem.*, 267(23): 16712–16718 (1992) "Activity of Recombinant Mitogillin and Mitogillin Immunoconjugates".

Better et al., *Proc Natl. Acad. Sci. USA*, 90: 457–461 (1993) "Potent Anti–CD5 Ricin A Chain Immunoconjugates from Bacterially Produced Fab' and F(ab ')2".

Bird et al., *Science*, 242: 423–426 (1988) "Single–Chain Antigen–Binding Proteins".

Bolt et al., *Eur. J. Immunol*, 23(2): 403–411 (1993) "The Generation of Humanized, Non–Mitogenic CD3 Monoclonal Antibody Which Retains In Vitro Immunosuppressive Properties".

Borrebaeck et al., *Bio/Technology*, "Kinetic Analysis of Recombinant Antibody–Antigen Interactions: Relation Between Structural Domains and Antigen Binding".

Boulianne et al., *Nature*, 312: 643–646 (1984) "Production of Functional Chimeric Mouse/Human Antibody".

Brady et al., *J. Mol. Biol.*, 227:253–264 (1992) "Crystal Structure of a Chimeric Fab' Fragment of an Antibody Binding Tumour Cells".

Brown et al., *Proc. Natl. Acad. Sci. USA*, 88: 2663–2667 (1991) "Anti–Tac–H, a Humanized Antibody To The Interleukin 2 Receptor, Prolongs Primate Cardiac Allograft Survival".

Bruggemann et al., *J. Exp. Med.*, 170: 2153–2157 (1989) "The Immunogenicity of Chimeric Antibodies".

Buchner et al., *Biotechnology*, 9: 157–162 (1991) "Renaturation, Purification and Characterization of Recombinant $F_{ab}$–Fragments Produced in *Escherichia coli*".

(List continued on next page.)

*Primary Examiner*—Lila Feisee
*Assistant Examiner*—John Lucas
*Attorney, Agent, or Firm*—McAndrews, Held & Malloy, Ltd.

[57] ABSTRACT

Methods are described for identifying the amino acid residues of an antibody variable domain which may be modified without diminishing the native affinity of the domain for antigen while reducing its immunogenicity with respect to a heterologous species and for preparing so modified antibody variable domains which are useful for administration to heterologous species. Antibody variable regions prepared by the methods of the invention are also described.

23 Claims, 24 Drawing Sheets

OTHER PUBLICATIONS

Byers et al., *Blood*, 75(7): 1426–1432 (1990) "Use of An Anti–Pan T–Lymphocyte Ricin A Chain Immunotoxin in Steroid–Resistant Acute Graft–Versus–Host Disease".

Caron et al., *Cancer Res.*, 52(24): 6761–6767 (1992) "Biological and Immunological Features of Humanized M195 (Anti–CD33) Monoclonal Antibodies".

Carter et al., *Proc. Natl. Acad. Sci. USA*, 89: 4285–4289 (1992) "Humanization of Anti–p185$^{HER2}$ Antibody for Human Cancer Therapy".

Case et al., *Proc. Natl. Acad. Sci. USA*, 86: 287–291 (1989) "Chimeric Cytotoxin IL2–PE40 Delays and Mitigates Adjuvant–Induced Arthritis in Rats".

Cheadle et al., *Mol. Immunol.*, 29: 21–30 (1992) "Cloning and Expression of the Variable Regions of Mouse Myeloma Protein MOPC315 in *E. coli*:Recovery of Active $F_x$ Fragments".

Chothia et al., *The EMBO Journal*, 7(12): 3745–3755 (1988) "The Outline Structure of the T–Cell αβ Receptor".

Chothia et al., *J. Mol. Biol.*, 196: 901–917 (1987) "Canonical Structures for the Hypervariable Regions of Immunoglobulins".

Chothia et al., *Nature*, 342: 877–883 (1989) "Conformations of Immunoglobulin Hypervariable Regions".

Chothia et al., *J. Mol. Biol.*, 186: 651–663 (1985) "Domain Association in Immunoglobulin Molecules. The Packing of Variable Domains".

Chothia and Lesk, *Cold Spring Harbor Symp. Quant. Biol.*, 52: 399–405 (1987) "The Evolution of Protein Structures".

Choy et al., *Scandinavian J. Immunol.*, 36: 291–298 (1992) "Treatment of Rheumatoid Arthritis With Single Dose or Weekly Pulses of Chimaeric Anti–CD4 Monoclonal Antibody".

Co et al., *Nature*, 351: 501–502 (1991) "Humanized Antibodies for Therapy".

Co et al., *Proc. Natl. Acad. Sci. USA*, 88: 2869–2873 (1991) "Humanized Antibodies for Antiviral Therapy".

Co et al., *J. Immunol.*, 148: 1149–1154 (1992) "Chimeric and Humanized Antibodies with Specificity for the CD33 Antigen".

Daugherty, et al., *Nucleic Acids Res.*, 19: 2471–2476 (1991) "Polymerase Chain Reaction Facilitates the Cloning, CDR–grafting, and Rapid Expression of a Murine Monoclonal Antibody Directed Against the CD18 Component of Leukocyte Integrins".

Davies & Metzger, *Ann. Rev. Immunol.*, 1: 87–117 (1983) "Structural Basis of Antibody Function".

Davies and Padlan, *Ann. Rev. Biochem.*, 59: 439–473 (1990) "Antibody–Antigen Complexes".

Derocq et al., *Transplantation*, 44(6): 763–769 (1987) "Rationale for the Selection of Ricin A–Chain Anti–T Immunotoxins for Mature T Cell Depletion".

Eigenbrot et al., *J. Mol. Biol.*, 229: 969–995 (1993) "X–ray Structures of the Antigen–binding Domains from Three Variants of Humanized Anti–p185$^{HER3}$ Antibody 4D5 and Comparison with Molecular Modeling".

Ey et al., *Immunochem.*, 15: 429–436 (1978) "Isolation of pure $IgG_1$, $IgG_{2a}$ and $IgG_{2b}$ Immunoglobulins from Mouse Serum Using Protein A–Sepharose".

Fishwild et al., *Clin. Exp. Immunol.*, 86: 506–513 (1991) "Cytotoxicity Against Human Peripheral Blood Mononuclear Cells and T Cell Lines Mediated By Anti–T Cell Immunotoxins in the Absence of Added Potentiator".

Fishwild et al., *Clin. Exp. Immunol.*, 97: 10–18 (1994) "Characterization of the Increased Cytotoxicity of Gelonin Anti–T Cell Immunoconjugates Compared with Ricin A Chain Immunoconjugates".

Foote et al., *J. Mol. Biol.*, 224: 487–499 (1992) "Antibody Framework Residues Affecting the Conformation of Hypervariable Loops".

Galfre et al., *Nature*, 266: 550–552 (1977) "Antibodies to Major Histocompatibility Antigens Produced by Hybrid Cell Lines".

Glaser et al., *J. Immunol.*, 149(8): 2607–2614 (1992) "Dissection of the Combining Site in a Humanized Anti–Tac Antibody".

Glockshuber et al., *Biochemistry*, 18: 1362–1367 (1990) "A Comparison of Strategies to Stabilize Immunoglobulin $F_V$–Fragments".

Goff et al., *Bioconjugate Chem.*, 1: 381–386 (1990) "Substituted 2–Iminothiolanes: Reagents for the Preparation of Disulfide Cross–Linked Conjugates With Increased Stability".

Goldberg et al., *J. Autoimmunity*, 4: 617–630 (1991) "Immunological Effects of High Dose Administration of Anti–CD4 Antibody In Rheumatoid Arthritis Patients".

Goldberg et al., *Arthritis and Rheumatism*, 33: S153, Abstract D115 (1990) "Preliminary Trial of an Anti–CD4 Monoclonal Antibody (MoAb) in Rheumatoid Arthritis (RA)".

Gorman et al., *Proc. Natl. Acad. Sci. USA*, 88: 4181–4185 (1991) "Reshaping a Therapeutic CD4 Antibody".

Hafler et al., *Neurology*, 36: 777–784 (1986) "Immunologic Responses of Progressive Multiple Sclerosis Patients Treated With An Anti–T–Cell Monoclonal Antibody, Anti–T12".

Hakimi et al., *J. Immunol.*, 147: 1352–1359 (1991) "Reduced Immunogenicity and Improved Pharmacokinetics of Humanized Anti–Tac in Cynomolgus Monkeys".

Hakimi et al., *J. Immunol.*, 151: 1075 (1993) "Humanized Mikβ1. A Humanized Antibody to the IL–2 Receptor β–chain That Acts Synergistically With Humanized Anti––TAC".

Hale et al., *The Lancet*, 11: 1394–1399 (1988) "Remission Induction in Non–Hodgkin Lymphoma With Reshaped Human Monoclonal Antibody Campath–1H".

Hara et al., *Clinical Immunology and Immunopathology*, 49: 223–230 (1988) "Stimulatory Effect of CD5 Antibody on B Cells from Patients With Rheumatoid Arthritis".

Harlow et al., Eds., Antibodies: A Laboratory Manual. Chapter 14. "Immunoassays". Cold Spring Harbor Laboratory, Cold Spring Harbor (1988).

Hodgson, *Biotechnology*, 8: 1245–1247 (1990) "Protein Design: Rules, Empiricism, & Nature".

Horneff et al., *Arthritis and Rheumatism*, 34(2): 129–140 (1991) "Treatment of Rheumatoid Arthritis With An Anti–CD4 Monoclonal Antibody".

Hsiao et al., Antibody Engineering Meeting, Dec. 14–16, 1992, Abstract "Humanization of Anti–CD18 mAb 60.3".

Huse et al., *Science*, 246: 1275–1281 (1989) "Generation of a Large Combinatorial Library of the Immunoglobulin Repertoire in Phage Lambda".

Huston et al., *Proc. Natl. Acad. Sci. USA*, 85: 5879–5883 (1988) "Protein Engineering of Antibody Binding Sites: Recovery of Specific Activity in an Anti–Digoxin Single–Chain Fv Analogue Produced in *Escherichia coli*".

Janin et al., *J. Biol. Chem.*, 265: 16027–16030 (1990) "The Structure of Protein–Protein Recognition Sites".

Jones et al., *Biotechnology*, 9: 88–89 (1991) "Rapid PCR Cloning of Full–Length Mouse Immunoglobulin Variable Regions".

Jones et al., *Nature*, 321: 522–525 (1986) "Replacing the Complementarity–Determining Regions in a Human Antibody with those from a Mouse".

Junghans et al., *Cancer Res.*, 50 (5): 1495–1502 (1990) "Anti–Tac–H, A Humanized Antibody to the Interleukin 2 Receptor with New Features for Immunotherapy in Malignant and Immune Disorders".

Kabat et al., *J. Biol. Chem.*, 252 (19): 6609–6616 (1977) "Unusual Distributions of Amino Acids in Complementarity–Determining (Hypervariable) Segments of Heavy and Light Chains of Immunoglobulins and their Possible Roles in Specificity of Antibody–Combining Sites".

Kelley et al., *Biochem.*, 32: 6828–6835 (1993) "Thermodynamic Analysis of an Antibody Functional Epitope".

Kelley et al., *Biochem.*, 31: 5434–5441 (1992) "Antigen Binding Thermodynamics and Antiproliferative Effects of Chimeric and Humanized Anti–p185$^{HER2}$ Antibody Fab Fragments".

Kernan et al., *J. Immunol.*, 133 (1): 137–146 (1984) Specific Inhibition of in vitro Lymphocyte Transformation by an Anti–Pan T Cell (gp67) Ricin A Chain Immunotoxin.

Kettleborough et al., *Protein Engineering*, 4: 773–783 (1991) "Humanization of a Mouse Monoclonal Antibody by CDR–Grafting: The Importance of Framework Residues on Loop Conformation".

Kirkham et al., *Brit. J. Rheumatology*, 30: 88 Abstract 16 (1991) "Chimaeric (Human/Mouse) CD7 Monoclonal Antibody Treatment in Rheumatoid Arthritis".

Kirkham et al., *Brit. J. Rheumatology*, 30: 459–463 (1991) "Monoclonal Antibody Treatment in Rheumatoid Arthritis: The Clinical and Immunological Effects of a CD7 Monoclonal Antibody".

Kirkham et al., *J. Rheumatology*, 19: 1348–1352 (1992) "Chimeric CD7 Monoclonal Antibody Therapy in Rheumatoid Arthritis".

Knowles, Chapter 22 in Reinherz et al., Leukocyte Typing II, 1: 259–288 (Springer–Verlag, 1986) "Immunochemical Analysis of the T–Cell Specific Antigens".

Koda et al., *Hum. Antibody Hybridomas* 1(1): 15–22 (1990) Review "In Vitro Immunization for the Production of Human Monoclonal Antibody".

Kohler et al., *Eur. J. Immunol.*, 6: 292–295 (1976) "Fusion Between Immunoglobulin–Secreting and Nonsecreting Myeloma Cell Lines".

Kyle et al., *J. Rheumatol.*, 18: 1737–1738 "Humanized Monoclonal Antibody Treatment in Rheumatoid Arthritis". 1991.

Lambert et al., *J. Biol. Chem.*, 246: 12035–12041 (1985) "Purified Immunotoxins that are Reactive with Human Lymphoid Cells".

Laurent et al., *Bone Marrow Transplantation*. 4: 367–371 (1989) "Donor Bone Marrow Treatment With T101 Fab Fragment–Ricin A–Chain Immunotoxin Prevents Graft–Versus–Host Disease".

Lazarovits et al., *J. Immunol.*, 150(11): 5163–5174 (1993) "Human Mouse Chimeric CD7 Monoclonal Antibody (SDZCHH380) for the Prophylaxis of Kidney Transplant Rejection".

Lesk et al., *Nature*, 335: 188–190 (1988) "Elbow Motion in the Immunoglobulins Involves a Molecular Ball–and socket Joint".

Liu et al., *Gene*, 54: 33–40 (1987) "Expression of Mouse: Human Immunoglobulin Heavy–Chain cDNA in Lymphoid Cells".

LoBuglio et al., *Proc. Natl. Acad. Sci. USA*, 86: 4220–4224 (1989) "Mouse/Human Chimeric Monoclonal Antibody in Man: Kinetics and Immune Response".

Marks et al., *J. Mol. Biol.*, 222: 581–597 (1991) "By–Passing Immunization: Human Antibodies from V–Gene Libraries Displayed on Phage".

Marks et al., *J. Biol. Chem.*, 267(23): 16007–16010 (1992) "Molecular Evolution of Proteins on Filamentous Phage".

Martin et al., *Proc. Natl. Acad. Sci. USA*, 86: 9268–9272 (1989) "Modeling Antibody Hypervariable Loops: A Combined Algorithm".

Mathieson et al., *New England J. Med.*, 323 (4): 250–254 (1990) "Monoclonal–Antibody Therapy in Systemic Vasculitis".

McCafferty et al., *Nature*, 348: 552–554 (1990) "Phage Antibodies: Filamentous Phage Displaying Antibody Variable Domains".

Miglietta, et al., *Antibody Engineering Meeting*, Dec. 14–16, 1992 Abstract "Alteration of Framework Residues Modulate Binding of a CDR–Grafted Anti–Human ICAM–1".

Morrison, *Science*, 229: 1202–1207 (1985) "Transfectomas Provide Novel Chimeric Antibodies".

Morrison et al., *Adv. in Immunol.*, 44: 65–92 (1989) "Genetically Engineered Antibody Molecules".

Morrison et al., *Proc. Natl. Acad. Sci.*, 81: 6851–6855 (1984) "Chimeric Human Antibody Molecules: Mouse Antigen–Binding Domains With Human Constant Region Domains".

Munson et al., *Anal. Biochem.*, 107: 220–239 (1980) "LIGAND: A Versatile Computerized Approach for Characterization of Ligand–Binding Systems".

Near et al., *J. Immunol.*, 146 (2): 627–633 (1991) "The Specificity Properties that Distinguish Members of a Set of Homologous Anti–Digoxin Antibodies are Controlled by H Chain Mutations".

Nishimura et al., *Eur. J. Immunol.*, 18: 747–753 (1988) "Expression and Function of a CD5 cDNA in Human and Murine T Cells".

Nisonoff et al., *Archives of Biochem.*, 93 460–462 (1961) "Recombination of a Mixture of Univalent Antibody Fragments of Different Specificity".

Novotny et al., *Proc. Natl. Acad. Sci. USA*, 82: 4592–4596 (1985) "Structural Invariants of Antigen Binding: Comparison of Immunoglobulin $V_L$–$V_H$ and $V_L$–$V_L$ Domain Dimers".

Novotny et al., *J. Mol. Biol.*, 189: 715–721 (1986) "Location of Antigenic Epitopes on Antibody Molecules".

Novotny et al., *Proc. Natl. Acad. Sci. USA*, 83: 226–230 (1986) "Antigenic Determinants in Proteins Coincide with Surface Regions Accessible to Large Probes (Antibody Domains)".

Novotny et al., *Proc. Natl. Acad. Sci. USA*, 83: 742–746 (1986) "Secondary, Tertiary, and Quaternary structure of T–cell–specific Immunoglobulin–like Polypeptide Chains".

Padlan et al., *Proc. Natl. Acad. Sci. USA*, 86: 5938–5942 (1989) "Structure of an Antibody–Antigen Complex: Crystal Structure of the HyHEL–10 Fab–Lysozyme Complex".

Padlan, E.A. *Molecular Immunology*, 28(4/5): 489–498 (1991) "A Possible Procedure For Reducing The Immunogenicity of Antibody Variable Domains While Preserving Their Ligand–Binding Properties".

Peacock et al., *Arthritis and Rheumatology*, 35 (Suppl.) Abstract No. B141 (1992) "An Angiogenesis Inhibitor in Combination with Anti–CD5 Mab Suppresses Established Collagen Induced Arthritis Significantly More Than Single Agent Therapy".

Pluckthun, *Biotechnology*, 9: 545–551 (1991) "Antibody Engineering: Advances From The Use of *Escherichia coli* Expression Systems".

Potter et al., *Proc. Natl. Acad. Sci. USA*, 81: 7161–7165 (1984) "Enhancer–dependent Expression of Human K Immunoglobulin Genes Introduced into Mouse pre–B Lymphocytes by Electroporation".

Presta et al., *J. Immunol*, 151: 2623–2632 (1993) "Humanization of an Antibody Directed Against IgE".

Queen et al., *Proc. Natl. Acad. Sci. USA*, 86: 10029–10033 (1989) "A Humanized Antibody that Binds to the Interleukin 2 Receptor".

Racadot et al., *Brit. J. Rheumatology*, 30: 88 (1991) Abstract "Immunological Follow Up of 13 Patients With Rheumatoid Arthritis Treated by Anti–T CD4+ Monoclonal Antibodies".

Riechmann et al., *Nature*, 332: 323–327 (1988) "Reshaping Human Antibodies for Therapy".

Roberts et al., *Nature*, 328: 731–734 (1987) "Generation of an Antibody with Enhanced Affinity and Specificity for Its Antigen by Protein Engineering".

Robinson et al., *Hum. Antib. Hybridomas*, 2: 84–93 (1991) "Chimeric Mouse–Human Anti–Carcinoma Antibodies that Mediate Different Anti–Tumor Cell Biological Activities".

Rodwell, *Nature*, 342: 99–100 (1989) "Engineering Monoclonal Antibodies".

Roguska et al., *Proc. Natl. Acad. Sci. USA*, 91: 969–973 (1994) "Humanization of Murine Monoclonal Antibodies Through Variable Domain Resurfacing".

Rostaing–Capaillon et al., *Cancer Immunol. Immunother.*, 34: 24–30 (1991) "In Vivo Cytotoxic Efficacy of Immunotoxins Prepared From Anti–CD5 Antibody Linked to Ricin A–Chain".

Routledge et al., *Eur. J. Immunol.*, 21: 2717–2725 (1991) "A Humanized Monovalent CD3 Antibody which can Activate Homologous Complement".

Royston et al., *J. Immunol.* 125(2): 725–731 (1980) "Human T Cell Antigens Defined By Monoclonal Antibodies: The 65,000–Dalton Antigen of T Cells (T65) Is Also Found On Chronic Lymphocytic Leukemia Cells Bearing Surface Immunoglobulin".

Schlom, J. *Molecular Foundations of Oncology*, Samuel Broder (Ed.), Williams and Wilkins, Baltimore, MD Chapter 6 pp. 95–134 "Monoclonal Antibodies: They're More And Less Than You Think".

Sharon et al., *Nature*, 309: 364–367 (1984) "Expression of a $V_H C_K$ Chimaeric Protein in Mouse Myeloma Cells".

Shearman et al., *Antibody Engineering Meeting*, Dec. 10–11, 1990 Abstract "Humanized Antibodies with Specificity for the Human α/β T Cell Receptor".

Shearman et al., *J. Immunol.*, 147(12): 4366–4373 (1991) "Construction, Expression and Characterization of Humanized Antibodies Directed Against the Human α/β Cell Receptor".

Sims et al., *J. Immunol.*, 151(4): 2296–2308 (1993) "A Humanized CD18 Antibody can Block Function Without Cell Destruction".

Singer et al., *J. Immunol.*, 150: 2844–2857 (1993) "Optimal Humanization of 1B4, An Anti–CD18 Murine Monoclonal Antibody, Is Achieved by Correct Choice of Human V–Region Framework Sequences".

Skerra et al., *Science*, 1038–1041 (1988) "Assembly of a Functional Immunoglobulin $F_V$ Fragment in *Escherichia coli*".

Strand et al., *Arthritis and Rheumatism*, 33 (9 Suppl.) (1990) p. S25 "Treatment of Rheumatoid Arthritis With An Anti–CD5 Immunoconjugate: Clinical And Immunologic Findings and Preliminary Results of Re–Treatment".

Studnicka, G.M., *Biochem J.*, 252: 825–831 (1988) "*Escherichia coli* Promoter –10 and –35 Region Homologies Correlate with Binding and Isomerization Kinetics".

Takeda et al., *Nature*, 314: 452–454 (1985) "Construction of Chimaeric Processed Immunoglobulin Genes Containing Mouse Variable and Human Constant Region Sequences".

Tempest et al., *Biotechnology*, 9: 266–271 (1991) "Reshaping a Human Monoclonal Antibody to Inhibit Human Respiratory Syncytial Virus Infection in vivo".

Thornton, *Nature*, 343: 411–412 (1990) "Tackling a Loopy Problem".

Tramontano et al., *J. Mol. Biol.*, 215: 175–182 (1990) "Framework Residue 71 is a Major Determinant of the Position and Conformation of the Second Hypervariable Region in the $V_H$ Domains of Immunoglobulins".

Tramontano et al., *Proteins: Function and Genetics*, 6: 382–394 (1989) "Structural Determinants of the Conformations of Medium–Sized Loops in Proteins".

Verhoeyen et al., *Science*, 239: 1534–1536 (1988) "Reshaping Human Antibodies: Grafting an Antilysozyme Activity".

Verhoeyen et al., *BioEssays*, 8(2): 74–78 (1988) "Engineering of Antibodies".

Vitetta et al., *Science*, 238: 1098–1104 (1987) "Redesigning Nature's Poisons to Create Anti–Tumor Reagents".

Ward et al., *Nature*, 341: 544–546 (1989) "Binding Activities of a Repertoire of Single Immunoglobulin Variable Domains Secreted from *Escherichia coli*".

Winter et al., *Nature*, 349: 293–299 (1991) "Man–Made Antibodies".

Wofsky et al., *J. Immun.*, 134(2): 852–857 (1985) "Treatment of Murine Lupus with Monoclonal Anti–T Cell Antibody".

Woodle et al., *J. Immunol.*, 148: 2756–2763 (1992) "Humanized OKT3 Antibodies: Successful Transfer of Immune Modulating Properties and Idiotype Expression".

Wu et al., *J. Exp. Med.*, 132: 211–250 (1970) "An Analysis of the Sequences of the Variable Regions of Bence Jones Proteins and Myeloma Light Chains and Their Implications for Antibody Complementarity".

Wu and Kabat., *Mol. Immunol.*, 29(9): 1141–1146 (1992) "Possible Use of Similar Framework Region Amino Acid Sequences Between Human and Mouse Immunoglobulins for Humanizing Mouse Antibodies".

FIG. 1A

LIGHT CHAIN

```
pos             10         20        x  30x         40              50
HYH   DIVLTQS PATLSVTPGNSVSLSCRASQS IG NNLHWYQQKSHESPRLLIK          YAS
MCPC  DIVMTQS PSSLSVSAGERVTMSCKSSQS LL!NFLAWYQQKPGQPPKLLIY          GAS
NEWM  XSVLTQ  PPSVSGAPGQRVTISCTGSSSN IG!NHVKWYQQLPGTAPKLLIF
KOL   QSVLTQ  PPSASGTPGQRVTISCSGTSSN IGSSTVNWYQQLPGMAPKLLIY         RAD
bind  +-+o++   o++++++o+++++-+-o--   ----o-o++o++o+--oo-             ---
bury  +-+-+-+  +-+o+-+++++-+-++++-   -+++--==-=o=+++o=o=---          +++
risk  •▲••▲•■  •▲■■▲•▲•■•■■■■■■▲•■   •▲■▲■▲•■■■■■■■■■▲•▲■▲■          ■■■
mod     •       • •  •  •  • •          • •      •  •                • pos          60             70         80             90    x           100
HYH   QSISGIPSRFSGSG SGT DFTLSINSVETEDFGMYFCQQS NS  WPYT FGGGTKLDIK
MCPC  TRESGVPDRFTGSG SGT DFTLTISSVQAEDLAVYYCQND HS  YPLT FGAGTKLEIK
NEWM  HNNA  RFSVSK  SGS SATLAITGLQAEDEADYYCQSY DR  SLRV FGGGTKLTVL
KOL   MRPSGVPDRFSGSK SGA SASLAIGGLQSEDETDYYCAAW DV! NAYV FGTGTKVTVL
bind  -+oo++o++++-+-  +o+ +-+++++++++++o--+-     ---  ---o o+++++++++
bury  ++o++-o+o-+-+-  +-+ +-+--+--+++-+-=-=-==   ++o  oo=- =-++-+-+++
risk  ■•▲▲•■■▲•▲■■•■  •■■ •■■■■■■■■■■■■■■■■■■■   •■   ■■■■ ■■■■■■■■■■
mod    •                                                      •       •
```

HEAVY CHAIN

```
pos         10               20              30              40              50       x
HYH    DVQLQESGPS   LVKPSQTLSLTCSVTG   DSITSDYWSWIRKFPGNRLEYMGYVS   YSGST
MCPC   EVKLVESGGG   LVQPGGSLRLSCATSG   FTFSDFYMEWVRQPPGKRLEWIAASR!NKYTT
NEWM   QVQLEQSGPG   LVRPSQTLSLTCTVSG   TSFDDYYSTWVRQPPGRGLEWIGYVF   YHGTS
KOL    EVQLVQSGGG   VVQPGRSLRLSCSSSG   FIFSSYAMYWVRQAPGKGLEWVAIIWDDGSDQ
bind    o-+o+++o+    +++o+++++-+-+-    -------+--------o-+++o+-oo-----
bury    +-+-+-o+     +o++++++-+-+--    -+-++o+-=+o=++++o=o=--o-o++o++
risk   ◂•▪          ◂•▪▴▴◂•◂•▪         ▪▪▪▪▪▪▪▪▪▪▪▪▪▪▪▪▪▪▪◂•▪▪
mod      •            •                 •     •        •
```

```
pos         60              70          80 abc           90      x100a         110
HYH    YNPSLKSRISITRDTSKNQYYLDLNSVTTEDTATYYCANWD              GDYWGQGTLVTVSA
MPCP   EYSASVKGRFIVSRDTSQSILYLQMNALRAEDTAIYYCARNYY !          WYFDVWGAGTTVTVSS
NEWM   DTDTPLRSRVTMLVNTSKNQFSLRLSSVTAADTAVYYCARNLIA           GCIDVWGQGSLVTVSS
KOL    HYADSVKGRFTISRNDSKNTLFLQMDSLRPEDTGVFCARDGG !           FGPDYWGQTPVTVSS
bind    -oooo+o++-+-+-+o++o+ +++++++--+-++-+++o------         -------o++++++++
bury    +o-+-+o-+-+--+o+o++o+ +-+-+-+++++++-+-+o-!=!-=oo+o    oo=oo=-+-+-++
risk   ▪◂▪▪◂◂◂•◂▪   ▪▪▪◂▪▪▪◂▪◂◂▪▪▪▪▪▪▪▪▪▪◂◂▪▪▪▪▪▪◂▪▪          ▪▪▪▪▪▪
mod                   •        •              •
```

FIG. 1B

LIGHT CHAIN

```
pos                    10           20         x  30x         40               50
bind      +-+o+++    o++++++o++++++++-+-o---  ------o-o-o++++o++++o+-oo-      ----
bury      +-+-+-+    o++o+-++++++++-+-+-+++   -++++-=-=o=+++++o=o=-o          +++
risk      ■ ■        ■   ■       ■       ■    -+++-=-=o=+++++o=o=-o ■         ■■■
mod       ●●         ●  ●●●  ▲●●●        ■▲●    ▲●●  ▲●           ■▲●●●■■
hK1   DIQMTQS  PSSLSASVGDRVTITCrASQx     Is xyLxWYQQKPGkAPklLIY      aAS
hK3   EIVLTQS  PgTLSlSPGERATLSCRASQS    vsssyLAWYQQKPGQAPRLLIY       gaS
hK2   DIVMTQS  PLSLPVTPGEPASISCRSSQS    LlnnYlnWYLQKPGQSPqLLIY       lgS
hL1   xSVLTQP  PS aSgtPGQrVtISCsGsssS   iGxnxVxWYQqlPGtAPKLLIY       n n
hL2   XSALTQP  aS VSGSPGQSiTISCtGtss    VgynxVSWyQQhPGkAPK LIY       dv
hL3   SYeLTQP  PS vSVsPGQTA ITCsGdx     lxxxyvxWYQQkPGQaPvLVIY       d
hL6   nfmltqp  hs vsespgktvtisctxsxg    iasxyvqwyqqrpgsapttviy       edn
hK4   divmtqs  pdslavslgeratinckssqs    vlknylawyqqkpgqppkllij       was
hL4   seltqp   ps vsvapgqt ritcsgdx     lgxydaxwyqqkpgqapllviy       grn
hL5   saltqp   ps asgspgqsvtisctgtss    vgxxyvswyqqh g apk  i        ev
```

FIG. 5A

HEAVY CHAIN

```
                    10              20              30              40              50    x
pos         o-+o+++++o+     +++o+++++++-+oo-   -+-+-+-+-+-+-o-o++++o++-oo-   -+-++o+++++o+++o=++++o=o=-   -o-o++o++
bind        +-+-+-+-o+      +o++++++-+-+-+-    -+-++o+-=-=o=-=:=o=++++=o+o    -o+++o+
bury        ■■■■■■■■■        ●▲●▲■●▲           ■■■■■■■■■■■■▲■●▲●●     ■■■●▲●● ■■●▲    ▲■■■
risk        ▲■■●● ●           ●●   ■■●▲         ■■■■■■■■■■■■■■▲■●●   ●●       ●  ●●
mod            ●
hH3         EVQLvESGGG      LVqPGGSLRLSCAASG   FtFsxxxmxWVRQApGKgLEWV xxixxxxxgx
hH1         QVqLvqSGaE      VkKPGxSvxvSCKxSG   yyFxxyxixWvRQaPGxGLEWvGxixpxxgxt
hH2         xvtlxesgpx      lvlptqtltltctvsg   xslsxxxvxwirqppgkxlewlaxix     xddd 60              70              80  abc         90              x100a     110
pos         -oooo+o+++      -+-+o+++o-+-+-+    -+++++++-+-+-+-+-+++++-+-+-   -+-:-+-O-:-:-:   +++++++++++++
bind        +o-+o-++o       -+-+o+++o+         -+-+-+-+-+-+-+-+-+-o:=-:-    =oo+o  oo=oo=-+-:-+-+++
bury        ■▲■■▲▲▲●■■●●  ●▲■●●●●▲ ●●■  ●●●▲■●●●●▲■●●■  ■●●●▲■●    ■■■■■■■■
risk                ●        ●●                ●●●  ● ●                        ●         ●●
mod                                                                                      ●●
hH3         xyadSVkGRFTISRddSKNtlyLqMnsLraeDTAVYYCarxxxxxx   xxxxxWGqGTlVTvSS
hH1         xyapxfggRVTxtrdxSxntayMeLxsLrseDtAVYYCArxxxxxx   xxxxxwgqGtlvtVSS
hH2         xyxtslrsrltiskdtsknqvvlxxxxxdpxdtatyycarxxxxxx   xxxdvwggttvtvss
```

FIG. 5B

LIGHT CHAIN

```
pos                      10                  20           x 30x          x            40                 50
hk1        DIQMTQS PSSLSASVGDRVTITCrASQx     Is xyLxWYQQKPGkAPKlLIY        aAS
H65        DIKMTQS PSSMYASLGERVTITCKASQD     IN SYLSWFQQKPGKSPKTLIY        RAN
bind       +-+o+++ o++++++o+-+++++           --+ ---o-o++-+o++-oo-         ---
bury       +-+-+-+ o++o+-+++++--+            -+++ -+++--=o=+++o=o--o       +++
risk       ●●■■■ ▲●+●●■▲●●■                 ■ -+++●●■▲●●■                 ■■■
mod
M/H             H         MH    M H                  M                M   M M
prop       DIQMTQS PSSMSASLGDRVTITCRASQD     IN SYLSWFQQKPGKSPKTLIY        RAN pos                      60                  70             80             90         x         100
hk1        xLxsGVPSRFsGSG    SGT  xFTITlSsLQpeDfATYYCqqy   xx   xPxt FGqGTkveik
H65        RLVDGVPSRFSGSG    SGQ  DYSLTISSLDYEDMGIYYCQQY   DE   SPWT FGGGTKLEIK
bind       -+oo+++to++-+-    +o+  +-++++++++--+++++---    --    ---o o++++++++
bury       ++o+-+-o+o-+-++   +-+  +-+++++--+++-++++-++    ++o   oo= =-+-++-+++
risk       ●▲●■▲●■           ●●   ●●■●●■■■                ■     ■■  ●●■■
mod                                                                    ●   ●
M/H        M MM              H     H mMH       Hm  hMM     MM       m    m  M
prop       RLVDGVPSRFSGSG    SGT   DYTLTISSLQYEDFGIYYCQQY  DE        SPWT FGGGTKLEIK
```

FIG. 6A

HEAVY CHAIN

```
pos              10              20              30           40               50  x
hH3     EVQLvESGGG      LVqPGGSLRLSCAASG      FtFsxxxmxWVRQApGKgLEWVxxxixxkxxgx
h65     QIQLVQSGPE      LKKPGETVKISCKASG      YTFTNYGMNWVKQAPGKGLRWMGWINTHTGEP
bind    O-+O++++O+      +++O++++++-+-+--      -----+--O-O++O++O+-OO-          ---
bury    +-+-+-O+        +O++++++-+-+-++-      -+-++O+-!=!=O=++++O=O-O++O++   
risk    •▲■■▲           •▲▲■▲■■▲■▲•▲          -+-++O+-!=!=O=++++•=•▲▲■▲•• ▲▲■■■■
mod             •       •                                     •         •
M/H     MM      MH      Mm   HHMHM      H     M  MMMM  M        M MMM MMMMMM
prop    QIQLVQSGPG      LKKPGGSVRISCAASG      YTFTNYGMNWVKQAPGKGLRWMGWINTHTGEP pos           60           abc   80          abc        90              x100a     110
hH3     xyadSVkGRFTISRddsKNtlyLqMnsLraeDTAvYYCarxxxx          xxxxxWGqGTlVTvSS
H65     TYADDFKGRFTISRDNAKNSLYLQMNSLRAEDTATYFCTRRGYD          WYFDVWGAGTTVTVSS
bind    -OOOO++++++-+O+O+-+-+-+++++++++-O-!-!---        ----+-O++++++++++
bury    +O-+O-++O++O+-+-+++O++-+-+++++++++-!=!--OO+O    OO=OO=+-!-!-+!-++
risk    ▲■▲▲■▲•▲■▲▲  •   ▲▲▲•▲▲■▲•••▲■■■■ ■▲•■■         •••▲■■■■■■▲•• ••
mod                                       •••     •                  •  •
M/H     M  MM     HM MhM HM M   M h hh     M M M MMMM            MMMM  h  m
prop    TYADDFKGRFTFSLDTSKSTAYLQINSLRAEDTATYFCTRRGYD          WYFDVWGQGTTVTVSS
```

```
SH65K-1
AGT CGT CGA CAC GAT GGA CAT GAG GAC CCC TGC TCA GTT TCT TGG CAT CCT CCT ACT
CTG GTT TCC AGG TAT CAA ATG TGA CAT CCA GAT GAC TCA GT

HUH-K1
TGA CTC GCC CGG CAA GTG ATA GTG ACT CTG TCT CCC AGA GAT GCA GAC ATG GAA GAT
GAG GAC TGA GTC ATC TGG ATG TC

HUH-K2
TCA CTT GCC GGG CGA GTC AGG ACA TTA ATA GCT ATT TAA GCT GGT TCC AGC AGA AAC
CAG GGA AAT CTC CTA AGA CCC T

HUH-K3
GAT CCA CTG CCA CTG AAC CTT GAT GGG ACC CCA TCT ACC AAT CTG TTT GCA CGA TAG
ATC AGG GTC TTA GGA GAT TTC C

HUH-K4
GGT TCA GTG GCA GTG GAT CTG GGA CAG ATT ATA CTC TCA CCA TCA GCA GCC TGC AAT
ATG AAG ATT TTG GAA TTT ATT G

HUH-K5
GTT TGA TTT CAA GCT TGG TGC CTC CAC CGA ACG TCC ACG GAG ACT CAT CAT ACT GTT
GAC AAT AAT ACA GAT CCA GTT CTT C

HUH-G1
TGT CGA CAT CAT GGC TTG GGT GTG GAC CTT GCT ATT CCT GAT GGC AGC TGC CCA AAG
TGC CCA AGC GAT CCA GTT GCA G

HUH-G2
AAG GTA TAC CCA GAA GCT GCG CAG GAG ATT CTG ACG GAC CCT CCA GGC TTC TTC AGG
CCA GGT CCA GAC TGC ACC AAC TGG ATC T
```

FIG. 7A-2

```
HUH-G3
GCA GCT TCT GGG TAT ACC TTC ACA AAC TAT GGA ATG AAC TGG GTG AAG CAG GCT CCA
GGA AAG GGT TTA GAG TGG ATG GGC TGG

HUH-G4
AAA GAG AAG GTA AAC CGT CCC TTG AAG TC A TCA GCA TAT GTT GGC TCT CCA GTG TGG
GTG TTT ATC CAG CCC ATC CAC CTT AAA C

HUH-G5
CAC GGT TTA CCT TCT CTT TGG ACA CGT CTA AGT GCA CTG CCT ATT TAC AGA TCA ACA
GCC TCA GAG CCG AGG ACA CGG CTA CAT

HUH-G6
AGG AGA CGG TGA CCG TGG TCC CTT GGC CCC AGA CAT CGA AGT ACC AGT CGT AAC CCC
GTC TTG TAC AGA AAT ATG TAG CCG TGT CCT CGG C

H65G-2S
ACT AGT GTC GAC ATC ATG GCT TGG GT

H65-G2
GAG GAG ACG GTG ACC GTG GT

H65K-2S
AGT CGT CGA CAC GAT GGA CAT GAG GAC

JK1-HindIII
GTT TGA TTT CAA GCT TGG TGC
```

FIG. 7B

HUH-G11
TGT CGA CAT CAT GGC TTG GGT GTG GAC CTT GCT ATT CCT GAT GGC AGC TGC CCA AAG
TGC CCA AGC AGA GAT CCA GTT GGT GCA G

HUH-G14
AAA GAG AAG GTA AAC CGT CCC TTG AAA GAA TCA GCA TAT GTT GGC TCT CCA GTG TGG
GTG TTT ATC CAG CCC ATC CAC TCT AAA C

HUH-G13
GCA GCT TCT GGG TAT ACC TTC ACA AAC TAT GGA ATG AAC TGG GTG CGC CAG GCT CCA
GGA AAG AAT TTA GAG TGG ATG GGC TGG

HUH-G16
GAG GAG ACG GTG ACC GTG GTC CCT TGG CCC CAG ACA TCG AAG TAC CAG TCG TAA CCC
CGT CTT GTA CAG AAA TAC ACA GCC GTG TCC TCG GC

HUH-G15
GAC GGT TTA CCT TCT CTT TGG ACG ATT CTA AGA ACA CTG CCT ATT TAC AGA TCA ACA
GCC TCA GAG CCG AGG ACA CGG CTG TGT ATT

HUH-G12
AAG GTA TAC CCA GAA GCT GCG CAG GAG ATT CTG ACG GAC CCT CCA GGC TTC ACC AGG
CCT CCC CCA GAC TGC ACC AAC TGG ATC TC

HUH-K6
TCA CTT GCC GGG CGA ATC AGG ACA TTA ATA GCT ATT TAA GCT GGT TCC AGC AGA AAC
CAG GGA AAG CTC CTA AGA CCC T

HUH-K8
GAT CCA CTG CCA CTG AAC CTT GAT GGG ACC CCA GAT TCC AAT CTG TTT GCA CGA TAG
ATC AGG GTC TTA GGA GCT TTC C

HUH-K7
TGA CTC GCC CGG CAA GTC ACT CTG TCT CCT ACA GAT GCA GAC AGG GAA GAT
GGA GAC TGA CTC TGG ATC TC

```
              10          20          30          40          50
              |           |           |           |           |
ACTAGTGTCG   ACATCATGGC  TTGGGTGTGG  ACCTTGCTAT  TCCTGATGGC
AGCTGCCCAA   AGTGCCCAAG  CACAGATCCA  GTTGGTGCAG  TCTGGACCTG
GCCTGAAGAA   GCCTGGAGGG  TCCGTCAGAA  TCTCCCTGCGC AGCTTCTGGG
TATACCTTCA   CAAACTATGG  AATGAACTGG  GTGAAGCAGG  CTCCAGGAAA
GGGTTTAAGG   TGGATGGGCT  GGATAAACAC  CCACACTGGA  GAGCCAACAT
ATGCTGATGA   CTTCAAGGGA  CGGTTTACCT  TCTCTTTGGA  CACGTCTAAG
AGCACTGCCT   ATTTACAGAT  CAACAGCCTC  AGAGCCGAGG  ACACGGCTAC
ATATTTCTGT   ACAAGACGGG  GTTACGACTG  GTACTTCGAT  GTCTGGGGCC
AAGGGACCAC   GGTCACCGTC  TCCTC
```

FIG. 8A

```
           10         20         30         40         50
           |          |          |          |          |
AGTCGTCGAC ACGATGGACA TGAGGACCCC TGCTCAGTTT CTTGGCATCC
TCCTACTCTG GTTTCCAGGT ATCAAATGTG ACATCCAGAT GACTCAGTCT
CCATCTTCCA TGTCTGCATC TCTGGGAGAC AGAGTCACTA TCACTTGCCG
GGCGAGTCAG GACATTAATA GCTATTTAAG CTGGTTCCAG CAGAAACCAG
GGAAATCTCC TAAGACCCTG ATCTATCGTG CAAACAGATT GGTAGATGGG
GTCCCATCAA GGTTCAGTGG CAGTGGATCT GGGACAGATT ATACTCTCAC
CATCAGCAGC CTGCAATATG AAGATTTTGG AATTTATTAT TGTCAACAGT
ATGATGAGTC TCCGTGGACG TTCGGTGGAG GCACCAAGCT TGAAATCAAA
```

FIG. 8B

LIGHT CHAIN

```
pos              10         x  20               x  30x         x  40              50
EU    DIQMTQS  PSTLSASVGDRVTITCRASQS    IN TWLAWYQQKPGKAPKLLMY    KAS
hK1   DIQMTQS  PSSLSASVGDRVTITCrASQx    Is sYLxWYQQKPGKAPKILIY    aAS
TAC   QIVLTQS  PAIMSASPGEKVTITCSASSS    IS YMHWFQQKRGTSPKLWIY     TTS
bind  +-+o+++  o++++++o+-+++++++++-+    -+++++o-o++++o+++++oo-    ---
bury  +-+-+-+  o++o+-+++-+-+-+-+-++-    -+++++=o=+=+=++=++=o=     +++
risk  ••▲•  ■  ••▲•••▲••••■              ••▲•■••••▲•••          ■■
mod   
M/H   H HM    HHM       M HH     h  M              M MM M   hM        MM
prop  DIQLTQS  PSSMSASPGDRVTITCRASSS    IS YMHWFQQKPGKSPKLWIY     TTS
Que   DIQMTQS  PSTLSASVGDRVTITCSASSS    IS YMHWYQQKPGKAPKLLIY     TTS pos        60         70          80         90     x    100
EU    SLESGVPSRFIGSG SGT EFTLTLTISSLQPDDFATYYCQQY  NS  DSKM FGQGTKVEVK
hK1   xLxsGVPSRFsGSG SGT xFTlTISSlQpeDfATYYCqqy    xx  xPxt FGqGTkveik
TAC   NLASGVPARFSGSG SGT SYSLTISRMEAEDAATYYCHQR    ST  YPLT FGSGTKLELK
bind  -+oo++o+o+++-+   +o+ +-++++-++++++-+-+       --   +++ +-+-+++++
bury  +-oo++-o+o-++-+  +-+ +-++++-+-++-++-++-+     -o-  oo= =-+-+++
risk  ■•▲•■•■•         •    •■••••                 ■    ••■ ••
mod                                          •
M/H   M M   H         mMH    hMHm    h          M M MM M M       h  M   m
prop  NLASGVPSRFSGSG SGT SYTLTISSMQAEDFATYYCHQR    ST  YPLT FGQGTKLELK
Que   NLASGVPARFSGSG SGT EFTLTISSLQPDDFATYYCHQR    ST  YPLT FGQGTKVEVK
```

FIG. 10A

HEAVY CHAIN

```
pos              10           20           30         40        50  x
EU      QVQLVQSGAE  VKKPGSSVKVSCKASG GTFSRSAIIWVRQAPGQGLEWMGGIVPMFGPP
hH1     QVqLvqSGaE  VkKPGxSvxvSCKxSG yyFxxyxixWvRQaPGxGLEWvGxixpxxgxt
TAC     QVQLQQSGAE  LAKPGASVKMSCKASG YTFTSYRMHWVKQRPGQGLEWIGYINPSTGYT
bind    o-+O++++O+  +++O+++++++-+OO- ---------O-O+++O+++O+-OO---------
bury    +-+-+-+-O+  +O+++++-+-+-+-+- -+-++O+-=-=O=++++O=O=--O-O+++O++
risk    ▲■●■●■●■▲●  ●▲●▲●●●■●■●■●■▲■ ■■■■■■■■■■■■▲■●▲●●▲■▲■■■■■■■■■■■
mod      ●  ●  ●  ● ●  ● ●●● ● ● ●                  ● ●●
M/H        M        hM   m  mM   M   M MM MMM  M h  m    M M M MM M
prop    QVQLQQSGAE  VAKPGASVKMSCKASG YTFTSYRMHWVKQAPGQGLEWIGYINPSTGYT
Que     QVQLVQSGAE  VKKPGSSVKVSCKASG YTFTSYRMHWVRQAPGQGLEWIGYINPSTGYT pos      60        70        80  abc      90        x100a      110
EU      NYAQKFQGRVTITADESTNTAYMELSSLRSEDTAFYFCAG GYGIY  YSPEEYNGGLVTVSS
hH1     xyapxfqgRVTxtrdxSxntayMeLxsLrseDtAvYYCArxxxxx   xxxxwgqGtlvtVSS
TAC     EYNQKFKDKATLTADKSSSTAYMQLSSLTFEDSAVYYCAR GGGV    FDYWGQGTTLTVSS
bind    -OOOO+O++++-+-+O++O+-++++++++++++++-O------  -----O++++++++++
bury    +O-+O-++O-+-+-+O++O+-+-+-++-+++-+-O-=-=-=OO+O OO=OO=-+--+-+-++
risk    ■▲■▲▲■▲●▲■●■●■●▲●●▲●■●■●■●●■●●●■●■▲■■■■■■■■■■  ■■■■■■■●■■●■●■●●
mod            ●  ● ● ● ●● ● ● ● ●● ●●● ●                  ●  ●  ● ●●
M/H     M MMM MhMM M M M mM   h m  hh  h        MMMM    MMM      M
prop    EYNQKFKGKATLTADKSSSTAYMELSSLRSEDTAVYYCAR GGGV    FDYWGQGTTLTVSS
Que     EYNQKFKDKATITADESTNTAYMELSSLRSEDTAVYYCAR GGGV    FDYWGQGTLVTVSS
```

FIG. 10B

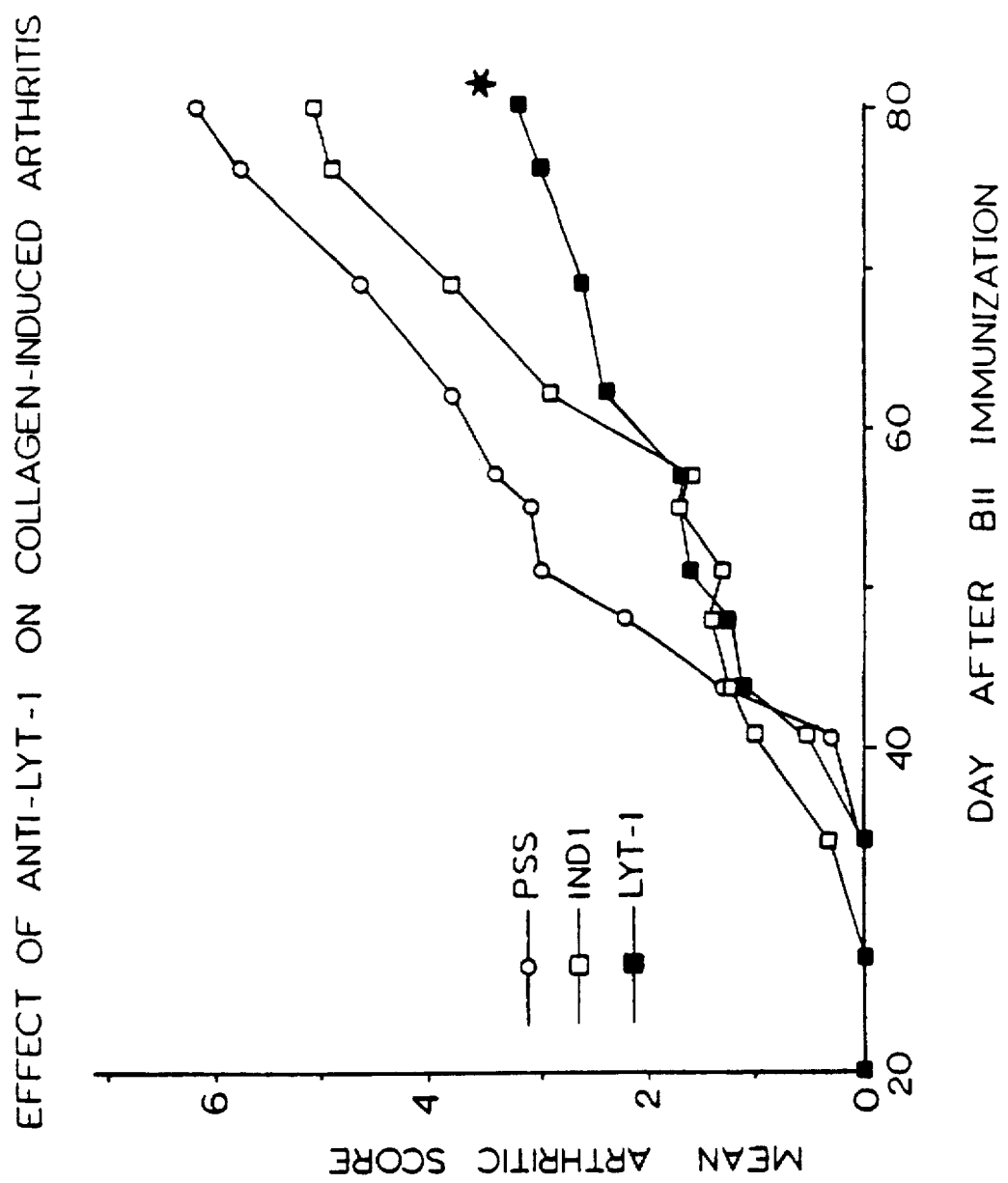

FIG. 13A
FIG. 13B
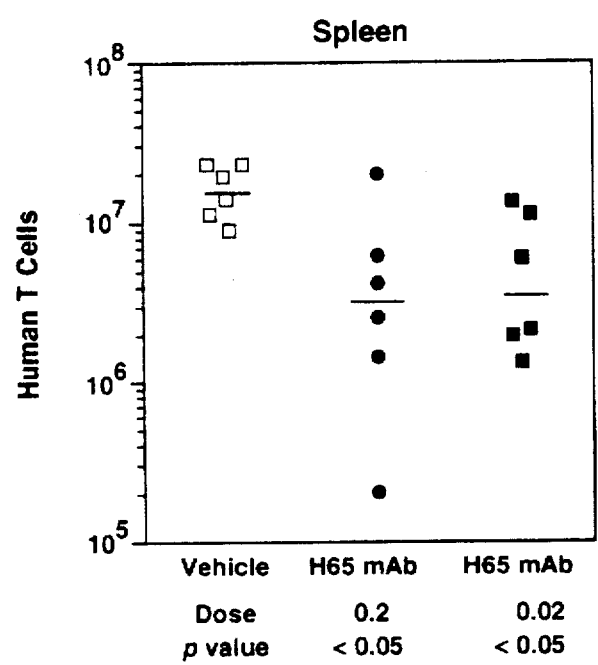
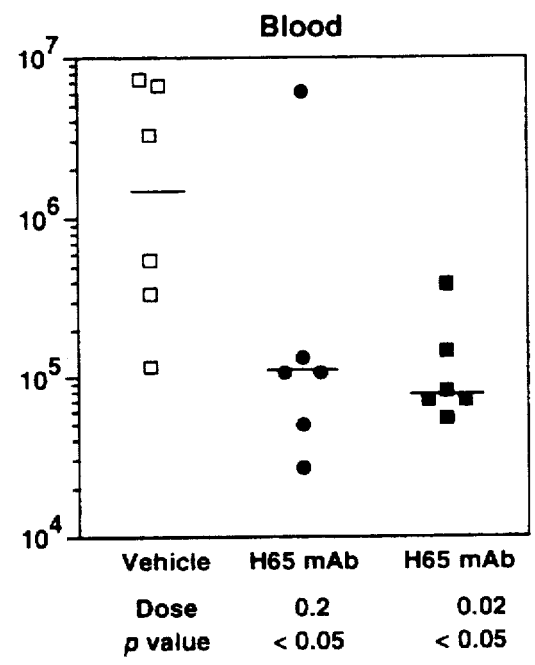

LIGHT CHAIN

```
pos                  10          x  30x          40                  50
H65    DIKMTQS PSSMYASLGERVTITCKASQD  IN SYLSWFQQKPGKSPKTLIY          RAN
bind   +-+o+++  o++++++o+-+++++-+-+-  ---+-o-o++o++o+-oo-             +++
bury   +-+-+-+  o++o+--+++++--+-+++-  -+++++-=o=++++++o=o-=-o         ■■■
risk   ●■●■■■■  ●●●●▲●▲■■■           -+++=+-==o=+++●▲●▲■■■           ■■■
hK1    DIQMTQS PSSLSASVGDRVTITCrASQx  Is xyLxWYQQKPGkAPklLIY          aAS
M/H                  H^    H          H^  M M M            H M       M M
prop   DIQMTQS PSSLSASVGDRVTITCRASQD  IN SYLSWFQQKPGKAPKTLIY          RAN pos          60            70              80          90    x         100
H65    RLVDGVPSRFSGSG SGQ DYSLTISSLDYEDMGIYYCQQY DE       SPWT FGGGTKLEIK
bind   -+oo++o+-+-+-  +o+ +--+++++-+-++-++++++-o- ---     ---o  o++++++++
bury   ++o+-o+o-+-+   +-+ -+--++++-+-+-=+-++●■■■ ++o     oo==   ■=-+-+++
risk   ●●▲▲■●●▲▲■■■   ●■■ ●■■■■■■■■■■■■■■■■■■■■■ xx      MM    ●■●■■■■■■
hK1    xLxsGVPSRFsGSG SGT xFTlTISsLQpeDfATYYCqgy  xx      xPxt  FGqGTkveik
M/H    M hh                  ^M^                 MM      M M        ^   M
prop   RLESGVPSRFSGSG SGT DYTLTISSLQYEDFGIYYCQQY DE       SPWT FGGGTKLEIK
```

FIG. 16A

HEAVY CHAIN

```
pos           10              20              30              40          50    x
H65      QIGLVQSGPE      LKKPGETVKISCKASG      YTFTNYGMNWVKQAPGKGLRWMGWINTHTGEP
bind     O-+O++++O+      +++O++++++-+-++OO-      ------O-O++++O++++O+-OO------
bury     +-+-+-+-O+      +O+++++++-+-+-++-      -+-++O+-=-=O=+++++O=O-O++O++
risk     ▲■●●●●●▲●      ●▲▲●■▲●●●■●●▲▲      ■▲▲●▲●▲●▲●■▲■▲●●▲■■■■■
hH3
M/H
prop     EVQLvESGGG      LVqPGGSLRLSCAASG      FtFsxxxxmxWVRQApGKgLEWVxxxixxxxxgx
         HM   M  H^      H^   ^^M^M  ^         M  MMMM M   H      H  MmM MMMMMMM
         EIQLVQSGGG      LVKPGGSVRISCAASG      YTFTNYGMNWVRQAPGKGLEWMGWINTHTGEP pos           60              70         80  abc             90      x100a         110
H65      TYADDFKGRFAFSLETSASTAYLQINNLKNEDTATYFCTRRGYD             WYFDVWGAGTTVTVSS
bind     -OOOO+O+++-+-+-++O+O+-++++++O-+----:----       ------O++++++++++-  ●●
bury     +O-+O-++O+++-+-+O++O+-++++++O-+-====OO+O      OO=OO=+-=-+-+-++    ●●
risk     ▲■▲▲▲●●▲■■■■●■●●●●●▲●▲▲●●▲●▲●     ■■■■●▲■   ■■■■●●●●●●●●●■  ■■
hH3
M/H      xyadSVkGRFTISRddSKNtlyLqMnsLraeDTAvYYCarxxxx  xxxxxWGgGT1VTvSS
         M    HM   ^M M^h  ^HM   M ^   ^       h M  MMMM         MMMM
prop     TYADSFKGTRTFSLDDSKNTAYLQINSLRAEDTAVYFCTRRGYD      WYFDVWGQGTTVTVSS
```

FIG. 16B

MODIFIED ANTIBODY VARIABLE DOMAINS

CROSS-REFERENCE TO RELATED APPLICATIONS

This Application is the U.S. National Phase of PCT/US92/10906, filed Dec. 14, 1992 (abandoned), which is a continuation-in-part of U.S. application Ser. No. 07/808,464, filed Dec. 13, 1991 (abandoned).

FIELD OF THE INVENTION

The present invention relates, in general, to methods for preparing a modified antibody variable domain by determining the amino acid residues of the antibody variable domain which may be modified without diminishing the native affinity of the domain for antigen while reducing its immunogenicity with respect to a heterologous species; to methods of preparation of and use of antibody variable domains having modifications at the identified residues which are useful for administration to heterologous species; and to the variable regions so modified. More particularly, the invention relates to the preparation of modified mouse antibody variable domains, which are modified for administration to humans, the resulting antibody variable domains themselves, and the use of such "humanized" antibodies in the treatment of diseases in humans.

BACKGROUND

Application of unmodified mouse monoclonal antibodies in human therapy is problematic for three reasons. First, an immune response against the mouse antibodies is mounted in the human body. Second, the antibodies have a reduced half-life in the human circulatory system. Third, the mouse antibody effector domains may not efficiently trigger the human immune system.

There are three methods which have attempted to eliminate the foregoing problems. Junghans et al., *Cancer Res.*, 50, 1495–1502 (1990) and other publications describe the utilization of genetic engineering techniques to link DNA encoding murine variable regions to DNA encoding human constant regions, creating constructs which when expressed generate a hybrid mouse/human antibody.

Also by genetic engineering techniques, the genetic information from murine hypervariable complementarity determining regions (CDRs) may be inserted in place of the DNA encoding the CDRs of a human monoclonal antibody to generate a construct encoding a human antibody with murine CDRs. This technique is known as "CDR grafting". See, e.g., Jones et al., *Nature*, 321, 522–525 (1986); Junghans et al., supra.

Protein structure analysis may be used to "add back" murine residues, again by genetic engineering, to first generation variable regions generated by CDR grafting in order to restore lost antigen binding capability. Queen et al., *Proc. Natl. Acad. Sci. USA*, 86, 10029–10033 (1989); Co, et al., *Proc. Natl. Acad. Sci. USA*, 88, 2869–2873 (1991) describe versions of this method. The foregoing three methods are techniques to "humanize" mouse monoclonal antibodies.

As a result of the humanization of mouse monoclonal antibodies, specific binding activity of the resulting humanized antibodies may be diminished or even completely abolished. For example, the binding affinity of the modified antibody described in Queen et al., supra, is reported to be reduced three-fold; in Co et al., supra, is reported to be reduced two-fold; and in Jones et al., supra, is reported to be reduced two- to three-fold. Other reports describe order-of-magnitude reductions in binding affinity. See, e.g., Tempest et al., *Bio/Technology*, 9, 266–271 (1991); Verhoeyen et al., *Science*, 239, 1534–1536 (1988).

A system for differentiating between the various subsets of T Cells, based upon cell surface antigens, is the Clusters of Differentation System (hereinafter referred to as the "CD System"). The CD System represents standard nomenclature for molecular markers of leukocyte cell differentation molecules. See Leukocyte Typing III White Cell Differentiation Antigens (Michael, ed. Oxford Press 1987), which is incorporated herein by reference.

So-called "pan T cell" markers (or antigens) are those markers which occur on T Cells generally and are not specific to any particular T cell subset(s). Pan T Cell markers include CD2, CD3, CD5, CD6, and CD7. The CD5 cluster antigen, for example, is one of the pan T markers present on about 85–100% of the human mature T lymphocytes and a majority of human thymocytes. CD5 is also present on a subset, about 20%, of B cells. Extensive studies using flow cytometry, immunoperoxidase staining, and red cell lysis have demonstrated that this antigen is not normally present on hematopoietic progenitor cells or on any other normal adult or fetal human tissue with the exception of the aforementioned subpopulation of B cells.

Further information regarding the CD5 marker is found in McMichael and Gotch, in *Leukocyte Typing III White Cell Differentiation Antigens* (Michael, ed. Oxford Press 1987). The CD5 molecule has also been described in the literature as reactive with immunoglobulins. See, e.g., Kernan et al., *J. Immunol.*, 33:137–146 (1984), which is incorporated herein by reference.

There are reports of attempted treatment of rheumatoid arthritis patients with monoclonal antibodies against CD4. See Horneff, et al. *Arthritis and Rheumatism* 34:2, 129–140 (February 1991); Goldberg, et al., *Arthritis and Rheumatism*, Abstract D115, 33:S153 (September 1990); Goldberg, *Journal of Autoimmunity*, 4:617–630 (1991); Choy, et al. *Scand. J. Immunol.* 36:291–298 (1992).

There are reports of attempted treatment of autoimmune disease, particularly rheumatoid arthritis, with an anti-CD5 monoclonal antibody. See Kirkham, et al., *British Journal of Rheumatology* 30:459–463 (1991); Kirkham, et al., *British Journal of Rheumatology* 30:88 (1991); Kirkham, et al., *Journal of Rheumatology* 19:1348–1352 (1992). There is also a report of an attempt to treat multiple sclerosis with an anti-T12 antibody. Hafler, et al. , *Neurology* 36:777–784 (1986).

As demonstrated by the foregoing, there exists a need in the art for a method of preparing antibody variable domains by identification of residues in mouse monoclonal variable region domains which may be modified without diminishing the native affinity of the domains for antigen while reducing their immunogenicity with respect to a heterologous species for use in the treatment of diseases.

SUMMARY OF THE INVENTION

The present invention provides methods for preparing a modified antibody variable domain useful for administration to humans by determining the amino acids of a subject antibody variable domain which may be modified without diminishing the native affinity of the domain for antigen while reducing its immmunogenicity with respect to a heterologous species. As used herein, the term "subject antibody variable domain" refers to the antibody upon which determinations are made. The method includes the following steps: determining the amino acid sequence of a subject light chain and a subject heavy chain of a subject antibody variable domain to be modified; aligning by homology the subject light and heavy chains with a plurality of human light and heavy chain amino acid sequences; identifying the amino acids in the subject light and heavy chain sequences which are least likely to diminish the native affinity of the subject variable domain for antigen while, at the same time, reducing its immunogenicity by selecting each amino acid which is not in an interface region of the subject antibody variable domain and which is not in a complementarity-determining region or in an antigen-binding region of the subject antibody variable domain, but which amino acid is in a position exposed to a solvent containing the antibody; changing each residue identified above which aligns with a highly or a moderately conserved residue in the plurality of human light and heavy chain amino acid sequences if said identified amino acid is different from the amino acid in the plurality.

Another group of sequences, such as those in FIGS. 1A and 1B may be used to determine an alignment from which the skilled artisan may determine appropriate changes to make.

The present invention provides a further method wherein the plurality of human light and heavy chain amino acid sequences is selected from the human consensus sequences in FIGS. 5A and 5B.

In general, human engineering according to the above methods may be used to treat various diseases against which monoclonal antibodies generally may be effective. However, humanized antibodies possess the additional advantage of reducing the immunogenic response in the treated patient.

The present invention also discloses products and pharmaceutical compositions useful in the treatment of a myriad human diseases. In particular, products prepared by the foregoing methods include a modified H65 mouse monoclonal variable domain. Additionally, DNA sequences encoding the modified H65 variable domain are provided.

Modified antibody variable domains which are products of the methods of the present invention may be used, inter alia, as components of various immunoglobulin molecules such as Fab, Fab', and F(ab')$_2$ domains, single chain antibodies, and Fv or single variable domains.

Immunoglobulin molecules comprising modified variable domains according to the invention are particularly suited for therapeutic administration to human by themselves or, for example, as components of immunoconjugates such as those described in co-pending, co-owned U.S. patent application Ser. No. 07/787,567 filed on Nov. 4, 1991.

The present invention also provides methods for treatment of autoimmune diseases, wherein animal models are predictive of the efficacy of treatment in humans. Finally, the present invention includes pharmaceutical compositions containing the humanized antibodies according to the invention are disclosed.

BRIEF DESCRIPTION OF THE DRAWING

FIGS. 1A and 1B are alignments of the amino acid sequences of the light and heavy chains, respectively, of four antibody variable domains [HYH (HYHEL-10 Fab-lysosyme complex), MCPC (IgA Fab MCPC603-phosphocholine complex), NEWM (Ig Fab' NEW) and KOL (IgG1 KOL)] by criteria of sequence and structural homology;

FIGS. 5A and 5B are alignments of the consensus amino acid sequences for the subgroups of light [hK1 (human kappa light chain subgroup 1), hK3 (human kappa light chain subgroup 3), hK2 (human kappa light chain subgroup 2), hL1 (human lambda light chain subgroup 1), hL2 (human lambda light chain subgroup 2), HL3 (human lambda light chain subgroup 3), hL6 (human lambda light chain subgroup 6), hK4 (human kappa light chain subgroup 4), hL4 (human lambda light chain subgroup 4) and hL5 (human lambda light chain subgroup 5] and heavy chains [hH3 (human heavy chain subgroup 3), hH1 (human heavy chain subgroup 1) and hH2 (human heavy chain subgroup 2)], respectively, of human antibody variable domains;

FIGS. 6A and 6B are alignments of human light chain consensus sequence hK1 with the actual (h65) and low-risk modified (prop) light chain sequences of the H65 mouse monoclonal antibody variable domain and of human heavy chain consensus sequence hH3 with the actual (h65) and modified (prop) heavy chain sequences of the H65 mouse monoclonal antibody variable domain, respectively;

FIGS. 7A and 7B are listings of the nucleotide sequences of the oligonucleotides utilized in the construction of the genes encoding modified V/J-regions of the light and heavy chains of the H65 mouse monoclonal antibody variable domain;

FIGS. 8A and 8B are listings of the nucleotide sequences of the genes encoding modified V/J-regions of the heavy and light chains, respectively, of the H65 mouse monoclonal antibody variable domain;

FIGS. 10A and 10B are alignments of human light chain consensus hK1 and heavy chain consensus hH1 with the light and heavy chain sequences, respectively, of the variable domain of human antibody EU, human antibody TAC, murine antibody TAC modified according to the present invention (prop) and murine antibody TAC modified according to a different method (Que);

FIG. 12 is a graph showing the effects of anti-Lyt-1 administration on the severity of collagen-induced arthritis in DBA/1J mice;

FIGS. 13A and 13B are depictions of human T cell recovery in spleen and blood, respectively from PBMC/SCID mice following treatment with H65 MoAb;

FIGS. 16A and 16B are alignments of human light chain consensus sequence hK1 with the actual (h65) and low and moderate risk modified (prop) light chain sequences of the H65 mouse monoclonal antibody variable domain and of human heavy chain consensus sequence hH3 with the actual (h65) and modified (prop) heavy chain sequences of the H65 mouse monoclonal antibody variable domain, respectively.

DETAILED DESCRIPTION

Methods according to the present invention include: (1) identification of the amino acid residues of an antibody variable domain which may be modified without diminishing the native affinity of the domain for antigen while reducing its immunogenicity with respect to a heterologous species; (2) the preparation of antibody variable domains having modifications at the identified residues which are useful for administration to heterologous species; and (3) use of the humanized antibodies of the invention in the treatment of autoimmune diseases in humans. The methods of the invention are based on a model of the antibody variable domain described herein which predicts the involvement of each amino acid in the structure of the domain.

Unlike other methods for humanization of antibodies, which advocate replacement of the entire classical antibody framework regions with those from a human antibody, the methods described herein introduce human residues into the variable domain of an antibody only in positions which are not critical for antigen-binding activity and which are likely to be exposed to immunogenicity-stimulating factors. The present methods are designed to retain sufficient natural internal structure of the variable domain so that the antigen-binding capacity of the modified domain is not diminished in comparison to the natural domain.

Data obtained from the analysis of amino acid sequences of antibody variable regions using the MacImdad (Molecular Applications Group, Stanford, Calif.) three-dimensional molecular modeling program, in conjunction with data obtained from previous theoretical studies of hypervariable region structure, and data obtained from the crystal structures of the HYH (HYHEL-10 Fab-lysosyme complex, Brookhaven structure "3HFM"), MCPC (IgA Fab MCPC603-phosphocholine complex, Brookhaven structure "2MCP"), NEWM (Ig Fab' NEW, Brookhaven structure "3FAB") and KOL (IgGl KOL, Brookhaven structure "2IG2") antibody variable domains from the Brookhaven database (Brookhaven National Laboratory, Upton, N.Y.), are utilized to develop the antibody variable domain model.

Figure 2:
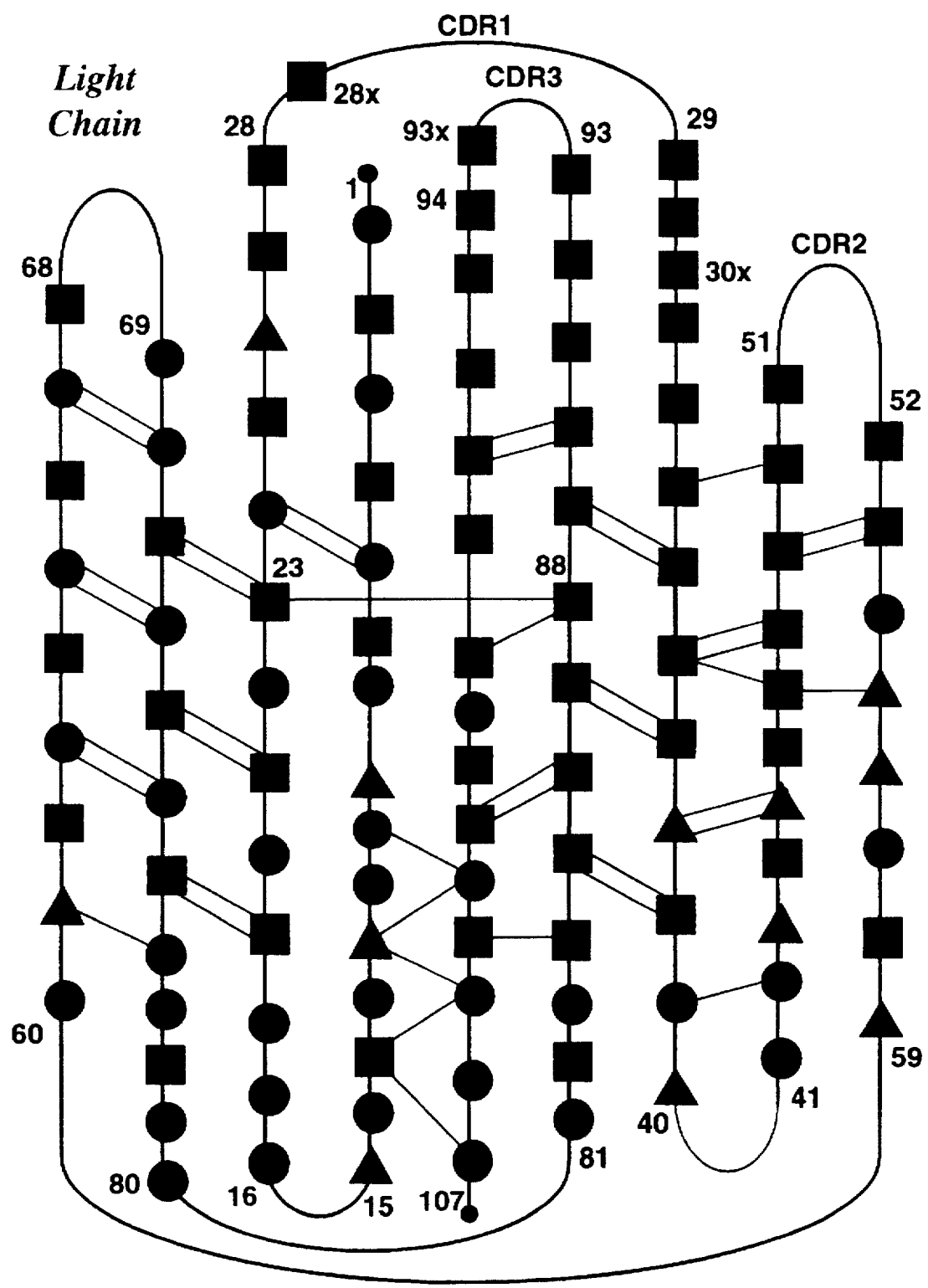
FIG. 2 is a schematic depiction of the structural relationships between the amino acid residues of the light chain of the variable domain.
Figure 3:
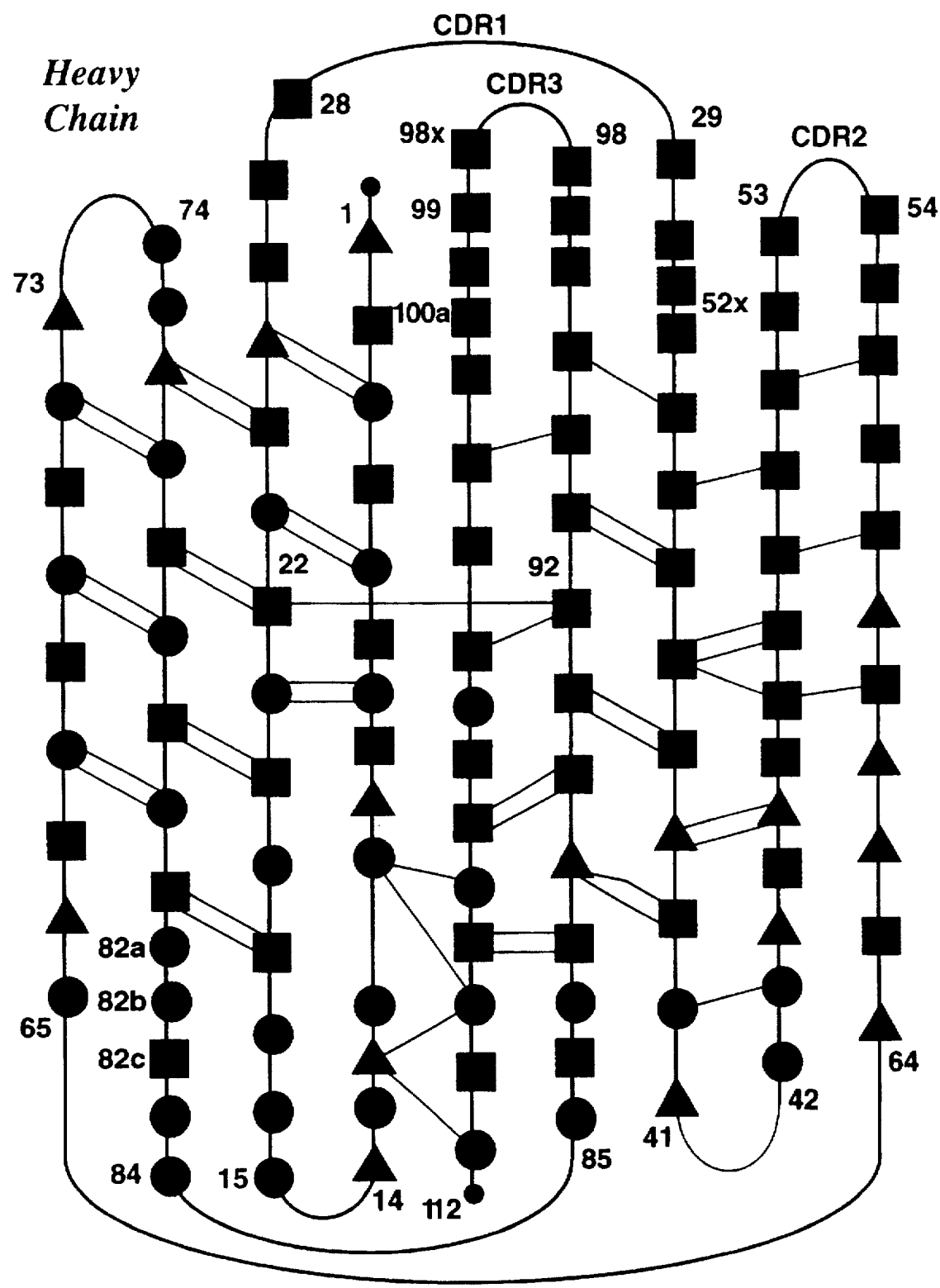
FIG. 3 is a schematic depiction of the structural relationships between the amino acid residues of the heavy chain of the variable domain.

FIGS. 1A and 1B provide the sequences of the four antibody variable domains which have been crystallized. The amino acid sequences of the light and heavy chains of HYH (SEQ ID Nos. 1 and 5, respectively), MCPC (SEQ ID Nos. 2 and 6, respectively), NEWM (SEQ ID Nos. 3 and 7, respectively) and KOL (SEQ ID Nos. 4 and 8, respectively) are shown, wherein the exclamation points "!" in the MCPC light chain sequence at position 30x, the MCPC heavy chain sequence at positions 52x and 98x, the NEWM light chain at position 30x, the KOL light chain at position 93x, and the KOL heavy chain sequence at position 98x, stand for the amino acid sequences NSGNQK (SEQ ID No. 9), NKG (SEQ ID No 10), GST (SEQ ID No 11), AG, SL and HGFCSSASC (SEQ ID No 12), respectively which are variations in the length of hypervariable loop sequences among the various antibodies. FIGS. 2 and 3 comprise depictions of the structure of the light and heavy chains, respectively, wherein each chain is displayed "unfolded" into, a flattened beta sheet structure so that interactions among the residues are easier to visualize. The strands of folded polypeptide chains are represented as thick vertical lines, connected by eight beta-turn loops. Three of the loops are identified as antigen-binding loops or CDRs, one is accessory to the loops, and the remaining four at the "bottom" of the variable domain are not involved in antigen binding. The amino and carboxy termini of the variable domain are symbolized by small black dots at the ends of the polypeptide chains. Each amino acid position is represented as either a circle, a triangle, or a square. The covalent disulfide bond between the two cysteines at positions 23 and 88 in the light chain and the covalent disulfide bond between positions 22 and 92 in the heavy chain are each shown as a thick horizontal line. All of the residues in each chain are shown on the map, including antigen-binding residues and framework residues. The amino acid positions are numbered according to Kabat et al., Sequences of Proteins of Immunological Interest, Fourth Edition, U.S. Department of Health and Human Services, Public Health Service, National Institutes of Health (1987), with the exception of those designated with a lower-case "x", which are variations in length of hypervariable loops which Kabat has numbered as "a,b,c,d . . . ". Solid slanted lines (either single or double) connecting pairs of residues which are adjacent in three-dimensional space but not in linear sequence, represent one or two hydrogen bonds between the mutually aligned amino nitrogens and carbonyl oxygens in the backbones of the residues.

The analysis of each amino acid position to determine whether the position influences antigen binding and/or is immunogenic was based upon the information in FIGS. 1A, 1B, 2 and 3, as well as the additional variable region structural information in the following paragraphs.

The basic structure of the antibody variable domain is strongly conserved. The variable domain is composed of a light chain (or subunit) and a heavy chain (or subunit), which are structurally homologous to each other and which are related by a pseudo-two-fold axis of rotational symmetry. At the "top" of the variable domain, the region farthest away from the constant domain, there are six antigen-binding loops which are built upon a larger structural framework region. The variable domain is functionally distinct from the constant domain, being connected only by two highly flexible chains and pivoting on both "ball-and-socket" joints formed by five amino acids in the heavy and light chains.

Each subunit, light or heavy, resembles a "sandwich" structure, composed of two layers of antiparallel beta pleated sheets with a propeller twist in three-dimensional space. Each amino acid chain folds back on itself repeatedly to create nine distinct strands. Three-and-one-half of these strands form the "outside" beta-sheet layer of each subunit and the other five-and-one-half form the "inside" layer. The various strands in each layer are extensively hydrogen-bonded to each other. The two beta-sheet layers within the subunit are held together by a single covalent disulfide bond and by numerous internal hydrophobic interactions. The sequences involved in bonding the strands of the subunits together are called "framework" sequences.

Certain amino acids, either in antigen-binding sequences or in framework sequences, do not actually bind antigen but are critical for determining the spatial conformation of those residues which do bind. Each antigen-binding loop requires a properly formed "platform" of buried residues, which provides a surface upon which the loop folds. One or more of the loop residues often will be buried in the platform as an "anchor" which restricts the conformational entropy of the loop and which determines the precise orientation of antigen-contacting sidechains. Thus, the shapes of the residues which make up the platform contribute to the ultimate shape of the antigen-binding loop and its affinity for specific antigens.

Figure 4:
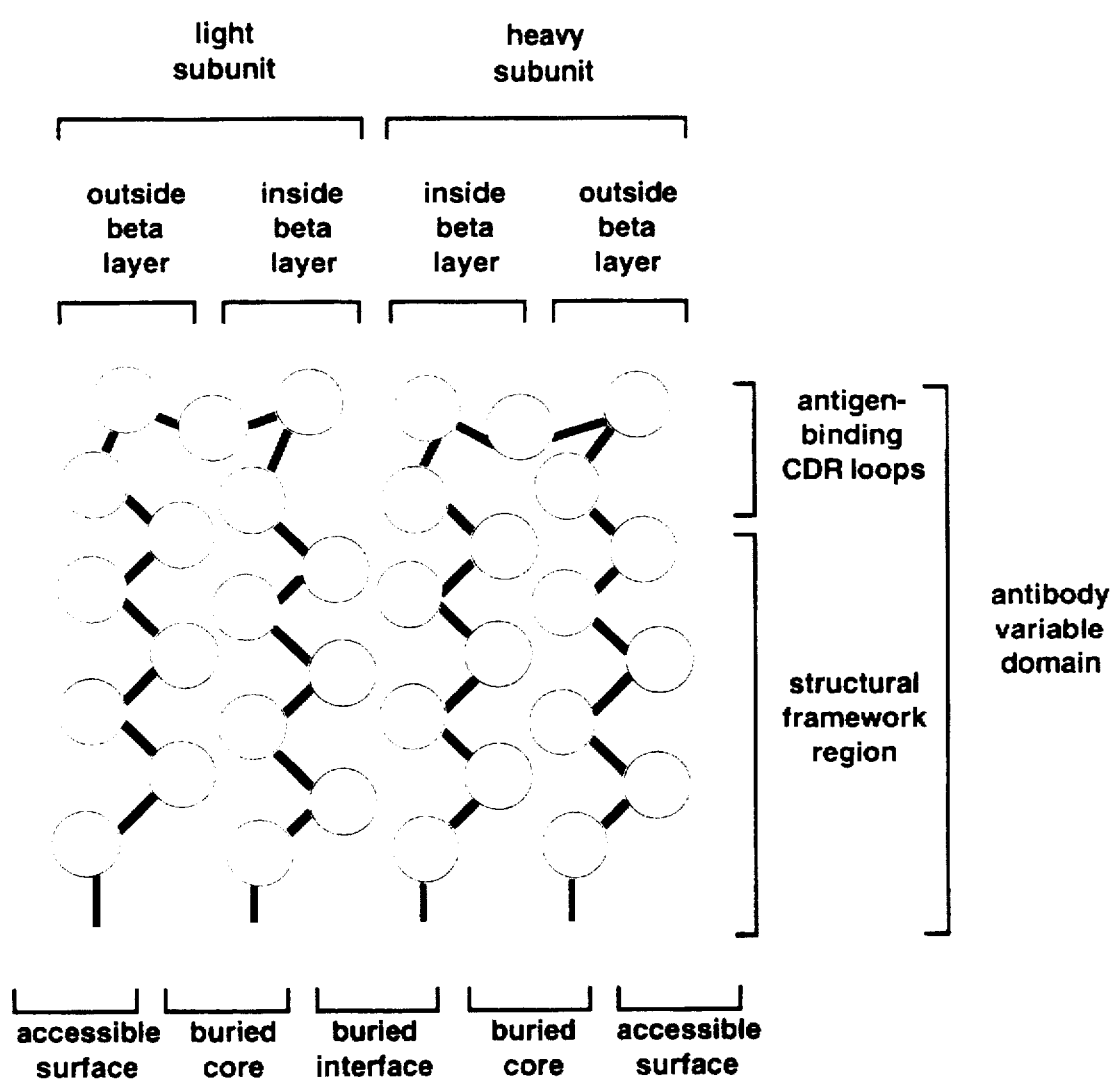
FIG. 4 is a schematic representation of an antibody variable domain.

Amino acid sidechains exist in various different chemical environments within the subunits. Some residues are exposed to the solvent on the outer accessible surface while other residues are buried in hydrophobic interactions within a subunit. Much of the immunoglobulin variable domain is constructed from antiparallel beta pleated sheets which create amphipathic surfaces, such that the "inside" surface is hydrophobic and the "outside" surface is hydrophilic. The outside is exposed to solvent, and therefore is also exposed to the humoral environment when the domain is in the circulatory system of an animal. Amino acid sidechains which are completely exposed to the solvent and which do not physically interact with other residues in the variable domain are likely to be immunogenic and are unlikely to have any structural importance within the immunoglobulin molecule. A highly schematic representation of the variable domain is shown in FIG. 4, wherein thick lines represent peptide bonds and shaded circles denote amino acid side chains.

The two subunits of antibody variable domains adhere to each other via a hydrophobic interface region which extends along the inside beta-sheet layer from the border of the variable domain with the constant domain to the antigen-binding loops. Amino acid side chains from both subunits interact to form a three-layered "herringbone" structure. Some of these interfacial residues are components of the antigen-binding loops, and thus have a direct effect upon binding affinity. Every residue in the interface is structurally important because the conformation of the binding regions is strongly influenced by changes in the conformation of the interface.

The foregoing data and information on the structure of antibody variable domains aids in a determination of whether a particular amino acid of any variable domain is likely to influence antigen binding or immunogenicity. The determination for each amino acid position is represented by a pair of symbols (e.g., + and +, in the lines labelled "bind" and "bury", respectively) in FIGS. 1A, 1B, (and also in FIGS. 5A, 5B, 6A, 6B, 10A and 10B). In each of these pairs, the first symbol relates to antigen binding, while the second symbol relates to immunogenicity and framework structure.

Tables 1, 2 and 3, below, set out the significance of the symbols and possible pairings.

TABLE 1

| FIRST SYMBOL IN PAIR (LIGAND BINDING) | |
|---|---|
| + | Little or no direct influence on antigen-binding loops, low risk if substituted |
| o | Indirectly involved in antigen-binding loop structure, moderate risk if changed |
| − | Directly involved in antigen-binding loop conformation or antigen contact, great risk if modified |

TABLE 2

| SECOND SYMBOL IN PAIR (IMMUNOGENICITY and STRUCTURE) | |
|---|---|
| + | Highly accessible to the solvent, high immunogenicity, low risk if substituted |
| o | Partially buried, moderate immunogenicity, moderate risk if altered |
| − | Completely buried in subunit's hydrophobic core, low immunogenicity, high risk if changed |
| = | Completely buried in the interface between subunits, low immunogenicity, high risk if modified. |

TABLE 3

| SIGNIFICANCE OF PAIRS | | |
|---|---|---|
| ++ | Low risk | Highly accessible to the solvent and high immunogenicity, but little or no effect on specific antigen binding |
| o+, +o, oo | Moderate risk | Slight immunogenicity or indirect involvement with antigen binding |
| any-or = | High risk | Buried within the subunit core/interface or strongly involved in antigen binding, but little no immunogenic potential |

The pairings set out in the Figures indicate that making mouse-to-human modifications at positions which have a pair of low risk symbols (++) (i.e., a symbol in the "bind" line and a symbol in the "bury" line corresponding to one position) results in a major reduction in therapeutic immunogenicity with little chance of affecting binding affinity. At the opposite end of the spectrum, modifying positions which have a pair of high risk symbols (—) may degrade or abolish binding activity with little or no actual reduction in therapeutic immunogenicity. There are 73 low risk positions in the variable domain (38 in the light chain and 35 in the heavy chain) which are indicated by circles in the lines labelled "risk" in FIGS. 1A, 1B, 5A, 5B, 6A, 6B, 10A and 10B. There are 29 moderate risk positions in the variable domain (12 in the light chain and 17 in the heavy chain) as indicated by the triangles in the lines labelled "risk" in FIGS. 1A, 1B, 5A, 5B, 6A, 6B, 10A, and 10B.

The results of the above analysis may be applied to consensus sequences for the different subgroups of antibody variable domains because the structural characteristics they represent are highly conserved, even among various species. FIGS. 5A and 5B thus set out and align the consensus sequences (derived from Kabat et al., supra) of the subgroups of light (hK1, SEQ ID NO: 13; hK3, SEQ ID NO: 14; hK2, SEQ ID NO: 15; hL1 SEQ ID NO: 16; hL2, SEQ ID NO: 17; hL3, SEQ ID NO: 18; hL6, SEQ ID NO: 19; hK4, SEQ ID NO: 20; hL4, SEQ ID NO: 21; and hL5, SEQ ID NO: 22) and heavy chains (hH3, SEQ ID NO: 23; hH1, SEQ ID NO: 24; and hH2, SEQ ID NO: 25) of antibody variable domains with the pairings representing the structural characteristics of each amino acid position, wherein the consensus sequences for the hL6, hK4, hL4, hL5 and hH2 subgroups were derived from less than twenty actual light or heavy chain sequences.

In the consensus sequences set out in FIGS. 5A and 5B, upper case amino acid designations indicate that the amino acid is present at that location in about 90% to about 100% of the known human sequences (excluding small incomplete fragments) of that subgroup (i.e., is "highly conserved"); whereas lower case amino acid designations indicate that the amino acid is present at that location in about 50% to about 90% of the known human sequences in that subgroup (i.e., is "moderately conserved"). A lower case "x" denotes conservation in less than about 50% of the known sequences in that subgroup (i.e., a "poorly conserved" position).

The information presented in FIGS. 5A and 5B on the relationship of a particular amino acid in a sequence of an antibody variable domain to the structure and antigen-binding capacity of the domain is sufficient to determine whether an amino acid is modifiable. Additional structural studies, such as those on which FIGS. 5A and 5B are based, are not required.

Thus, according to the present invention, FIGS. 5A and 5B may be used to prepare, for example, a modified mouse antibody variable domain that retains the affinity of the natural domain for antigen while exhibiting reduced immunogenicity in humans by the following steps. The amino acid sequences of both the light chain and the heavy chain from the mouse variable domain are first determined by techniques known in the art (e.g., by Edman degradation or by sequencing of a cDNA encoding the variable domain). Next, the consensus sequences set out in FIGS. 5A and 5B for human antibody variable regions are examined to identify both a light chain consensus and a heavy chain consensus sequence that are the most homologous to the particular mouse subunit sequences that are to be modified. The mouse sequences are aligned to the consensus human sequences based on homology either by sight or by using a commercially available computer program such as the PCGENE package (Intelligenetics, Mountain View, Calif.).

FIGS. 5A and 5B are then used again to identify all of the "low risk" or "moderate risk" positions at which the mouse sequence differs significantly from the chosen human consensus. The mouse amino acid residues at these low risk and moderate risk positions are candidates for modification. If the human consensus is strongly conserved at a given low risk or moderate risk position, the human residue may be substituted for the corresponding mouse residue. If the human consensus is poorly conserved at a given low risk or moderate risk position, the mouse residue is retained at that position. If the human consensus is moderately conserved at a specific position, the mouse residue is normally replaced with a human residue, unless the mouse residue occurs at that position in at least one of the sequences (e.g., in Kabat et al., supra) on which the human consensus sequence is based. If the mouse residue does occur at that position in a human sequence then the mouse residue may be retained.

Other criteria may be important to the determination of which identified residues of a variable region are to be modified. For example, since the side chain of proline is connected to both its α-carbon and its peptide nitrogen, free rotation is restricted around the carbon-nitrogen bond (the Ramachandran Φ angle). Therefore, wherever there is a proline in a sequence, the shape of the backbone is distorted and that distortion can influence other residues involved in antigen binding. The presence or absence of a proline residue at any point in the amino acid sequence is a structurally important feature. If the mouse sequence contains a proline at a certain location, it is likely that its presence is necessary for a proper backbone and framework conformation and proline is preferably retained. If the mouse sequence does not contain a proline at a location where the human consensus sequence has one, it is likely that substituting a proline in the mouse sequence would affect proper conformation of the sequence, therefore the mouse residue is preferably retained. Where a proline at a particular position involving proline is changed from mouse to human, such a change is considered to be at least moderate risk even if that position would otherwise be low risk.

Similarly, insertions and deletions in a mouse sequence, relative to a human consensus framework, are normally preserved intact. If the mouse sequence has an alteration in the length and spacing of the variable region backbone, it is likely that the alteration is necessary to provide a surface for proper folding of the antigen-binding loops. The alteration is preferably retained in a modified version of the sequence.

Residues participating in the interface between the light and heavy chains of a variable domain are also preferably left intact in a modified version. They are all designated high risk, with=symbols on the "bury" lines in FIGS. 1, 5, 6, 10. The side chains in the interface region are buried deep within the structure, so they are unlikely to elicit a therapeutic immunogenic response in a heterologous species.

Once a modified sequence has been designed, DNAs encoding the complete variable domain are synthesized [via oligonucleotide synthesis as described, for example, in Sinha et al., Nucleic Acids Res., 12, 4539–4557 (1984)], assembled [via PCR as described, for example in Innis, Ed., PCR Protocols, Academic Press (1990) and also in Better et al. J. Biol. Chem. 267, 16712–16118 (1992)], cloned and expressed [via standard procedures as described, for example, in Ausubel et al., Eds., Current Protocols in Molecular Biology, John Wiley & Sons, New York (1989) and also in Robinson et al., Hum. Antibod. Hybridomas, 2, 84–93 (1991)], and finally tested for specific antigen binding activity [via competition assay as described, for example, in Harlow et al., Eds., Antibodies: A Laboratory Manual, Chapter 14, Cold Spring Harbor Laboratory, Cold Spring Harbor (1988) and Munson et al., Anal. Biochem., 107, 220–239 (1980)].

Treatment of certain autoimmune diseases with immunotoxin conjugates is described in co-pending, commonly assigned U.S. patent application Ser. No. 07/759,297 filed Sep. 13, 1991, and Bernhard, et al., "Materials Comprising and Methods of Preparation and Use for Ribosome-Inactivating Proteins", a U.S. patent application filed Dec. 9, 1992, which are incorporated herein by reference. An immunoglobulin such as an anti-T-cell immunoglobulin may be conjugated to a cytotoxic molecule. The cytotoxic molecule to which the immunoglobulin is conjugated may be any of a number of toxins such as lectin A or a ricin A chain. The above-referenced '297 application also describes use of an anti-CD5 antibody conjugated to a ricin A chain providing an anti-T-cell immunotoxin.

A general description of various autoimmune diseases is found in The Autoimmune Diseases (Rose & Mackey, eds 1985). Autoimmune diseases may be characterized, inter alia, by abnormal immunological regulation which results in excessive B Cell activity and diminished, enhanced, or inappropriate T Cell activity. Such altered T cell activity may result in excessive production of autoantibodies. Although the autoimmune diseases are complex and diverse in their manifestations, they possess the common feature of an impaired immune system. Therapeutic depletion of circulating T cells through the administration of an anti-pan T cell immunoglobulin improves the clinical course and prognosis of patients with autoimmune disease. For anti-CD5 antibody therapy, the additional depletion of CD5 B cells may have a further beneficial effect since CD5 B cells have been implicated in some autoimmune diseases.

Once prepared, humanized antibodies are then useful in the treatment of autoimmune disease. In this regard, an anti-CD5 monoclonal antibody is presented as an example of a preferred embodiment of the invention. An example of an anti-pan T cell immunoglobulin is an CD5 antibody which is primarily reactive with a surface antigen of mature T cells, but is also reactive with 10–20% of mature B cells. Clinical data obtained using the anti-pan T cell immunoglobulin in models of autoimmune diseases in non-human animals are predictive of the effects of using such immunoglobulins as therapy against human autoimmune diseases.

For the purpose of the present invention, an immunoglobulin, such as an antibody, is "reactive" with or "binds to" an antigen if it interacts with the antigen forms an antigen-immunoglobulin complex. The antigen is generally a unique surface protein or marker. A most preferred marker is the CD5 antigen cluster.

The anti-pan T cell immunoglobulin may be obtained from a number of sources. It is reactive with most mature T cells or with both T cells and subsets of other lymphoid cells, such as B cells or natural killer (NK) cells. The immunoglobulin may be synthetic or recombinant, including genetically-engineered immunoglobulins such as chimeric immunoglobulins, humanized antibodies, hybrid antibodies, or derivatives of any of these.

Chimeric immunoglobulins, antibodies or peptides are comprised of fused portions from different species as a product of chimeric DNA. Chimeric DNA is recombinant DNA containing genetic material from more than one mammalian species. Chimeric immunoglobulins include one portion having an amino acid sequence derived from, or homologous to, a corresponding sequence in an immunoglobulin, antibody or peptide derived from a first gene source while the remaining segment of the chain(s) is homologous to corresponding sequences of another gene source. For example, a chimeric antibody peptide may comprise an antibody heavy chain with a murine variable region and a human constant region. The two gene sources will typically involve two species, but will occasionally involve different sources from one species.

Chimeric immunoglobulins, antibodies or peptides are typically produced using recombinant molecular and/or cellular techniques. Typically, chimeric antibodies have variable regions of both light and heavy chains that mimic the variable regions of antibodies derived from one mammalian species, while the constant portions are homologous to the sequences in antibodies derived from a second, different mammalian species.

The definition of chimeric antibody, however, is not limited to this example. A chimeric antibody is any antibody in which either or both of the heavy or light chains are composed of combinations of sequences mimicking the sequences in antibodies of different sources regardless of whether these sources are differing classes, differing antigen responses, or differing species of origin, and whether or not the fusion point is at the variable/constant boundary.

The terms "humanized," "human-like" or "human-engineered" refers to an immunoglobulin wherein the constant regions have at least about 80% or greater homology to human immunoglobulin, and wherein some of the nonhuman (i.e. murine) variable region amino acid residues may be modified to contain amino acid residues of human origin.

Humanized antibodies may be referred to as "reshaped" antibodies. Manipulation of the complementarity-determining regions (CDRs) is one means of manufacturing humanized antibodies. See, e.g., Jones, et al. Replacing the Complementarity—Determining Regions in a Human Antibody With Those From a Mouse, *Nature* 321:522–525 (1988); Riechmann, et al. Reshaping Human Antibodies For Therapy, *Nature* 332, 323–327 (1988). For a review article concerning chimeric and humanized antibodies, see Winter and Milstein, Man-Made Antibodies, *Nature* 349, 293–299 (1991).

Preferably, immunoglobulins of the present invention are monoclonal antibodies (hereinafter referred to as "MoAbs") of the IgM or IgG isotype of murine, human or other mammalian origin. Most preferably, the MoAb is reactive with the CD5 antigen found on both T and B cells. MoAbs of other animal species may be prepared using analogous non-human mammalian markers.

A variety of methods for producing MoAbs are known in the art. See, e.g., Goding, *Monoclonal Antibodies; Principles and practice* (2d ed., Academic Press 1986), which is incorporated herein by reference. Less preferred forms of immunoglobulins may be produced by methods well-known to those skilled in the art, such as by chromatographic purification of polyclonal sera to produce substantially monospecific antibody populations.

Monoclonal antibodies specifically directed against human CD5 antigen may be obtained by using combinations of immunogens and screening antigens which have only there human CD5 antigen in common or bay a screening assay designed to be specific for only anti-CD5 monoclonals. For example, production of monoclonal antibodies directed against CD5 may be accomplished by 1) immunization with human T cells expressing the CD5 antigen followed by screening of the resultant hybridomas for reactivity against a non-human cell line transfected with human CD5 (constructed in a manner similar to that described in Nishimura, et al., *Eur. J. Immunol.*, 18:747–753 (1988)); 2)immunization with a non-human cell line transfected with human CD5 followed by screening of the resultant hybridomas for reactivity against a human T cell line expressing the CD5 antigen; 3) immunization with human or non-human cell lines expressing human CD5 followed by screening of the resultant hybridomas for ability to block reactivity of existing anti-CD5 monoclonals with a human T cell line; 4) immunization with human or non-human cell lines expressing human CD5 followed by screening of the resultant hybridomas for reactivity with purified native or recombinant CD5 antigen; or 5) immunization with a recombinant derivative of the human CD5 antigen followed by screening of the resultant hybridomas for reactivity against a human T cell line expressing CD5.

A preferred monoclonal antibody for use in this invention is produced by hybridoma cell line XMMLY-H65 (H65) deposited with the American Type Culture Collection in Rockville, Md. (A.T.C.C.) and given the Accession No. HB9286. A preferred antibody is prepared as disclosed herein using the humanized forms of the murine H65 antibody.

The generation of human MoAbs to a human antigen is also known in the art. See, e.g., Koda and Glassy, *Hum. Antibod. Hybridomas*, 1(1) 15–22 (1990). Generation of such MoAbs may be difficult with conventional techniques. Thus, it may be desirable to modify the antigen binding regions of the non-human antibodies, e.g., the F(ab')₂ or hypervariable regions, to human constant regions (Fc) or framework regions by recombinant DNA techniques to produce substantially human molecules using general modification methods described in, for example, U.S. Pat. No. 4,816,397; and EP publications 173,494 and 239,400, which are incorporated herein by reference.

Alternatively, one may isolate DNA sequences which encode a human MoAb or portions thereof which specifically bind to the human T cell by screening a DNA library from human B cells according to the general protocols outlined by Huse et al., *Science* 246:1275–1281 (1989), Marks, et al., *J. Mol. Biol.* 222:581–597 (1991) which are incorporated herein by reference, and then cloning and amplifying the sequences which encode the antibody (or binding fragment) of the desired specificity.

In addition to the immunoglobulins specifically described herein, other "substantially homologous" modified immunoglobulins can be readily designed and manufactured utilizing various recombinant DNA techniques known to those skilled in the art. Modifications of the immunoglobulin genes may be readily accomplished by a variety of well-known techniques, such as site-directed mutagenesis. See, Gillman and Smith, Gene 8:81–97 (1979); Roberts, et al., Nature 328:731–734 (1987), both of which are incorporated herein by reference. Also, modifications which affect the binding affinity of the antibody may be selected using the general protocol outlined by McCafferty, et al., Nature 348:552–554 (1990), which is incorporated herein by reference.

In the present invention, an immunoglobulin, antibody, or peptide is specific for a T cell if it binds or is capable of binding T cells as determined by standard antibody-antigen or ligand-receptor assays. Examples of such assays include competitive assays, immunocytochemistry assays, saturation assays, or standard immunoassays such as ELISA, RIA and flow cytometric assays. This definition of specificity also applies to single heavy and/or light chains, CDRs, fusion proteins, or fragments of heavy and/or light chains, which bind T cells alone or are capable of binding T cells if properly incorporated into immunoglobulin conformation with complementary variable regions and constant regions as appropriate.

In some competition assays, the ability of an immunoglobulin, antibody, or peptide fragment to bind an antigen is determined by detecting the ability of the immunoglobulin, antibody, or peptide to compete with the binding of a compound known to bind the antigen. Numerous types of competitive assays are known and are discussed herein. Alternatively, assays which measure binding of a test compound in the absence of an inhibitor may also be used. For instance, the ability of a molecule or other compound to bind T cells can be detected by labelling the molecule of interest directly, or it may be unlabelled and detected indirectly using various sandwich assay formats. Numerous types of binding assays such as competitive binding assays are known. See, e.g., U.S. Pat. Nos. 3,376,110, 4,016,043; Harlow and Lane, *Antibodies: A Laboratory Manual*, Cold Spring Harbor Publications, N.Y. (1988), which are incorporated herein by reference.

Assays for measuring binding of a test compound to one component alone rather than using a competition assay are also available. For instance, immunoglobulins may be used to identify the presence of a T cell marker. Standard procedures for monoclonal antibody assays, such as ELISA, may be used see, Harlow and Lane, supra). For a review of various signal producing systems which may be used, see U.S. Pat. No. 4,391,904, which is incorporated herein by reference.

Other assay formats may involve the detection of the presence or absence of various physiological or chemical changes that result from an antigen-antibody interaction. See *Receptor-Effector Coupling—A Practical Approach*, (Hulme, ed., IRL Press, Oxford 1990), which is incorporated herein by reference.

Humanized antibodies of the present invention may be administered to patients having a disease having targetable cellular markers. Such disease include, but are not limited to , autoimmune diseases such as lupus (including systemic lupus erythematosus and lupus nephritis), scleroderma diseases (including lichen sclerosis, morphea and lichen planus), rheumatoid arthritis and the spondylarthropathies, thyroiditis, pemphigus vulgaris, diabetes mellitus type 1, progressive systemic sclerosis, aplastic anemia, myasthenia gravis, myositis including polymyositis and dermatomyositis, Sjogren's disease, collagen vascular disease, polyarteritis, inflammatory bowel disease (including Crohn's disease and ulcerative colitis), multiple sclerosis, psoriasis and primary biliary cirrhosis; diseases caused by viral infections; diseases caused by fungal infections; diseases caused by parasites; and the like.

Immunoglobulins, antibodies or peptides according to the invention may be administered to a patient either singly or in a cocktail containing two or more antibodies, other therapeutic agents, compositions, or the like, including, but not limited to, immunosuppressive agents, potentiators and side-effect relieving agents. Of particular interest are immunosuppressive agents useful in suppressing allergic or other undesired reactions of a host. Immunosuppressive agents include prednisone, prednisolone, dexamethasone, cyclophosphamide, cyclosporine, 6-mercaptopurine, methotrexate, azathioprine, and gamma globulin. All of these agents are administered in generally accepted efficacious dose ranges such as those disclosed in the *Physician's Desk Reference*, 41st Ed. (1987). In addition to immunosuppressive agents, other compounds such as an angiogenesis inhibitor may be administered with the anti-pan T immunoglobin. See Peacock, et al., *Arthritis and Rheum.* 35 (Suppl.), Abstract, for ACR meeting No. B141 (Sept. 1992).

In a preferred embodiment of the present invention, anti-pan T cell immunoglobulins may be formulated into various preparations such as injectable and topical forms. Parenteral formulations are preferred for use in the invention, most preferred is intramuscular (i.m.) or intravenous (i.v.) administration. The formulations containing therapeutically effective amounts of anti-pan T cell antibodies are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of from about 0.01 mg/kg of host body weight to about 10 mg/kg or more of host body weight.

Typically, the pharmaceutical compositions containing anti-pan T cell immunoglobulins are administered in a therapeutically effective dose in a range of from about 0.01 mg/kg to about 5 mg/kg body weight of the treated animal. A preferred dose range of the anti-pan T cell antibody is from about 0.05 mg/kg to about 2 mg/kg body weight of the treated animal. The immunoglobulin dose is administered over either a single day or several days by daily intravenous infusion. For example, for a patient weighing 70 kg, about 0.7 mg to about 700 mg per day is a preferred dose. A more preferred dose is from about 3.5 mg to about 140 mg per day.

Anti-pan T cell immunoglobulin may be administered systemically by injection intramuscularly, subcutaneously, intrathecally, intraperitoneally, into vascular spaces, or into joints (e.g., intraarticular injection at a dosage of greater than about 1 μg/cc joint fluid/day). The dose will be dependent upon the properties of the anti-pan T cell immunoglobulin employed, e.g., its activity and biological half-life, the concentration of anti-pan T cell antibody in the formulation, the site and rate of dosage, the clinical tolerance of the patient involved, the autoimmune disease afflicting the patient and the like as is well within the knowledge of the skilled artisan.

The anti-pan T cell immunoglobulin of the present invention may be administered in solution. The pH of the solution should be in the range of about pH 5.0 to about 9.5, preferably pH 6.5 to 7.5. The anti-pan T cell immunoglobulin or derivatives thereof should be in a solution having a pharmaceutically acceptable buffer, such as phosphate, tris (hydroxymethyl) aminomethane-HCl, or citrate and the like. Buffer concentrations should be in the range from about 1 to about 100 mM. A solution containing anti-pan T cell immunoglobulin may also contain a salt, such as sodium chloride or potassium chloride in a concentration from about 50 to about 150 mM. An effective amount of a stabilizing agent such as albumin, a globulin, a detergent, a gelatin, a protamine, or a salt of protamine may also be included and may be added to a solution containing anti-pan T cell immunoglobulin or to the composition from which the solution is prepared. Systemic administration of anti-pan T cell immunoglobulin is typically made every two to three days or once a week if a chimeric or humanized form is used. Alternatively, daily administration is useful. Usually administration is by either intramuscular injection or intravascular infusion.

Alternatively, anti-pan T cell immunoglobulin is formulated into topical preparations for local therapy by including a therapeutically effective concentration of anti-pan T cell immunoglobulin in a dermatological vehicle. Topical preparations may be useful to treat skin lesions such as psoriasis and dermatitis associated with lupus. The amount of anti-pan T cell immunoglobulin to be administered, and the anti-pan T cell immunoglobulin concentration in the topical formulations, will depend upon the vehicle selected, the clinical condition of the patient, the systemic toxicity and the stability of the anti-pan T cell immunoglobulin in the formulation. Thus, the physician will necessarily employ the appropriate preparation containing the appropriate concentration of anti-pan T cell immunoglobulin in the formulation, as well as the amount of formulation administered depending upon clinical experience with the patient in question or with similar patients.

The concentration of anti-pan T cell immunoglobulin for topical formulations is in the range from about 0.1 mg/ml to about 25 mg/ml. Typically, the concentration of anti-pan T cell immunoglobulin for topical formulations is in the range from about 1 mg/ml to about 20 mg/ml. Solid dispersions of anti-pan T cell immunoglobulin as well as solubilized preparations may be used. Thus, the precise concentration to be used in the vehicle may be subject to modest experimental manipulation in order to optimize the therapeutic response. Greater than about 10 mg of anti-pan T cell immunoglobulin/100 grams of vehicle may be useful with 1% w/w hydrogel vehicles in the treatment of skin inflammation. Suitable vehicles, in addition to gels, are oil-in-water or water-in-oil emulsions using mineral oils, petrolatum, and the like.

Anti-pan T cell immunoglobulin may be optionally administered topically by the use of a transdermal therapeutic system (Barry, *Dermatological Formulations*, p. 181 (1983)). While such topical delivery systems have been designed largely for transdermal administration of low molecular weight drugs, by definition they are capable of percutaneous delivery. They may be readily adapted to administration of anti-pan T cell immunoglobulin or derivatives thereof and associated therapeutic proteins by appropriate selection of the rate-controlling microporous membrane.

Preparations of anti-pan T cell immunoglobulin either for systemic or local delivery may be employed and may contain excipients as described above for parenteral administration and other excipients used in a topical preparation such as cosolvents, surfactants, oils, humectants, emollients, preservatives, stabilizers and antioxidants. Any pharmacologically acceptable buffer may be used, e.g., tris or phosphate buffers.

Administration may also be intranasal or by other nonparenteral routes. Anti-pan T cell immunoglobulin may also be administered via microspheres, liposomes or other microparticulate delivery systems placed in certain tissues including blood.

Anti-pan T cell immunoglobulin may also be administered by aerosol to achieve localized delivery to the lungs. This is accomplished by preparing an aqueous aerosol or liposomal preparation. A nonaqueous (e.g., fluorocarbon propellent) suspension may be used. Sonic nebulizers preferably are used in preparing aerosols. Sonic nebulizers minimize exposing the anti-pan T cell antibody or derivatives thereof to shear, which can result in degradation of anti-pan T cell immunoglobulin.

Ordinarily, an aqueous aerosol is made by formulating an aqueous solution or suspension of anti-pan T cell immunoglobulin together with conventional pharmaceutically acceptable carriers and stabilizers. The carriers and stabilizers will vary depending upon the requirements for the particular anti-pan T cell immunoglobulin, but typically include nonionic surfactants (Tweens, Pluronics, or polyethylene glycol), innocuous proteins such as serum albumin, sorbitan esters, oleic acid, lecithin, amino acids such as glycine, buffers, salts, sugars, or sugar alcohols. The formulations are sterile. Aerosols generally may be prepared from isotonic solutions.

Each of the foregoing methods are illustrated by way of the following examples, which are not to be construed as limiting the invention. All references cited herein are incorporated by reference.

EXAMPLES

Example 1

A. Identification of Low Risk Residues in A Mouse Variable Domain

A method of the present invention was utilized to prepare modified antibody variable domains by identifying low risk residues in a mouse monoclonal antibody variable domain, designated H65, which may be modified without diminishing the native affinity of the domain for antigen while still reducing its immunogenicity with respect to humans.

The light and heavy chains of the variable domain of H65 were determined to most closely resemble the consensus sequences of subgroup 1 ("hK1") of the human kappa chains and subgroup 3 ("hH3") of the human heavy chains, respectively. The H65 V/J-segments of the light and heavy chain sequences are aligned with the two human subgroup consensus sequences in FIGS. 6A and 6B. The H65 sequences are also contained in SEQ ID Nos. 26 and 28.

In FIGS. 6A and 6B, upper and lower case letters denote the degree of conservation at any given position. For example, an "A" indicates that alanine is present at that position in about 90% to about 100% of the known human sequences of that subgroup (excluding small, incomplete fragments); whereas an "a" indicates that alanine is present only about 50% to about 90% of the time at that position in known human sequences of that subgroup. A lower case "x" indicates conservation of the amino acid at that position less than about 50% of the time.

The line labelled "bind" shows which residues directly affect (−) or do not directly affect (+) antigen binding of CDR loops. The "bury" line indicates exposed (+), buried (−), or interfacial (=) residues. On either the "bind" or "bury" line, a "0" indicates a residue of intermediate significance in terms of antigen binding or placement of the residue, respectively.

FIGS. 6A and 6B reveal that the mouse H65 sequences differ from the human consensus sequences with which they are aligned at a total of 94 positions. Sixty-nine of these differences occur at moderate-risk (15 positions) or high risk (54 positions) positions suggesting that the mouse residue at that position may be important for the function of the antibody. The "M/H" line of FIG. 6 specifically indicates which positions differ between the two pairs of aligned sequences. Based on the considerations of the level of risk and the degree of conservation of the human residue at each position presented in the foregoing paragraphs, those residues in the H65 sequences designated M or m in the M/H line are identified as residues to be kept "mouse" in a humanized sequence, while those designated H or h are identified as residues to be changed to "human."

Twenty-five differences occur at low risk positions at which the mouse and human sequences differ. At thirteen of those positions (designated "H" on the M/H lines of FIG. 6) the mouse residue aligns with a human consensus amino acid which is highly conserved. Therefore, the mouse residue at that position is identified as one to be changed to the conserved human residue.

At four low risk positions (designated "m") in which the mouse and the human sequences differ, the mouse residue aligns with a human consensus amino acid which is moderately conserved. However, since the mouse residue is found at that position in other actual sequences of human antibodies (in Kabat's sequences of Proteins of Immunoglobulin Interest), the positions are identified as ones to be kept "mouse." At seven low risk positions (designated "h"), the mouse residue aligns with a human consensus amino acid which is moderately conserved but the mouse residue is not found at that position in an actual human antibody sequence in the Kabat book. Therefore, those positions are identified as ones to be changed to "human."

At one low risk position (designated "m") in which the mouse and human sequences differ, the mouse residue aligns with a human consensus amino acid which is poorly conserved. Therefore, that position is identified as one to be kept "mouse."

The "prop" lines of FIG. 6 set out the sequences of the light and heavy chains of the H65 antibody variable domain in which the residues identified by the methods of the present invention as those which may be modified without diminishing the native affinity of the H65 variable domain for CD5 are changed to human residues. Thus, the "prop" lines of FIGS. 6A and 6B set out the amino acid sequences of humanized light (SEQ ID NO: 27) and heavy chains (SEQ ID NO: 29) of the H65 antibody variable domain.

Example 2

A. Synthesis of H65 V/J Segments of light and heavy chain

Based on the low risk humanized amino acid sequences of the V/J-segments of the light and heavy chains of the H65 antibody variable domain described in Example 1, synthetic genes for heavy and light chain V/J-segments of H65 were synthesized. The humanized amino acid sequences were reverse-translated with the PCGENE package (Intelligenetics, Mountain View, Calif.). Amino acid codons for each position were chosen which were identical to the mouse codon at positions where the mouse amino acid residue was maintained, or which matched as closely as possible a codon in a native antibody gene based on those gene sequences published in Kabat et al. supra. For expression of humanized whole antibody in mammalian cells, polynucleotides encoding the native mouse leader sequences were included as part of the humanized genes. Each gene, heavy or light, was assembled from six overlapping oligonucleotides and amplified by PCR. Each oligonucleotide was synthesized with a Cyclone Model 8400 DNA Synthesizer (Milligen/Biosearch, Burlington, Mass.). Restriction sites were introduced into the amplified DNA segments for cloning into the final expression vectors for antibody genes (heavy or light). A SalI restriction site was introduced into each V-region upstream of the initiation codon, ATG. A BstEII restriction site was introduced into the 3'-end of the heavy chain J-region, while a HindIII site was introduced into the 3'-end of the light chain J-region.

B. Construction of the Gene Encoding the Humanized H65 Heavy Chain Variable Region The humanized V- and J-segments of the heavy chain were assembled from six oligonucleotides, HUH-G1, HUH-G2, HUH-G3, HUH-G4, HUH-G5, and HUH-G6, the sequences of which are contained in FIG. 7B and in SEQ ID Nos. 36 to 41, respectively. The oligonucleotides were amplified with PCR primers H65G-2S and H65-G2 (SEQ ID Nos. 42 and 43, respectively). Oligonucleotides greater than 50 bp in length were purified on a 15% polyacrylamide gel in the presence of 25% urea. DNA strand extension and DNA amplification was accomplished with a Taq polymerase and the GeneAmp Kit used according to the manufacturer's instructions (Perkin-Elmer Cetus, Germany). Oligonucleotides containing the synthetic humanized antibody gene were mixed in pairs (HUH-G1+HUH-G2, HUH-G3+HUH-G4, and HUH-G5+HUH-G6) in 100 μl reactions with 1 μg of each DNA, 2.5 U Taq polymerase, 50 mM KCl, 10 mM TRIS-Cl pH 8.3, 1.5 mM MgCl$_2$, and 200 uM each dNTP. The tube was incubated in a Coy TempCycler for 1 minute at 94° C., 2 minutes at 55° C. and 20 minutes at 72° C. A portion of each reaction product (40 μl) was mixed in pairs (HUH-G1,2+HUH-G3,4; HUH-G3,4+HUH-G5,6), 2.5 U Taq was added and the tubes were re-incubated at 94° C. for 1 minute, 55° C. for 2 minutes and 72° C. for 20 minutes. The heavy chain gene was then assembled by mixing an equal amount of the HUH-G1,2,3,4 reaction product with the HUH-G3,4,5,6 reaction product and bringing the volume to 100 μl of 2.5 U Taq, 50 mM KCl, 10 mM TRIS-Cl pH 8.3, 1.5 mM MgCl$_2$, 200 uM each dNTP, and 0.5 μg of each amplification primer H65G-2S and H65-G2. The reaction was overlaid with mineral oil, and the cycle profile used for amplification was: denaturation 94° C. for 1 minute, annealing 55° C. for 2 minutes, and primer extension at 72° C. for 3 minutes. Primer extension was carried out for 30 cycles. The DNA sequence of the assembled V/J-region is contained in FIG. 8A and in SEQ ID NO: 46. The assembled V/J-region was cut with SalI and BstEII, purified by electrophoresis on an agarose gel, and assembled into a heavy chain expression vector, pING4612, which is similar to that described for heavy chain expression in Robinson et al., *Hum. Antib. Hybridomas*, 2, 84 (1991) and described in detail in co-pending, co-owned U.S. patent application Ser. No. 07/659,409 filed on Sep. 6, 1989, which is incorporated herein by reference.

C. Construction of the Gene Encoding the Humanized H65 Light Chain Variable Region The humanized V- and J-segments of the light chain were also assembled from six oligonucleotides, $H65K-1, HUH- K1, HUH-K2, HUH-K3, HUH-K4 and HUH-K5, the sequences of which are contained in FIG. 7 and in SEQ ID NOs. 30 to 35, respectively. The oligonucleotides were amplified with PCR primers H65K-2S and JK1-HindIII (SEQ ID NOs. 44 and 45, respectively). Oligonucleotides containing the synthetic humanized antibody gene were mixed in pairs ($H65K-K1+HUH-K1, HUH-K2+HUH-K3, and HUH-K4+HUH-K5) and incubated as described above for the heavy chain. A portion of each reaction product (40 µl) was mixed in pairs ($H65K-l/HUH-K1+HUH-K2,3; HUH-K2,3+HUH-K4,5) and treated as above. The light chain gene was then assembled by amplifying the full length gene with PCR primers H65K-2S and JK1-HindIII as outlined above for the heavy chain. The DNA sequence of the assembled V/J-region is contained in FIG. 8B and in SEQ ID NO. 47. The assembled V/J-region was cut with SalI and HindIII, purified by electrophoresis on an agarose gel, and assembled into a light chain antibody expression vector, pING4614 similar to those described for light chain expression in Robinson et al., supra, and in U.S. patent application Ser. No. 07/659,409, supra.

D. Transient Expression of Humanized H65 IaG

Expression vectors containing the humanized H65 light chain and heavy chain sequences under the control of the Abelson Leukemia virus LTR promoter (described in Robinson et al., supra, and in U.S. patent application Ser. No. 07/659,409, supra) and 3' untranslated regions from human gamma-1 (for heavy chain) and mouse kappa (for light chain) were transfected by lipofection into a CHO-K1 strain which expresses the SV40 T antigen. Following treatment with lipofection reagent (Bethesda Research Labs, Gaithersburg, Md.) plus DNA for 5 hours at 37° C., Ham's F12 media containing fetal bovine serum (FBS, final FBS conc.=10%) was added and the cells were incubated for an additional 48 hours. Following this incubation period, the FBS-supplemented media was removed and replaced with serum-free media (HB-CHO) (Irvine Scientific, Irvine, Calif.) and the cells were incubated for an additional 7 days. As a control, the CHO-K1 cells were also transfected with chimeric H65 light chain and heavy chain (each consisting of unmodified mouse V/J-segments fused to a human C-segment) in expression vectors similar to those described above. Following incubation, the supernatants were collected and tested by ELISA for the presence of secreted IgG. All of the supernatants contained about 0.03–0.06 pg/ml IgG.

Example 3

The H65 antibody modified according to the methods of the present invention was tested to determine whether it retained native affinity for antigen. Its binding capability was compared to that of a chimeric H65 IgG antibody (consisting of the chimeric H65 light chain and heavy chain described in Example 2) which has the same affinity for CD5 as unmodified H65 mouse antibody.

A. Preparation of Humanized and Chimeric H65 IaG for Competition Binding

The humanized H65 (hH65) and chimeric H65 IgG (cH65) from transient transfections described above were concentrated from 4 ml to a final volume of 100 µl by centrifugation using a Centricon 30 (Amicon, Amicon Division of W. R. Grace and Co., Beverley, Mass.) at 4° C. Both hH65 and cH65 concentrates were then washed once with 1.0 ml of phosphate buffered saline (PBS), pH 7.2 and reconcentrated to approximately 100 µl. As a control, HB-CHO culture media alone (CM) or media supplemented with purified cH65 (CM+cH65) was concentrated in a similar manner. The final concentrations of hH65 and cH65 were determined by ELISA (anti-human Kappa pre-coat, peroxidase-labelled anti-human gamma for detection) using chimeric IgG as a standard.

B. Radiolabelling of cH65 IgG

20 µg of purified cH65 IgG was iodinated (1 mCi of $Na^{125}I$, Amersham, Arlington Heights, Ill.) using lactoperoxidase beads (Enzymobeads, BioRad Laboratories, Richmond, Calif.) in PBS. Iodination was allowed to proceed for 45 minutes at 23° C. $^{125}I$-cH65 IgG was purified from unbound $^{125}I$ by gel filtration using a Sephadex G-25-80 column. Concentration and specific activity was determined by measuring the TCA-precipitated counts before and after purification.

C. Competitive Binding of hH65 for cH65 IgG

Molt4-M cells, which express CD5 on their surface, were plated into 96 well V-bottom plates at a density of $3 \times 10^5$ cells per well and pelleted by centrifugation. The medium was decanted, and 100 µl of purified cH65 IgG at final concentrations from 200 nM to 0.0017 nM (diluted in 3-fold steps) in "BHD" [DMEM (Dulbecco's Modified Eagle's Medium)+1% BSA+10 mM Hepes, pH 7.2] (BHD) was added to each well, followed by 100 µl of $^{125}I$-cH65 IgG (final concentration=0.1 nM) in BHD. For single point determinations, 50–100 µl of the Centricon® concentrates were added to the wells as follows: hH65 (final concentration=0.54 nM), cH65 (final concentration=0.22 nM), CM+purified cH65 IgG (final concentration=30 nM) and CM alone. These were followed by addition of $^{125}I$-cH65 IgG (final concentration =0.1 nM). Binding was allowed to proceed for 5 hours at 4° C. At the end of 5 hours, binding was terminated by three washes with ice cold BHD using centrifugation to pellet cells. Radioactivity was determined by solubilizing bound $^{125}I$-cH65 IgG with 1N NaOH and counting in a Beckman Gamma 8000 (Beckman Instruments, Fullerton, Calif.).

Figure 9:
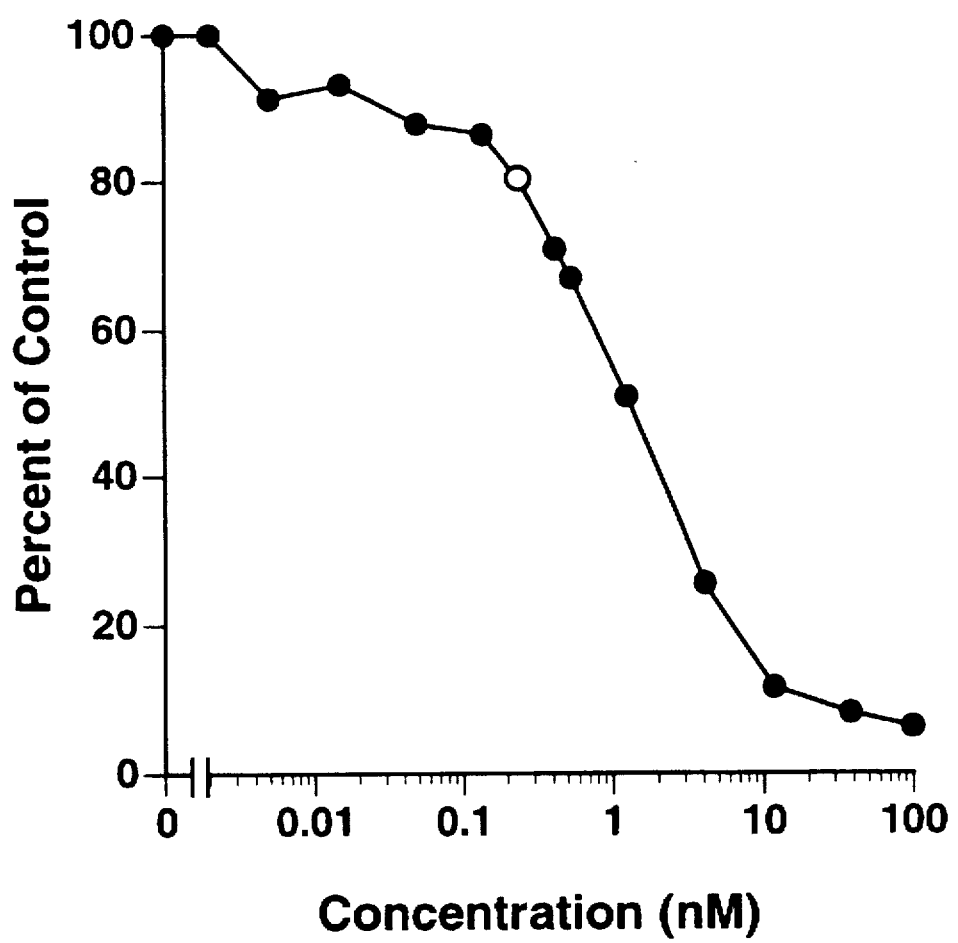
FIG. 9 is a graph of the results of a competitive binding assay showing that the H65 antibody variable domain modified by a method according to the present invention retains the antigen-binding capability of the natural H65 antibody variable region.

Purified cH65 IgG effectively displaced $^{125}I$-cH65 IgG binding with an $ED_{50}$ of approximately 1.0 nM as shown in FIG. 9, wherein open circles indicate cH65, shaded squares indicate hH65 and shaded triangles indicate CM+purified cH65. The hH65 was as effective in displacing $^{125}I$-cH65 IgG as were purified cH65 and CM+purified cH65 IgG, at their respective concentrations. No competition was observed with CM as expected. These results demonstrate that the low-risk changes made in the course of modification of hH65 did not diminish the binding affinity of this antibody for the CD5 antigen.

Example 4

The method of the present invention for preparing modified antibody variable domains by identifying modifiable amino acids was applied to the anti-TAC antibody variable domain sequence [SEQ ID Nos. 49 (light chain) and 53 (heavy chain)] and the resulting modified sequence is compared to the humanized anti-TAC antibody sequence [SEQ ID Nos. 51 (light chain) and 55 (heavy chain)] described in Queen et al., supra.

The results are shown in FIGS. 10A and 10B. The sequence modified according to the present invention [SEQ ID Nos. 50 (light chain) and 54 (heavy chain)] is shown on the lines labelled "prop." and the Queen humanized sequence is shown on lines labelled "Que." Modifications to the Queen humanized sequence were based on the human EU antibody sequence [SEQ ID Nos. 48 (light chain) and 52 (heavy chain)]. The comparison reveals many differences between the proposed sequence generated by the methods of the present invention and the Queen humanized sequence. The differences which are the most likely to affect binding activity of their humanized antibody are positions 4 (L vs. M), 15 (P vs. V), 36 (F vs. Y), 47 (W vs. L), 71 (Y vs. F), and 80 (A vs. P) in the light chain, as well as position 69 (L vs. I) in the heavy chain.

Example 5

Active Modified Antibodies May Be Evolved Toward Human

If it is desirable to humanize an antibody variable domain beyond the changes identified above, further, higher-risk changes may be made to evolve the domain.

Higher-risk residues may be changed in a round of mutagenesis subsequent to the low risk changes, in smaller groups, so that deleterious mutations may be identified quickly and corrected before binding activity is abolished. (Low risk changes can be made all at once, with little fear of abolishing activity.)

For example, because in the three-dimensional model of each subunit, framework 1 and framework 3 (F1 and F3 in FIGS. 2 and 3) form semi-independent loops on the surface of the subunit, the moderate or high risk mutations may therefore be divided into four groups (consisting of F1 and F3 in the light subunit and F1 and F3 in the heavy subunit). Four different constructs may be made, each containing higher-risk "human" mutations in only one framework region with the other three frameworks left completely "mouse," and assayed for activity. This technique avoids the dilemma raised by other humanization methods in which all higher-risk changes are made at once, making it difficult to determine which of the many amino acid changes is responsible for affecting antigen-binding activity. The creation of antibodies according to the invention which possess moderate risk changes are described below.

Example 6

Identification of Moderate Risk Residues in Mouse Variable Domain

The human consensus sequences in which moderate risk residues are converted from mouse residues to human residues are represented in FIGS. 16A and 16B as lines labelled hK1 (i.e., subgroup I of the human kappa chain) and hH3 (i.e., subgroup 3 of the human heavy chain). Symbols in this Figure, for conservation and for risk are used in accordance with FIGS. 6A and 6B.

In the line labelled "mod", a dot (.) represents a residue which may be mutated from "mouse" to "human" at moderate risk. There are 29 such moderate risk positions.

The mouse residue matches the human consensus residue more than 50% of the time at 131 positions (102 positions match 90%–100% and 29 positions match 50% to 90%). These positions were not changed.

The lines labelled M/H in FIGS. 16A and 16B indicate the 91 positions which differed significantly between the mouse and human sequences (i.e., where the human sequences have the mouse residue less than 50% of the time). Moderate risk positions, designated m in the M/H line, were kept "mouse"; whereas those designated H or h were changed to human.

The 25 low risk positions which were already human-like or which were previously humanized (as described supra in Example 1) are designated "·" in the M/H line. Finally, the 54 high risk positions in which the mouse and human residues did not match are designated M and are kept "mouse".

Fifteen differences occur at moderate risk positions at which the mouse and human sequences differ. At ten of those positions (designated "H" on the M/H lines of FIG. 6) the mouse residue aligns with a human consensus amino acid which is highly conserved. Therefore, the mouse residue at that position is identified as one to be changed to the conserved human residue.

At moderate risk positions (designated "m") in which the mouse and the human sequences differ, the mouse residue aligns with a human consensus amino acid which is moderately conserved. However, since the mouse residue is found at that position in other actual sequences of human antibodies (in Kabat's sequences of Proteins of Immunoglobulin Interest, the positions are identified as ones to be kept "mouse." Although there are no such positions in this particular sequence, such positions may occur in other antibodies.

At four moderate risk positions (designated "h"), the mouse residue aligns with a human consensus amino acid which is moderately conserved but the mouse residue is not found at that position in an actual human antibody sequence in Kabat, et al. *Sequences of Proteins of Immunoglobulin Interest*, supra. Therefore, that position is identified as ones to be changed to "human."

At one moderate risk position (designated "m") in which the mouse and human sequences differ, the mouse residue aligns with a human consensus amino acid which is poorly conserved. Therefore, that position is identified as one to be kept "mouse."

The humanized H65 heavy chain containing the moderate risk residues was assembled by a strategy similar to that for the low risk residues. The moderate-risk expression vector was assembled from intermediate vectors. The six oligonucleotide sequences (oligos), disclosed in FIG. 7B and labelled HUH-G11, HUH-G12, HUH-G3, HUH-G4, HUH-G5, and HUH-G6 (the sequences of HUH-G11 and HUH-G12 are set out in SEQ ID Nos. 56 and 57) were assembled by PCR. Oligonucleotides containing the synthetic humanized antibody gene were mixed in pairs (HUH-GI1+HUH-G12, HUH-G3+HUH-G4, and HUH-G5+HUH-G6) in a 100 μl reaction with 1 μg of each DNA and filled in as described above. A portion of each reaction product was mixed in pairs (HUH-G11, 12+HUH-G3, 4; HUH-G3, 4+HUH-G5, 6), 2.5 U Taq was added and samples were reincubated as described above. The in-J-region was assembled by mixing equal amounts of the HUH-Gi1, 12, 3, 4 reaction product with the HUH-G3, 4, 5, 6 product, followed by PCR with 0.5 ug of primers H65G-2S and H65-G2 as described above. The reaction product was cut with SalI and BstEII and cloned into the expression vector, similar to that described for heavy chain in Robinson et al., *Hum. Antibod. Hybridomas* 2:84 (1991), generating pING4617. That plasmid was sequenced with Sequenase (USB, Cleveland), revealing that two residues were altered (a G-A at position 288 and a A-T at position 312, numbered from the beginning of the leader sequence). The correct variable region was restored by substitution of this region from pING4612, generating the expected V-region sequence in pING4619.

An intermediate vector containing the other moderate-risk changes was constructed by PCR assembly of the oligos HUH-G13, HUH-G14, HUH-G15, and HUH-G16 (FIG. 7A and SEQ ID Nos: 58–61). Oligos HUH-G13+HUH-G14 and HUH-G15+HUH-G16 were mixed and filled in with Vent polymerase (New England Biotabs) in a reaction containing 10 mM KCl, 20 mM TRIS pH 8.8, 10 mM $(NH_4)_2SO_2$, 2 mM $MgSO_4$, 0.1% Triton X-100, 100 ng/ml BSA, 200 uM of each dNTP, and 2 units of Vent polymerase in a total volume of 100 µl. The reaction mix was incubated at 94° C. for 1 minute, followed by 2 minutes at 50° C. and 20 minutes at 72° C. The reaction products (40 µl) were mixed and amplified with the oligonucleotides H65-G13 and H65-G2 with Vent polymerase in the same reaction buffer and amplified for 25 cycles with denaturation at 94° C. for 1 minute, annealing at 50° C. for 2 minutes and polymerization at 72° C. for 3-minutes. The reaction product was treated with T4 polymerase and then digested with AccI. The 274 base pair (bp) fragment was purified on an agarose gel and ligated along with the 141 bp SalI to AccI fragment from pING4619 into pUC18 cut with SalI and SmaI to generate pING4620. pING4620 contains the entire signal sequence, V-region, and J-region of the moderate-risk H65 heavy chain.

The final expression vector for the moderate-risk H65 heavy chain, pING4621, was assembled by cloning the SalI to BstEII fragment from pING4620 into the same expression vector described above.

Example 7

A. Assembly of moderate-risk light chain

The moderate-risk humanized V- and J-segments of the light chain were assembled from six oligonucleotides, $H65K-1, HUH-K7, HUH-K6, HUH-K8, HUH-K4 and HUH-K5. The sequences of HUH-K7, HUH-K6 and HUH-K8 are set out in SEQ ID Nos: 62–64 and FIGS. 7 and 7A, respectively. The oligonucleotides were amplified with PCR primers H65K-2S and JK1-HindIII. Oligonucleotides containing the synthetic humanized antibody gene were mixed in pairs ($H65-K1+HUH-K7, HUH-K6+HUH-K4+HUH-K5) and incubated with Vent polymerase as described for the moderate-risk heavy chain. A portion of each reaction product (40 ul) was mixed in pairs ($H65H-K1/HUH-K7+HUH-K6, 8; HUH-K6, 8+HUH-K4, 5) and filled in as above. The light chain gene was then assembled by amplifying the full length gene with the PCR primers H65K-2S and JK1-HindIII with Vent polymerase for 25 cycles as outlined above. The assembled V/J region was cut with SalI and HindIII, purified by electrophoresis on an agarose gel, and assembled into a light chain antibody expression vector, pING4630.

B. Stable Transfection of Mouse Lymphoid Cells for the Production of He3 Antibody The cell line Sp2/0 (American Type Culture Collection #CRL1581) was grown in Dulbecco's Modified Eagle Medium plus 4.5 g/l glucose (DMEM, Gibco) plus 10% fetal bovine serum. Media were supplemented with glutamine/penicillin/streptomycin (Irvine Scientific, Irvine, Calif.).

The electroporation method of Potter, H., et al., *Proc. Natl. Acad. Sci., USA*, 81:7161 (1984) was used. After transfection, cells were allowed to recover in complete DMEM for 24–48 hours, and then seeded at 10,000 to 50,000 cells per well in 96-well culture plates in the presence of selective medium. Histidinol (Sigma) selection was at 1.71 ug/ml, and mycophenolic acid (Calbiochem) was at 6 ug/ml plus 0.25 mg/ml xanthine (Sigma). The electroporation technique gave a transfection frequency of $1-10 \times 10^{-5}$ for the Sp2/0 cells.

The He3 light chain expression plasmid pING4630 was linearized by digestion with PvuI restriction endonuclease and transfected into Sp2/0 cells, giving mycophenolic acid—resistant clones which were screened for light chain synthesis. The best 4 light chain—producing transfectants after outgrowth were pooled into 2 groups of 2 transfectants/pool and each pool was transfected with the He3 heavy chain expression plasmid, pING4621, that had been linearized with PvuI. After selection with histidinol, the clone producing the most light plus heavy chain, Sp2/0–4630+4621 Clone C1718, secreted antibody at approximately 22 µg/ul in the presence of $10^{-7}$ in dexamethasone in an overgrown culture in a T25 flask. This transfectoma has been deposited with the American Type Culture Collection, 1230 Parklawn Drive, Rockville, Md., 20852 on Dec. 1, 1992 as ATCC HB 11206.

C. Purification of He3 Antibody Secreted in Tissue Culture

Sp2/0–4630+4621 cells are grown in culture medium HB101 (Hana Biologics)+1% Fetal Bovine Serum, supplemented with 10 mM HEPES, 1× Glutamine-Pen-Strep (Irvine Scientific #9316). The spent medium is centrifuged at about 5,000×g for 20 minutes. The antibody level is measured by ELISA. Approximately 200 ml of cell culture supernatant is loaded onto a 2 ml Protein A-column (Sigma Chemicals), equiliberated with PBS (buffer 0.15M NaCl, 5 mM sodium phosphate, 1 mM potassium phosphate, buffer pH 7.2). The He3 antibody is eluted with a step pH gradient (pH 5.5, 4.5 and 2.5). A fraction containing He3 antibody (9% yield) but not bovine antibody, is neutralized with 1M Tris pH 8.5, and then concentrated 10-fold by Centrium 30 (Amicon) diluted 10-fold with PBS, reconcentrated 10-fold by Centricon 30, diluted 10-fold with PBS, and finally reconcentrated 10-fold. The antibody was stored in 0.25 ml aliquots at –20° C.

D. Affinity Measurements of He3 IgG for CD5

The affinity of He3 for CD5 was determined using Molt-4M cells, which express CD5 on their surface and $I^{125}$-labeled chimeric H65 IgG in a competitive binding assay.

For this assay, 20 µg of chimeric H65 IgG (cH65 IgG) was iodinated by exposure to 100 µl lactoperoxidase-glucose oxidase immobilized beads (Enzymobeads, BioRad), 100 µl of PBS, 1.0 mCi $I^{125}$ (Amersham, IMS30), 50 µl of 55 mM b-D-glucose for 45 minutes at 23° C. The reaction was quenched by the addition of 20 µl of 105 mM sodium metabisulfite and 120 mM potassium iodine followed by centrifugation for 1 minute to pellet the beads. $^{125}$I-cH65 IgG was purified by gel filtration using 7 mls of sephadex G25, using PBS (137 mM NaCl, 1.47 mM $KH_2PO_4$, 8.1 mM $Na_2HPO_4$, 2.68 mM KCl at pH 7.2–7.4) plus 0.1% BSA. $^{125}$I-cH65 IgG recovery and specific activity were determined by TCA precipitation.

Competitive binding was performed as follows: 100 µl of Molt-4M cells were washed two times in ice cold DHB binding buffer (Dubellco's modified Eagle's medium (Gibco, 320–1965PJ), 1.0% BSA and 10 mM Hepes at pH 7.2.–7.4). Cells were resuspended in the same buffer, plated into 96 v-bottomed wells (Costar) at $3 \times 10^5$ cells per well and pelleted at 4° C. by centrifugation for 5 min at 1,000 rpm using a Beckman JS 4.2 rotor; 50 µl of 2×-concentrated 0.1 nM $^{125}$I-cH65 IgG in DHB was then added to each well and competed with 50 µl of 2×—concentrated cH65 IgG or humanized antibody in DHB at final antibody concentrations from 100 nM to 0.0017 nM. Humanized antibody was obtained from culture supernatants of Sp2/0 clone C1718 which expresses He3 IgG. The concentration of the antibody in the supernatants was established by ELISA using a chimeric antibody as a standard. Binding was allowed to proceed at 4° C. for 5 hrs and was terminated by washing cells three times with 200 μl of DHB binding buffer by centrifugation for 5 min at 1,000 rpm. All buffers and operations were at 4° C. Radioactivity was determined by solubilizing cells in 100 μl of 1.0M NaOH and counting in a Cobra II auto gamma counter (Packard). Data from binding experiments were analyzed by the weighted nonlinear least squares curve fitting program, MacLigand, a Macintosh version of the computer program "Ligand" from Munson, Analyt. Biochem., 107:220 (1980). Objective statistical criteria (F, test, extra sum squares principle) were used to evaluate goodness of fit and for discriminating between models. Nonspecific binding was treated as a parameter subject to error and was fitted simultaneously with other parameters.

Figure 11:
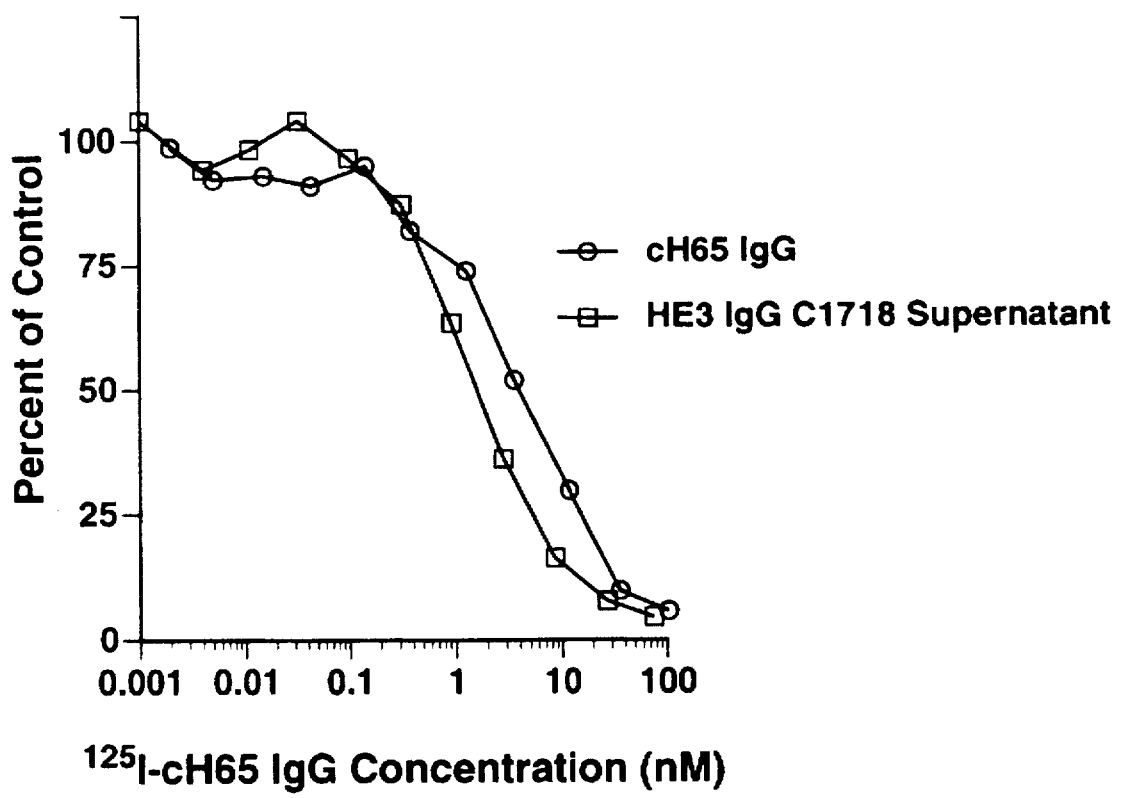
FIG. 11 is a graph of He3 IgG binding to CD5 found on Molt-4M, demonstrating that such binding is similar to that of cH65 IgG.

The results of the competition binding assay are provided in FIG. 11. These results demonstrate that the moderate-risk changes made in He3 IgG result in an antibody with a higher affinity than the chimeric mouse-human form of this antibody (cH65) for its target, CD5. In this particular case, moderate risk changes appear to increase affinity slightly, but a decrease may be expected in most cases.

Example 8

Preparation of XMMLY-H65 Anti-pan T Cell Immunoglobulin

The murine monoclonal antibody produced by cell line XMMLY-H65 (MoAbH65) is reactive with the human CD5 antigen. The cell line XMMLY-H65 was deposited with the American Type Culture Collection, 12301 Parklawn Drive, Rockville, Md., 20852 and designated Accession No. HB9286.

MoAb H65 was produced after immunization of BALB/c mice with the human T-cell line HSB-2 originally isolated from a patient with T-cell acute lymphocytic leukemia. Adams, et al. Can. Res. 28:1121 (1968). The murine myeloma cell line P3 7 NS/1-Ag-1-4 of Kohler et al. Emr. J. Immunol. 6:292 (1976) was fused with spleen cells from an immunized mouse by the technique of Galfre et al., Nature 266:550 (1977). One of the resulting hybrid colonies was found to secrete a MoAb that recognizes a pan-T-lymphocyte antigen with a molecular weight of 67 kD, expressed on approximately 95% of peripheral T-lymphocytes [Knowles, Leukocyte Typing II, 1,(E. Reinherz, et al. eds., Springer Verlag (1986)]. This antigen is not present on the surface of any other hematopoietic cells, and the antibody itself has been tested for binding to a large range of normal human tissues and found to be negative for all cells except for T-lymphocytes and a subpopulation of B lymphocytes.

The H65 antibody-producing hybrid cell line was cloned twice by limiting dilution and was grown as ascites tumors in BALB/c mice.

MoAb H65 was purified from mouse ascites by a modification of the method of Ey et al. Immunochem. 15:429 (1978). In brief, the thawed mouse ascites was filtered to remove lipid-like materials and was diluted with 2 to 3 volumes of 0.14M NaPO$_4$, pH 8.0, before application onto an immobilized protein A-Sepharose column of appropriate size. The unbound materials were removed from the column by washing with 0.14M NaPO$_4$, pH 8.0, until no further change in absorbance at 280 nm was seen. A series of column washes with 0.1M sodium citrate (pH 6.0, pH 5.0, pH 4.0, and pH 3.0) were then performed to elute bound antibody.

Peak fractions were pooled, adjusted to pH 7.0 with saturated Tris base, and concentrated by using a cell stirred with Amicon YM10 membrane (Amicon, Lexington, N.Y.). An antibody solution was then dialyzed against phosphate-buffered saline (PBS), pH 7.0, and was stored frozen at −70° C.

MoAb H65 is of the IgG$_1$ subclass, as determined by double diffusion in agar with the use of subclass-specific antisera (Miles-Yeda, Ltd. Rehovot, Israel). The serologic characteristics of this antibody and the biochemical characteristics of the gp67 (i.e., CD5) antigen were examined during the First International Workshop on Human Leukocyte Differentiation Antigens (Paris, 1982). MoAb H65 (workshop number: T34), and nine other MoAbs were found to have the same serologic pattern and to immunoprecipiate the gp67 antigen. Knowles, in Reinherz, et al., Leukocyte Typing II, 2: 259–288 (Springer-Verlag, 1986). In other studies, MoAb H65 has been shown to block the binding of FITC-conjugated anti-Leu-1 (Becton Dickson, Mountain View, Calif.) on gp67+cells indicating that both antibodies recognize the same epitope on the gp67 molecule or determinants that are located in such a configuration as to result in blocking by steric hindrance.

Example 9

The Use of Lyt-I In The Prophylactic Treatment of CollagenInduced Arthritis in DBA/IJ mice Collagen-induced arthritis (CIA) is a widely utilized model of human rheumatoid arthritis. CIA is characterized by a chronic polyarticular arthritis which can be induced in rodents and in primates by immunization with homologous or heterologous, native Type II collagen. The resulting arthritis resembles rheumatoid arthritis because there are similar histopathologic sequelae, cellular and humoral immune responses and restricted association with specific major histocompatibility complex (MHC) haplotypes.

Native, heterologous Type II collagen emulsified with complete Freund's adjuvant induces an arthritis-like autoimmune reaction in DBA/IJ mice after a single intradermal tail injection. The mice were obtained from Jackson Laboratories, Bar Harbor, Me. Initially, the arthritis is noticeable as a slight swelling of one or more digits in the fourth week post-immunization. The chronic phase of CIA continually worsens over the ensuing 8 weeks as the arthritis progresses from the digits into the remaining peripheral articulating joints and eventually ends with ankylosis of the involved joints. The histopathology of CIA is characterized by lymphocyte infiltration of the joint space, synovial MHC class II expression and pannus formation. Not all joints are involved on every mouse, so there is a spectrum of arthritic severity. In a group of ten or more mice, the overall arthritic severity develops in a linear fashion over the course of 10–12 weeks.

The CIA model was used to test the potential efficacy of a monoclonal antibody directed against the pan-T cell surface antigen, Lyt-1, the murine equivalent of CD5. The antibody was administered to the mice before the immunization with Type II collagen. Normal DBA/I mice were also treated with a single 0.4 mg/kg i.v. injection of anti-Lyt-1 and were sacrificed after 72 hours for FACS analysis and for in vitro proliferation assays on spleen and lymph node cells. Any efficacy of this antibody would indicate a beneficial T cell-directed approach in rheumatoid arthritis via the CD5 surface antigen.

Effects of anti-Lyt-1 on DBA/IJ Spleen Cells and Peripheral Lymph Nodes.

Antibody 53–7.313 is a rat $IgG_{2a}$ monoclonal antibody (ATCC Accession No. TIB 104) reactive with all alleles of the mouse lymphocyte differentiation antigen, Lyt-1. The IND1 antibody is a mouse $IgG_1$, anti-human melanoma antibody used as a negative control (Xoma Corp., Berkeley, Calif.). All other antibodies were obtained from Pharmingen Inc. (San Diego, Calif.) as direct conjugates for quantitation on a Becton-Dickinson FACScan instrument.

Male DBA/IJ mice, age 6–8 weeks, were administered a single intravenous dose of either phosphate buffered saline, IND1 or anti-Lyt-1 via the tail vein at 0.4 mg/kg in 0.1 ml of phosphate buffered saline. Mice were sacrificed for analysis three days after dosing. Single cell suspensions of spleens and peripheral lymph nodes were prepared by standard procedures and $1\times10^6$ cells were stained with the respective antibodies for fluorescence activated cell sorter (FACS) analysis. Proliferation assays were also performed to provide a second measure of T cell depletion. Cells ($1\times10^5$/well) were stimulated with Concanavalin A, Interleukin-2 (IL-2), IL-2 and H57.597 (a pan $\alpha,\beta$ T cell receptor antibody) or the Staphylococcal enterotoxins A and B. Cells were cultured for a total of 72 hours and proliferation was quantitated by the addition of $^3$H-methylthymidine for the last 24 hours. After 72 hours, the cells were harvested with an Inotech INB-384 harvesting and counting system, which collects the cells onto glass fiber filters with subsequent gas proportional beta particle detection. Results are generally expressed as the mean of triplicate wells±SEM in Tables 5 and 6.

A. FACS Analysis of Lymph Node and Spleen Cells

FACS analysis of lymph node cells (LNC) and spleen cells (SPC) from each treatment group (n=3/group) were analyzed for percent expression of $\alpha,\beta$ T cell receptor, CD3, CD4, CD5, and CD8. The results are presented in Table 4.

In Table 4, statistical significance was determined by Analysis of Variance followed by Duncan's New Multiple Range post-hoc test. These data indicate that administration of anti-Lyt-1 antibody results in a significant depletion of peripheral T lymphocytes at the 72 hour time point. The results could not be explained by residual circulating antibody as other T cell markers (CD3, etc.) are also depleted to a similar extent.

B. Effects of anti-Lyt-1 Administration on Proliferation Analysis

In vitro proliferation assays were performed on mice from each treatment group (n=3/group) in response to Concanavalin A, IL-2, IL-2+H57, Staphylococcal enterotoxin A and B (SEA and SEB). The results are presented in Table 5.

Overall, these data indicate that there is an observable and functional depletion of DBA/IJ T peripheral lymphocytes 72 hours after a single (0.4 mg/kg) intravenous dose of anti-Lyt-1 antibody.

C. Effects of anti-Lyt-1 on Collagen-induced Arthritisin DBA/IJ Mice.

A. Materials and Methods

Male DBA/IJ mice, age 6–8 weeks, were administered the antibodies 53–7.313 (anti-Lyt-1), IND1 (anti-melanoma) or phosphate buffered saline (PBS) in two intravenous (0.4 mg/kg) doses 48 hours apart starting four days prior to immunization with 100 µg of bovine type II collagen emulsified with an equal volume of Freund's complete adjuvant to a final injection volume of 100 µl. Each dose group was comprised of ten mice. Mice were monitored weekly starting on Day 21

TABLE 4

FACS Analysis of anti-Lyt-1 Treated DBA/1J Mice

| TREAT-MENT | CELL TYPE | $\alpha, \beta$TCR | CD3 | CD4 | CD8 | CD5 |
|---|---|---|---|---|---|---|
| PBS | LNC | 80.2 ± 2.2% | 79.8 ± 1.6% | 58.7 ± 1.4% | 19.4 ± 2.6% | 80.0 ± 0.6% |
| IND1 | LNC | 82.5 ± 1.3% | 82.6 ± 1.9% | 60.9 ± 2.0% | 21.1 ± 1.5% | 78.5 ± 1.2% |
| αLyt-1 | LNC | *62.7 ± 5.8% | *62.4 ± 1.0% | *42.0 ± 1.9% | 21.1 ± 0.2% | *56.0 ± 2.6% |
| PBS | SPC | 18.0 ± 2.8% | 25.0 ± 0.1% | 16.5 ± 2.1% | 4.10 ± 0.5% | 23.1 ± 0.1% |
| IND1 | SPC | 19.3 ± 1.6% | 22.8 ± 1.4% | 13.9 ± 0.8% | 4.20 ± 0.3% | 20.8 ± 1.5% |
| αLyt-1 | SPC | 14.0 ± 0.3% | *13.8 ± 0.4% | *8.07 ± 0.3% | *2.40 ± 0.1% | *11.0 ± 0.1% |

TABLE 5

Proliferation Analysis of anti-Lyt-1 Treated DBA/1J mice.

| TREAT-MENT | Concanavalin A | IL-2 | IL-2 + H57 | SEA | SEB |
|---|---|---|---|---|---|
| IND1 | 26547 ± 3501 | 1181 ± 234 | 11341 ± 1663 | 12324 ± 1968 | 8747 ± 2025 |
| αLyt-1 | *11561 ± 4375 | *593 ± 274 | *4090 ± 2383 | *5568 ± 2576 | *1138 ± 350 | after immunization. Individual mice were scored for arthritic severity by grading each paw on a scale from 0 to 2. A score of 1 indicated swelling in up to two toes ;and a score of 2 indicated swelling in more than two toes up to total paw involvement and ankylosis of the large joint in the later time points. An individual mouse could have a maximum arthritic severity score of 8. Mice were monitored until day 80 after collagen immunization and then were sacrificed by cervical dislocation. Results are expressed as the mean arthritic score for each dose group.

The changes in arthritic score during the course of the study are shown in FIG. 12. The overall conclusion in FIG. 12 is that administration of the anti-Lyt-1 antibody prior to collagen immunization caused a significant decrease in the resulting severity of arthritis. In all of the treatment groups, the appearance of visible symptoms initiated at approximately 30 days after immunization and progressed linearly until the end of the study. The anti-Lyt-1 treatment group began to show ameliorated arthritic symptoms at Day 48 and never developed arthritis to the same extent as the other two groups. The onset of arthritis was not significantly delayed by the anti-Lyt-1 treatment.

Statistical significance was determined by a Repeated Measures Analysis of Variance with one between subjects variable (antibody treatment). A Repeated Measures Analysis was necessary as each mouse was continually monitored for the duration of the study. Thus, the arthritic scores for consecutive days cannot be considered as independent observations contributing to the overall degrees of freedom in the F test for significant differences among groups. A Repeated Measures Analysis uses the degrees of freedom from the number of individuals per group instead of the number of observations. A typical between subjects Analysis of Variance may be inappropriate and may indicate false significance among the treatment groups. A comparison of means in the Treatment by Day after Immunization was done to determine the significance of anti-Lyt-1 treatment relative to PBS and IND1 control groups.

In conclusion, the intravenous administration of a rat monoclonal antibody reactive to the mouse equivalent of CD5, Lyt-1, is able to significantly decrease T lymphocytes in the spleen and in peripheral lymph nodes after a single 0.4 mg/kg dose. This T cell decrease is the probable mechanism for the significant ($p<0.01$) decrease in arthritic severity seen with the same anti-Lyt-1 dose prior to type II collagen immunization.

Example 10

Depletion of Human T Cells From SCID Mice by Treatment With H65 MoAb

Severe combined immunodeficient (CB.17 scid/scid; SCID) mice maintain human lymphoid cells for several months following transplantation of human peripheral blood mononuclear cells (PBMC). Such chimeric mice, referred to as PBMC/SCID mice, have functional human cells, as shown by the presence of human Ig in their serum. PBMC/SCID mice maintain human T cells in tissues such as spleen and blood. Human T cells present in PBMC/SCID mice are predominantly of a mature phenotype and express T cell antigens, including CD3, CD5, CD7, and CD4 or CD8. In addition, most T cells appear to be activated memory cells, as judged by the expression of HLA-DR and CD45RO. These engrafted T cells appear to be functional since (a) they may provide help to B cells to produce anti-tetanus toxoid antibodies, (b) they produce soluble interleukin-2 receptor (sIL-2R) which may be detected in plasma, and (c) they proliferate in response to mitogenic anti-human CD3 monoclonal antibodies supplemented with IL-2 in vitro.

Because of the presence of human T and B cells, PBMC/SCID mice offer an in vivo model system in which to evaluate the efficacy of anti-human T cell drugs, such as H65 MoAb, a mouse IgGI directed against human CD5.

The SCID mice were obtained from Taconic, Germantown, N.Y., and at 6 to 7 weeks of age were injected with 200 mg/kg cyclophosphamide intraperitoneally (i.p.) to ensure engraftment of human PBMC. Two days later, 25 to 40×10⁶ human PBMC, isolated by Ficoll-Hypaque density gradient centrifugation from lymphapheresis samples obtained from normal donors (HemaCare Corporation, Sherman Oaks, Calif.), were injected i.p.

At 2 to 3 weeks after PBMC injection, the mice were bled from the retro-orbital sinus and levels of human immunoglobulin (Ig) and human sIL-2R in plasma were quantified using sandwich ELISAs. Mice with low or undetectable levels of these human proteins were eliminated from the study and the remainder were divided into the various treatment groups (6 per group). The mice were then administered H65 MoAb (0.2 or 0.02 mg/kg/day), H65-based F(ab')$_2$ fragment (2 mg/kg/day) or vehicle (buffer) intravenously (i.v.) for 10 consecutive daily injections. One day after the last injection, the mice were bled and spleens were collected. Single cell suspensions of blood cells and splenocytes were prepared by standard methods. Recovered cells were then assayed for human T cell surface markers using flow cytometry.

Two to five hundred thousand cells were stained with the following FITC- or PE-conjugated Abs (Becton-Dickinson, Mountain View, Calif.): HLe-1-FITC (anti-CD45), Leu-2-FITC-(anti-CD8), and Leu-3-PE (anti-CD4). Samples were analyzed on a FACScan using log amplifiers. Regions to quantify positive cells were set based on staining of cells obtained from naive SCID mice. The absolute numbers of human antigen-positive cells recovered from SCID tissues were determined by multiplying the percent positive cells by the total number of cells recovered from each tissue sample. The total number of leukocytes in blood was calculated using a theoretical blood volume of 1.4 ml/mouse. Statistical comparisons between treatment groups were made using the Mann-Whitney U test.

Figures 14A, 14B:
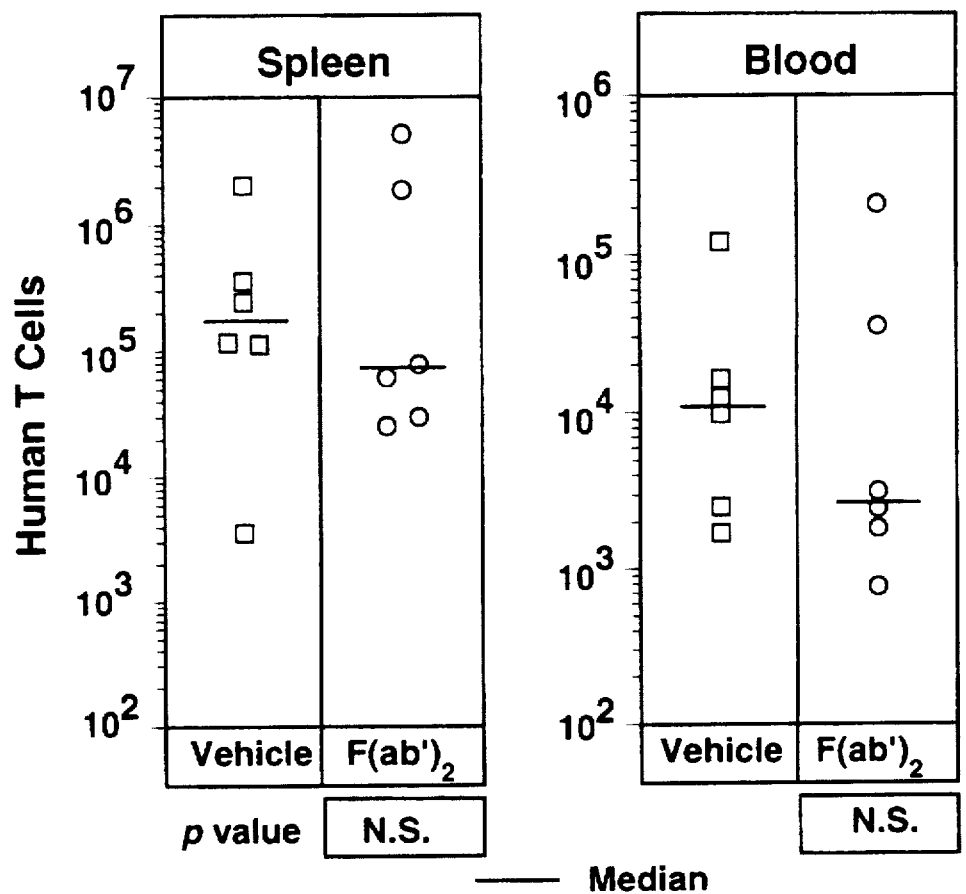
FIGS. 14A and 14B are schematic depictions of human T cell recovery in spleen and blood, respectively from PBMC/SCID mice following treatment with H65-based F(ab')$_2$ fragment.

The number of human T cells (CD4 plus CD8 cells) recovered from spleens and blood of PBMC/SCID mice following treatment with H65 MoAb or vehicle (control) is shown in FIG. 13. Significantly lower numbers of T cells were recovered from spleens and blood of mice treated with either 0.2 or 0.02 mg/kg/day H65 MoAb as compared to vehicle-treated mice. In contrast, treatment with 2 mg/kg/day of an H65-based F(ab')$_2$ fragment did not significantly deplete human T cells from spleens or blood, even though a 10 to 100-fold higher dose was used (FIG. 14).

These results indicate that an anti-human CD5 MoAb depletes human T cells in an experimental animal model. The ability of this MoAb to deplete human T cells from SCID mice is apparently dependent on the Fc portion of the MoAb, as an F(ab')$_2$ fragment was ineffective.

Example 11

The Use of OX19 Monoclonal Antibody In The Prophylactic Treatment of Collagen Induced Arthritis in Diabetes-Resistant BB Rats Collagen-induced arthritis (CIA) in the diabetes-resistant Biobreeding (DR BB) rat is a particularly relevant animal model of human rheumatoid arthritis, in that the DR BB rat RT1.Dβ gene encodes a nucleotide sequence homologous to the human HLA-DRβ gene reported to be associated with rheumatoid arthritis susceptibility. In this model, DR BB rats are administered a single intradermal tail injection of heterologous Type II collagen emulsified with incomplete Freund's adjuvant. Development of the arthritis is considerably faster than in the DBA/1J CIA model. Onset of clinical signs occurs 1.5 to 2 weeks after collagen immunization, with peak swelling observed a few days after onset. Incidence is generally quite high (>85% of animals immunized). The swelling is generally severe, involves the entire footpad and ankle joint, and is restricted to the hindlimbs. Histopathological examination has revealed that the arthritis begins as a proliferative synovitis with pannus formation at the joint margins that is followed by a bidirectional erosion of both the outer (unmineralized) and inner (mineralized) layers of cartilage.

This experiment uses the DR BB CIA rat model to assess the efficacy of a monoclonal antibody (MoAb), OX19 directed against the equivalent of the CD5 antigen in the rat. The antibody was administered to the rats prior to immunization with Type II collagen. Normal Sprague-Dawley rats were also treated with a single 0.5 mg/kg i.v. injection and were sacrificed after 3 hours for evaluation of MoAb binding to T cells, or after 2 days for quantitation of T cells in lymphoid tissues using flow cytometry.

A. Effects of OX19 MoAb on T Cells In Lymphoid Tissues of Normal Sorague-Dawley Rats OX19 MoAb is a mouse IgG1 directed against the equivalent of rat CD5 antigen present on rat T cells. OX19 hybridoma is available from the European Collection of Animal Cell Cultures (ECACC) and has ECACC No. 84112012. H65 MoAb, a mouse IgG1 reactive against human CD5, was used as an isotype matched negative control. Fluorescein- conjugated antibodies directed against surface antigens on rat pan-T cells (W3/13), CD4 cells (W3/25) and CD8 cells (OX8) were obtained from Accurate Chemical and Scientific Corporation, Westbury, N.Y. for flow cytometric quantitation of T cells in rat lymphoid tissues. Phycoerythrin-conjugated goat anti-mouse IgG1 (Caltag Laboratories, South San Francisco, Calif.) was used to detect OX19 MoAb bound to rat T cells in a two-color analysis.

Male Sprague-Dawley rats (Simonsen Laboratories, Gilroy, Calif.), 100 to 150 grams, were administered a single i.v. bolus injection of OX19 MoAb (0.5 mg/kg) or control MoAb (0.5 mg/kg) in phosphate buffered saline containing 0.1% Tween 80 (PBS/Tween). Animals were sacrificed at 3 hours (binding experiment) or 2 days (depletion experiment) after dosing. Single cell suspensions of blood, spleens and lymph nodes were prepared by standard procedures and $1 \times 10^6$ cells were stained with appropriate antibodies for FACS analysis.

A. Binding of OX19 MoAb to Rat T Cells In Vivo

Blood, spleen and lymph node cells from one animal in each treatment group were analyzed for percentage of CD4 and CD8 T cells, and percentage of CD4 and CD8 T cells that also stained positively for surface-bound mouse IgG1. The results are presented in Table 6. T cells were depleted from the blood at 3 hours after OX19 MoAb administration. Almost all of the T cells that remained in the blood, and most of those present in the spleen and lymph nodes in the OX19 MoAb-treated rat also stained positively for surface-bound mouse IgG1, indicating that the dose of OX19 MoAb used was sufficient to saturate most of the T cells in these major lymphoid organs. These results provide doses useful in therapeutic applications.

B. Effect of OX19 MoAb Treatment on T Cell Subpopulations in Rat Lymphoid Tissues Blood, spleen and lymph node cells from two animals in each treatment group were analyzed for percentage of pan-T, CD4 and CD8 cells. The results are presented in Table 7 as the mean of the two animals. OX19 MoAb treatment resulted in depletion of T cells from all tissues examined as compared to treatment with the control MoAb. These results also provide appropriate doses to be used in therapeutic applications using antibodies according to the invention.

Example 12

Effect of OX19 MoAb Treatment on Development of Collagen-Induced Arthritis in DR BB Rats Male DR BB/Wor rats (obtained from the University of Massachusetts breeding facility; 8 per treatment group), age 6 weeks, were administered i.v. injections of OX19 MoAb (0.5 mg/kg), control MoAb (0.5 mg/kg) or buffer (PBS/Tween) on day 7 and day 4 prior to immunization at the base of the tail on day 0 with 0.3 mg of bovine Type II collagen emulsified in 0.15 ml

TABLE 6

Bind of OX19 MoAb to Rat T Cells In Vivo.

| | | | | % Positive Cell | |
| Tissue | Treatment | CD4 | CD4/mIgG1* | CD8 | CD8/mIgG1* |
| --- | --- | --- | --- | --- | --- |
| Blood | H65 MoAb | 47.0 | 6.7 | 11.1 | 5.7 |
| | OX19 | 8.7 | 96.2 | 4.1 | 70.2 |
| Spleen | H65 MoAb | 23.1 | 14.8 | 4.4 | 20.6 |
| | OX19 MoAb | 16.4 | 84.8 | 3.4 | 73.6 |
| Lymph Node | H65 MoAb | 66.9 | 4.2 | 7.4 | 6.5 |
| | OX19 MoAb | 54.7 | 96.2 | 7.3 | 96.8 |

*The % of CD4 or CD8 cells that are also positive for mouse IgG1.

TABLE 7

FACS Analysis of Tissues from OX19 MAb-Treated Rats.

| | | | % Positive Cells | |
| Tissue | Treatment | Pan-T | CD4 | CD8 |
| --- | --- | --- | --- | --- |
| Blood | H65 MoAB | 61.8 | 50.4 | 12.0 |
| | OX19 MoAb | 47.0 | 37.3 | 8.8 |
| Spleen | H65 MoAb | 36.0 | 25.3 | 7.1 |
| | OX19 MoAb | 21.5 | 9.9 | 5.0 |
| Lymph Node | H65 MoAb | 74.5 | 62.7 | 13.1 |
| | OX19 MoAb | 33.8 | 24.9 | 4.3 | of incomplete Freund's adjuvant. Rats were scored daily for arthritis beginning 8 days after collagen immunization severity was graded on a scale from 0 to 2, with a score of 1 indicating moderate swelling and a score of 2 indicating severe swelling. An individual animal could have a maximum arthritic severity score of 4 if there was bilateral hindlimb involvement.

Figure 15:
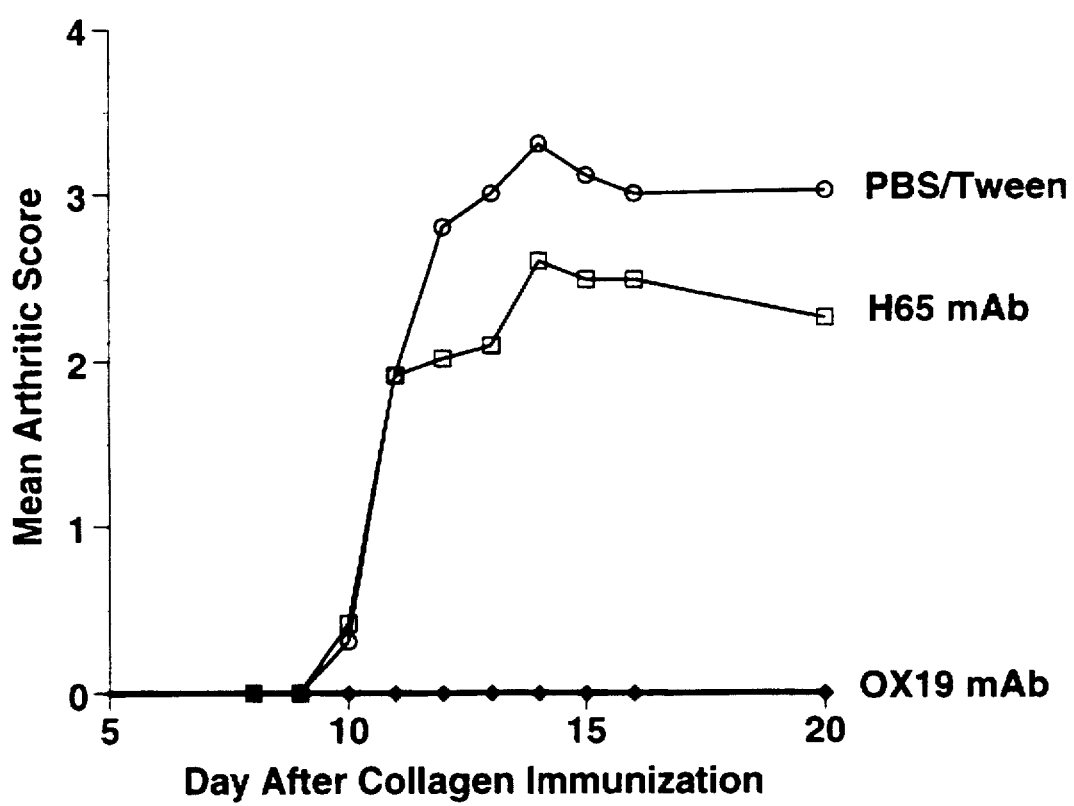
FIG. 15 is a graph of the effects of OX19 MoAb on the severity of DR BB rat collagen-induced arthritis.

The changes in arthritic score during the course of the study are shown in FIG. 15 and the arthritic incidence for each treatment group is presented in Table 8.

Control (buffer and control MoAb-treated) rats developed severe, predominantly bilateral hindlimb arthritis between days 10 and 14 with high incidence (88% for both groups). Treatment with OX19 MoAb completely prevented development of arthritis (0% incidence).

In conclusion, a 0.5 mg/kg intravenous dose of a mouse MoAb directed against the rat equivalent of CD5 was found to saturate and subsequently deplete T cells from lymphoid tissues of normal rats. This T cell depletion is the probable mechanism for the complete inhibition of arthritis development observed when the MoAb was administered prior to Type II collagen immunization in DR BB rats.

Example 13

Treatment of Rheumatoid Arthritis

Patients having rheumatoid arthritis (RA) are selected for treatment using an anti-pan T cell antibody of this invention.

Anti-CD5 antibody prepared as described above is administered to patients at doses of about 0.005 to 2.0 mg/kg/day for a period of 1–5 days, preferably 1–2 days. Alternatively, the dose may be given every 2–30

TABLE 8

Effect of OX19 MoAb Treatment on Arthritis Incidence

| TREAT-MENT | Total arthritics (1 or both limbs) | Total Arthritics (Both limbs) | Score of "2" (1 or both limbs) | Score of "2" (Both Limbs) |
|---|---|---|---|---|
| PBS/Tween | 7/8 (88%) | 7/8 (88%) | 7/8 (88%) | 5/8 (63%) |
| Control MoAb | 7/8 (88%) | 4/8 (50%) | 6/8 (75%) | 4/8 (50%) |
| OX19 MoAb | 0/8 (0%) | 0/8 (0%) | 0/8 (0%) | 0/8 (0%) | days instead of daily if chimeric and humanized MoAbs are used due to their increased half-life. To determine optimum dose and schedule, patients are treated at each dose and schedule in a dose escalating regimen. Patients are monitored using several indicia, including joint swelling and tenderness scores. Results are shown in FIG. 11.

Example 14

Treatment of SLE

Systemic Lupus Erythematosus (SLE) is a multisystemic disease characterized by inflammation and autoimmunity. Some of the more frequent manifestations include fatigue, anemia, fever, rashes, photosensitivity, alopecia, arthritis, pericarditis, pleurisy, vasculitis, nephritis and central nervous system disease. Under the Revised Criteria for Classification of SLE, a person is said to have SLE for purposes of clinical studies if any four or more of the aforementioned specified criteria are present, serially or simultaneously, during any interval of observation.

Anti-CD5 antibody prepared as described above is administered to patients at doses of about 0.005 to 2.0 mg/kg/day for a period of 1–5 days, preferably 1–2 days. Alternatively, the dose may be given every 2–30 days instead of daily if chimeric and humanized MoAbs are used due to their increased half-life. To determine optimum dose and schedule, patients are treated at each dose and schedule in a dose escalating regimen.

Example 15

Treatment of Psoriasis

Psoriasis is a disease of autoimmune etiology which classically appears as plaques over the elbows and knees, although other areas of the skin are frequently afflicted. Abnormalities of the nails and the joints are also frequently observed. Particularly inflammatory joint disease can occur in an occasionally erosive and severe form.

Anti-CD5 antibody prepared as described above is administered to patients at doses of about 0.005 to 2.0 mg/kg/day for a period of 1–5 days, preferably 1–2 days. Alternatively, the dose may be given every 2–30 days instead of daily if chimeric and humanized MoAbs are used due to their increased half-life. To determine optimum dose and schedule, patients are treated at each dose and schedule in a dose escalating regimen.

Clinical observation includes evaluation of the patient's overall status as well as special attention to the psoriatic plaques. Additionally, monitoring of laboratory parameters such as white blood count and differential are recommended. Symptoms which may indicate poor tolerance to therapy or complications include nausea, vomiting, fatigue, rash, fever, chills and syncope. Any unexplained depletion in white blood cells other than lymphocytes is an indication to discontinue therapy. Preferably, differential analysis of lymphocytes is carried out. That is, analysis of the total number of T cells and B cells should be determined.

Example 16

Treatment of Type I Diabetes

There are two major types of diabetes. Type I has classically been associated with a requirement for exogenous insulin. Type I typically occurs before the age of 40 and is associated with an absence of insulin secretion. The pancreas of patients with long-term Type I insulin-dependent diabetes are devoid of pancreatic islet cells. There is a large body of evidence that the etiology of Type I insulin-dependent diabetes (IDDM) is autoimmune.

Patients are diagnosed as having IDDM based on the criteria established by the American Diabetes Association. Anti-CD5 antibody prepared as described above is administered to patients at doses of about 0.005 to 2.0 mg/kg/day for a period of 1–5 days, preferably 1–2 days. Alternatively, the dose may be given every 2–30 days instead of daily if chimeric and humanized MoAbs are used due to their increased half-life. To determine optimum dose and schedule, patients are treated at each dose and schedule in a dose escalating regimen.

During the study, the patients were monitored by clinical and laboratory parameters. Clinical symptoms indicating poor tolerance to therapy or complications include fatigue, vomiting, rash, fever, chills, and syncope. Laboratory evaluation included white blood cell counts with differential analysis daily and blood glucose levels at least twice a day.

Using diagnostic criteria predictive of the onset of Type I diabetes, patients may be selected for prophylactic treatment. This treatment follows the dose and schedule noted above for treatment of clinical insulin dependent diabetes.

While the invention has been described in terms of specific examples and preferred embodiments, is understood that variations and improvements will occur to those skilled in the art. Therefore, it is recognized that there are numerous variations and improvements which come within the scope of the invention as claimed.

We claim:

1. A method for modifying an antibody variable domain, said method comprising:
   (a) identifying the risk assigned to amino acid positions in said antibody variable domain using the paired bind and bury lines as shown in FIG. 6A or 6B; and
   (b) changing amino acid residues at low, moderate, or low and moderate risk positions in said domain to the amino acid residue in the corresponding position in the amino acid sequence of a selected antibody light or heavy chain variable region sequence or consensus sequence; and
   (c) obtaining a modified antibody variable domain that binds antigen.

2. The method of claim 1, wherein said amino acid sequence in part (b) is said antibody light or heavy chain variable region sequence.

3. The method of claim 1, wherein said amino acid sequence in part (b) is said antibody light or heavy chain variable region consensus sequence.

4. The method of any one of claims 1-3 wherein the amino acid residues that are changed are all at low risk positions.

5. The method of claim 4, wherein at least one position is in a CDR as defined by Kabat.

6. The method of any one of claims 1-3, wherein the amino acid residues that are changed are at both low and moderate risk sites.

7. The method of claim 6, wherein at least one position is in a CDR as defined by Kabat.

8. The method of any one of claims 1-3, wherein said variable domain or portion thereof is in the light chain.

9. The method of any one of claims 1-3, wherein said variable domain or portion thereof is in the heavy chain.

10. A method for modifying the variable region sequence of an antibody light chain, said method comprising:
    (a) identifying the risk assigned to amino acid positions in said antibody light chain's variable region sequence using the paired bind and bury lines as shown in FIG. 6A; and
    (b) changing amino acid residues at low, moderate, or low and moderate risk positions in said variable region sequence to the amino acid residue in the corresponding position in the amino acid sequence of a selected antibody light chain variable region sequence or consensus sequence; and
    (c) obtaining a modified variable region sequence of an antibody light chain that, when associated with a heavy chain variable region, binds antigen.

11. The method of claim 10, wherein said amino acid sequence in part (b) is said antibody light chain variable region sequence.

12. The method of claim 10, wherein said amino acid sequence in part (b) is said antibody light chain variable region consensus sequence.

13. The method of any one of claims 10-12, wherein the amino acid residues that are changed are all at low risk positions.

14. The method of claim 13 wherein at least one position is in a CDR as defined by Kabat.

15. The method of any one of claims 10-12, wherein the amino acid residues that are changed are at both low and moderate risk sites.

16. The method of claim 15, wherein at least one position is in a CDR as defined by Kabat.

17. A method for modifying the variable region sequence of an antibody heavy chain, said method comprising:
    (a) identifying the risk assigned to amino acid positions in said antibody heavy chain's variable region sequence using the paired bind and bury lines as shown in FIG. 6B; and
    (b) changing amino acid residues at low, moderate, or low and moderate risk positions in said variable region sequence to the amino acid residue in the corresponding position in the amino acid sequence of a selected antibody heavy chain variable region sequence or consensus sequence; and
    (c) obtaining a modified variable region sequence of an antibody heavy chain that, when associated with a light chain variable region, binds antigen.

18. The method of claim 17, wherein said amino acid sequence in part (b) is said antibody heavy chain variable region sequence.

19. The method of claim 17, wherein said amino acid sequence in part (b) is said antibody heavy chain variable region consensus sequence.

20. The method of any one of claims 17-19, wherein the amino acid residues that are changed are all at low risk positions.

21. The method of claim 20, wherein at least one position is in a CDR as defined by Kabat.

22. The method of any one of claims 17-19, wherein the amino acid residues that are changed are at both low and moderate risk sites.

23. The method of claim 22, wherein at least one position is in a CDR as defined by Kabat.

* * * * *

SEQUENCE LISTING ( 1 ) GENERAL INFORMATION:

( i i i ) NUMBER OF SEQUENCES: 67

( 2 ) INFORMATION FOR SEQ ID NO:1:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Asp Ile Val Leu Thr Gln Ser Pro Ala Thr Leu Ser Val Thr Pro Gly
 1               5                  10                  15
Asn Ser Val Ser Leu Ser Cys Arg Ala Ser Gln Ser Ile Gly Asn Asn
             20                  25                  30
Leu His Trp Tyr Gln Gln Lys Ser His Glu Ser Pro Arg Leu Leu Ile
         35                  40                  45
Lys Tyr Ala Ser Gln Ser Ile Ser Gly Ile Pro Ser Arg Phe Ser Gly
     50                  55                  60
Ser Gly Ser Gly Thr Asp Phe Thr Leu Ser Ile Asn Ser Val Glu Thr
 65                  70                  75                  80
Glu Asp Phe Gly Met Tyr Phe Cys Gln Gln Ser Asn Ser Trp Pro Tyr
                 85                  90                  95
Thr Phe Gly Gly Gly Thr Lys Leu Asp Ile Lys
                100                 105
```

( 2 ) INFORMATION FOR SEQ ID NO:2:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Asp Ile Val Met Thr Gln Ser Pro Ser Ser Leu Ser Val Ser Ala Gly
 1               5                  10                  15
Glu Arg Val Thr Met Ser Cys Lys Ser Ser Gln Ser Leu Leu Asn Ser
             20                  25                  30
Gly Asn Gln Lys Asn Phe Leu Ala Trp Tyr Gln Gln Lys Pro Gly Gln
         35                  40                  45
Pro Pro Lys Leu Leu Ile Tyr Gly Ala Ser Thr Arg Glu Ser Gly Val
     50                  55                  60
Pro Asp Arg Phe Thr Gly Ser Gly Ser Gly Thr Asp Phe Thr Leu Thr
 65                  70                  75                  80
Ile Ser Ser Val Gln Ala Glu Asp Leu Ala Val Tyr Tyr Cys Gln Asn
                 85                  90                  95
Asp His Ser Tyr Pro Leu Thr Phe Gly Ala Gly Thr Lys Leu Glu Ile
                100                 105                 110
Lys
```

( 2 ) INFORMATION FOR SEQ ID NO:3:

( i ) SEQUENCE CHARACTERISTICS:
        ( A ) LENGTH: 103 amino acids ( B ) TYPE: amino acid
( D ) TOPOLOGY: linear ( i i ) MOLECULE TYPE: protein ( x i ) SEQUENCE DESCRIPTION: SEQ ID NO:3:

| Xaa | Ser | Val | Leu | Thr | Gln | Pro | Pro | Ser | Val | Ser | Gly | Ala | Pro | Gly | Gln |
| 1 | | | | 5 | | | | | 10 | | | | | 15 | |
| Arg | Val | Thr | Ile | Ser | Cys | Thr | Gly | Ser | Ser | Ser | Asn | Ile | Gly | Ala | Gly |
| | | | 20 | | | | | 25 | | | | | 30 | | |
| Asn | His | Val | Lys | Trp | Tyr | Gln | Gln | Leu | Pro | Gly | Thr | Ala | Pro | Lys | Leu |
| | | 35 | | | | | 40 | | | | | 45 | | | |
| Leu | Ile | Phe | His | Asn | Asn | Ala | Arg | Phe | Ser | Val | Ser | Lys | Ser | Gly | Ser |
| | | 50 | | | | 55 | | | | | 60 | | | | |
| Ser | Ala | Thr | Leu | Ala | Ile | Thr | Gly | Leu | Gln | Ala | Glu | Asp | Glu | Ala | Asp |
| 65 | | | | 70 | | | | | 75 | | | | | 80 | |
| Tyr | Tyr | Cys | Gln | Ser | Tyr | Asp | Arg | Ser | Leu | Arg | Val | Phe | Gly | Gly | Gly |
| | | | | 85 | | | | | 90 | | | | | 95 | |
| Thr | Lys | Leu | Thr | Val | Leu | Arg | | | | | | | | | |
| | | | 100 | | | | | | | | | | | | |

( 2 ) INFORMATION FOR SEQ ID NO:4:

( i ) SEQUENCE CHARACTERISTICS:
( A ) LENGTH: 111 amino acids
( B ) TYPE: amino acid
( D ) TOPOLOGY: linear ( i i ) MOLECULE TYPE: protein ( x i ) SEQUENCE DESCRIPTION: SEQ ID NO:4:

| Gln | Ser | Val | Leu | Thr | Gln | Pro | Pro | Ser | Ala | Ser | Gly | Thr | Pro | Gly | Gln |
| 1 | | | | 5 | | | | | 10 | | | | | 15 | |
| Arg | Val | Thr | Ile | Ser | Cys | Ser | Gly | Thr | Ser | Ser | Asn | Ile | Gly | Ser | Ser |
| | | | 20 | | | | | 25 | | | | | 30 | | |
| Thr | Val | Asn | Trp | Tyr | Gln | Gln | Leu | Pro | Gly | Met | Ala | Pro | Lys | Leu | Leu |
| | | 35 | | | | | 40 | | | | | 45 | | | |
| Ile | Tyr | Arg | Asp | Ala | Met | Arg | Pro | Ser | Gly | Val | Pro | Asp | Arg | Phe | Ser |
| | | 50 | | | | 55 | | | | | 60 | | | | |
| Gly | Ser | Lys | Ser | Gly | Ala | Ser | Ala | Ser | Leu | Ala | Ile | Gly | Gly | Leu | Gln |
| 65 | | | | 70 | | | | | 75 | | | | | 80 | |
| Ser | Glu | Asp | Glu | Thr | Asp | Tyr | Tyr | Cys | Ala | Ala | Trp | Asp | Val | Ser | Leu |
| | | | | 85 | | | | | 90 | | | | | 95 | |
| Asn | Ala | Tyr | Val | Phe | Gly | Thr | Gly | Thr | Lys | Val | Thr | Val | Leu | Gly | |
| | | | 100 | | | | | 105 | | | | | 110 | | |

( 2 ) INFORMATION FOR SEQ ID NO:5:

( i ) SEQUENCE CHARACTERISTICS:
( A ) LENGTH: 113 amino acids
( B ) TYPE: amino acid
( D ) TOPOLOGY: linear ( i i ) MOLECULE TYPE: protein ( x i ) SEQUENCE DESCRIPTION: SEQ ID NO:5:

| Asp | Val | Gln | Leu | Gln | Glu | Ser | Gly | Pro | Ser | Leu | Val | Lys | Pro | Ser | Gln |
| 1 | | | | 5 | | | | | 10 | | | | | 15 | |
| Thr | Leu | Ser | Leu | Thr | Cys | Ser | Val | Thr | Gly | Asp | Ser | Ile | Thr | Ser | Asp |
| | | | 20 | | | | | 25 | | | | | 30 | | |
| Tyr | Trp | Ser | Trp | Ile | Arg | Lys | Phe | Pro | Gly | Asn | Arg | Leu | Glu | Tyr | Met |

```
                         35                          40                          45
        Gly  Tyr  Val  Ser  Tyr  Ser  Gly  Ser  Thr  Tyr  Tyr  Asn  Pro  Ser  Leu  Lys
                  50                        55                        60

Ser  Arg  Ile  Ser  Ile  Thr  Arg  Asp  Thr  Ser  Lys  Asn  Gln  Tyr  Tyr  Leu
        65                       70                        75                       80

Asp  Leu  Asn  Ser  Val  Thr  Thr  Glu  Asp  Thr  Ala  Thr  Tyr  Tyr  Cys  Ala
                            85                        90                       95

Asn  Trp  Asp  Gly  Asp  Tyr  Trp  Gly  Gln  Gly  Thr  Ser  Val  Thr  Val  Ser
                       100                      105                      110

Ala
```

( 2 ) INFORMATION FOR SEQ ID NO:6:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
        Glu  Val  Lys  Leu  Val  Glu  Ser  Gly  Gly  Gly  Leu  Val  Gln  Pro  Gly  Gly
        1                   5                        10                       15

Ser  Leu  Arg  Leu  Ser  Cys  Ala  Thr  Ser  Gly  Phe  Thr  Phe  Ser  Asp  Phe
                            20                       25                       30

Tyr  Met  Glu  Trp  Val  Arg  Gln  Pro  Pro  Gly  Lys  Arg  Leu  Glu  Trp  Ile
                       35                       40                       45

Ala  Ala  Ser  Arg  Asn  Lys  Gly  Asn  Lys  Tyr  Thr  Thr  Glu  Tyr  Ser  Ala
                  50                        55                       60

Ser  Val  Lys  Gly  Arg  Phe  Ile  Val  Ser  Arg  Asp  Thr  Ser  Gln  Ser  Ile
        65                       70                       75                       80

Leu  Tyr  Leu  Gln  Met  Asn  Ala  Leu  Arg  Ala  Glu  Asp  Thr  Ala  Ile  Tyr
                            85                       90                       95

Tyr  Cys  Ala  Arg  Asn  Tyr  Tyr  Gly  Ser  Thr  Trp  Tyr  Phe  Asp  Val  Trp
                       100                      105                      110

Gly  Ala  Gly  Thr  Thr  Val  Thr  Val  Ser  Ser
                  115                      120
```

( 2 ) INFORMATION FOR SEQ ID NO:7:

( i ) SEQUENCE CHARACTERISTICS:
        ( A ) LENGTH: 117 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
        Gln  Val  Gln  Leu  Glu  Gln  Ser  Gly  Pro  Gly  Leu  Val  Arg  Pro  Ser  Gln
        1                   5                        10                       15

Thr  Leu  Ser  Leu  Thr  Cys  Thr  Val  Ser  Gly  Thr  Ser  Phe  Asp  Asp  Tyr
                            20                       25                       30

Tyr  Ser  Thr  Trp  Val  Arg  Gln  Pro  Pro  Gly  Arg  Gly  Leu  Glu  Trp  Ile
                       35                       40                       45

Gly  Tyr  Val  Phe  Tyr  His  Gly  Thr  Ser  Asp  Thr  Asp  Thr  Pro  Leu  Arg
                  50                        55                       60

Ser  Arg  Val  Thr  Met  Leu  Val  Asn  Thr  Ser  Lys  Asn  Gln  Phe  Ser  Leu
        65                       70                       75                       80

Arg  Leu  Ser  Ser  Val  Thr  Ala  Ala  Asp  Thr  Ala  Val  Tyr  Tyr  Cys  Ala
```

85                          90                              95
        Arg  Asn  Leu  Ile  Ala  Gly  Cys  Ile  Asp  Val  Trp  Gly  Gln  Gly  Ser  Leu
                       100                      105                 110
        Val  Thr  Val  Ser  Ser
                       115

( 2 ) INFORMATION FOR SEQ ID NO:8:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

Glu  Val  Gln  Leu  Val  Gln  Ser  Gly  Gly  Val  Val  Gln  Pro  Gly  Arg
        1                   5                        10                       15

Ser  Leu  Arg  Leu  Ser  Cys  Ser  Ser  Ser  Gly  Phe  Ile  Phe  Ser  Ser  Tyr
                            20                  25                      30

Ala  Met  Tyr  Trp  Val  Arg  Gln  Ala  Pro  Gly  Lys  Gly  Leu  Glu  Trp  Val
                       35                      40                      45

Ala  Ile  Ile  Trp  Asp  Asp  Gly  Ser  Asp  Gln  His  Tyr  Ala  Asp  Ser  Val
                  50                      55                      60

Lys  Gly  Arg  Phe  Thr  Ile  Ser  Arg  Asn  Asp  Ser  Lys  Asn  Thr  Leu  Phe
        65                            70                      75                      80

Leu  Gln  Met  Asp  Ser  Leu  Arg  Pro  Glu  Asp  Thr  Gly  Val  Tyr  Phe  Cys
                                 85                      90                      95

Ala  Arg  Asp  Gly  Gly  His  Gly  Phe  Cys  Ser  Ser  Ala  Ser  Cys  Phe  Gly
                            100                     105                     110

Pro  Asp  Tyr  Trp  Gly  Gln  Gly  Thr  Pro  Val  Thr  Val  Ser  Ser
                       115                     120                     125

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

Asn  Ser  Gly  Asn  Gln  Lys
        1                   5

( 2 ) INFORMATION FOR SEQ ID NO:10:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

Asn  Lys  Gly
        1

( 2 ) INFORMATION FOR SEQ ID NO:11:

( i ) SEQUENCE CHARACTERISTICS:
        ( A ) LENGTH: 3 amino acids
        ( B ) TYPE: amino acid (D) TOPOLOGY: linear (ii) MOLECULE TYPE: protein (xi) SEQUENCE DESCRIPTION: SEQ ID NO:11:

Gly Ser Thr
1

(2) INFORMATION FOR SEQ ID NO:12:

(i) SEQUENCE CHARACTERISTICS:
(A) LENGTH: 9 amino acids
(B) TYPE: amino acid
(D) TOPOLOGY: linear (ii) MOLECULE TYPE: protein (xi) SEQUENCE DESCRIPTION: SEQ ID NO:12:

His Gly Phe Cys Ser Ser Ala Ser Cys
1               5

(2) INFORMATION FOR SEQ ID NO:13:

(i) SEQUENCE CHARACTERISTICS:
(A) LENGTH: 107 amino acids
(B) TYPE: amino acid
(D) TOPOLOGY: linear (ii) MOLECULE TYPE: protein (xi) SEQUENCE DESCRIPTION: SEQ ID NO:13:

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Xaa Ile Ser Xaa Tyr
            20                  25                  30

Leu Xaa Trp Tyr Gln Gln Lys Pro Gly Lys Ala Pro Lys Leu Leu Ile
        35                  40                  45

Tyr Ala Ala Ser Xaa Leu Xaa Ser Gly Val Pro Ser Arg Phe Ser Gly
    50                  55                  60

Ser Gly Ser Gly Thr Xaa Phe Thr Leu Thr Ile Ser Ser Leu Gln Pro
65                  70                  75                  80

Glu Asp Phe Ala Thr Tyr Tyr Cys Gln Gln Tyr Xaa Xaa Xaa Pro Xaa
                85                  90                  95

Thr Phe Gly Gln Gly Thr Lys Val Glu Ile Lys
                100                 105

(2) INFORMATION FOR SEQ ID NO:14:

(i) SEQUENCE CHARACTERISTICS:
(A) LENGTH: 107 amino acids
(B) TYPE: amino acid
(D) TOPOLOGY: linear (ii) MOLECULE TYPE: protein (xi) SEQUENCE DESCRIPTION: SEQ ID NO:14:

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

```
            Ser   Gly   Ser   Gly   Thr   Asp   Phe   Thr   Leu   Thr   Ile   Ser   Arg   Leu   Glu   Pro
            65                      70                              75                              80

Gly   Asp   Phe   Ala   Val   Tyr   Tyr   Cys   Gln   Gln   Tyr   Gly   Ser   Ser   Pro   Xaa
                                    85                          90                              95

Thr   Phe   Gly   Gln   Gly   Thr   Asp   Val   Glu   Ile   Lys
                              100                       105
```

( 2 ) INFORMATION FOR SEQ ID NO:15:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
            Asp   Ile   Val   Met   Thr   Gln   Ser   Pro   Leu   Ser   Leu   Pro   Val   Thr   Pro   Gly
            1                       5                           10                              15

Glu   Pro   Ala   Ser   Ile   Ser   Cys   Arg   Ser   Ser   Gln   Ser   Leu   Leu   Asn   Asn
                                    20                          25                              30

Tyr   Leu   Asn   Trp   Tyr   Leu   Gln   Lys   Pro   Gly   Gln   Ser   Pro   Gln   Leu   Leu
                              35                          40                              45

Ile   Tyr   Leu   Gly   Ser   Asn   Arg   Ala   Ser   Gly   Val   Pro   Asp   Arg   Phe   Ser
                  50                              55                              60

Gly   Ser   Gly   Ser   Gly   Thr   Asp   Phe   Thr   Leu   Lys   Ile   Ser   Arg   Val   Glu
            65                      70                              75                              80

Ala   Glu   Asp   Val   Gly   Val   Tyr   Tyr   Cys   Met   Gln   Ala   Leu   Gln   Xaa   Pro
                                    85                          90                              95

Xaa   Thr   Phe   Gly   Gln   Gly   Thr   Lys   Xaa   Glu   Ile   Lys
                              100                       105
```

( 2 ) INFORMATION FOR SEQ ID NO:16:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
            Xaa   Ser   Val   Leu   Thr   Gln   Pro   Pro   Ser   Ala   Ser   Gly   Thr   Pro   Gly   Gln
            1                       5                           10                              15

Arg   Val   Thr   Ile   Ser   Cys   Ser   Gly   Ser   Ser   Ile   Gly   Xaa   Asn   Xaa
                                    20                          25                              30

Val   Xaa   Trp   Tyr   Gln   Gln   Leu   Pro   Gly   Thr   Ala   Pro   Asp   Leu   Leu   Ile
                              35                          40                              45

Tyr   Asn   Asn   Arg   Pro   Ser   Gly   Val   Pro   Asp   Arg   Phe   Ser   Gly   Ser   Lys
                  50                              55                              60

Ser   Gly   Thr   Ser   Ala   Ser   Leu   Ala   Ile   Ser   Gly   Leu   Gln   Ser   Glu   Asp
            65                      70                              75                              80

Glu   Ala   Asp   Tyr   Tyr   Cys   Ala   Thr   Trp   Asp   Asp   Ser   Leu   Asp   Pro   Val
                                    85                          90                              95

Phe   Gly   Gly   Gly   Thr   Lys   Thr   Val   Leu   Gly
                              100                       105
```

( 2 ) INFORMATION FOR SEQ ID NO:17:

( i ) SEQUENCE CHARACTERISTICS:

(A) LENGTH: 104 amino acids
(B) TYPE: amino acid
(D) TOPOLOGY: linear (i i) MOLECULE TYPE: protein (x i) SEQUENCE DESCRIPTION: SEQ ID NO:17:

| Xaa | Ser | Ala | Leu | Thr | Gln | Pro | Ala | Ser | Val | Ser | Gly | Ser | Pro | Gly | Gln |
|---|---|---|---|---|---|---|---|---|---|---|---|---|---|---|---|
| 1 | | | | 5 | | | | | 10 | | | | | 15 | |

| Ser | Ile | Thr | Ile | Ser | Cys | Thr | Gly | Thr | Ser | Ser | Val | Gly | Tyr | Asn | Xaa |
|---|---|---|---|---|---|---|---|---|---|---|---|---|---|---|---|
| | | | 20 | | | | | 25 | | | | | 30 | | |

| Val | Ser | Trp | Tyr | Gln | Gln | His | Pro | Gly | Lys | Ala | Pro | Lys | Leu | Ile | Tyr |
|---|---|---|---|---|---|---|---|---|---|---|---|---|---|---|---|
| | | | 35 | | | | 40 | | | | 45 | | | | |

| Asp | Val | Arg | Pro | Ser | Gly | Val | Arg | Phe | Ser | Gly | Ser | Lys | Ser | Gly | Asn |
|---|---|---|---|---|---|---|---|---|---|---|---|---|---|---|---|
| | 50 | | | | | 55 | | | | | 60 | | | | |

| Thr | Ala | Ser | Leu | Thr | Ile | Ser | Gly | Leu | Gln | Ala | Glu | Asp | Glu | Ala | Asp |
|---|---|---|---|---|---|---|---|---|---|---|---|---|---|---|---|
| 65 | | | | | 70 | | | | | 75 | | | | | 80 |

| Tyr | Tyr | Cys | Ser | Ser | Tyr | Xaa | Gly | Xaa | Xaa | Xaa | Xaa | Val | Phe | Gly | Gly |
|---|---|---|---|---|---|---|---|---|---|---|---|---|---|---|---|
| | | | | 85 | | | | | 90 | | | | | 95 | |

| Gly | Thr | Lys | Leu | Thr | Val | Leu | Gly |
|---|---|---|---|---|---|---|---|
| | | | 100 | | | | |

(2) INFORMATION FOR SEQ ID NO:18:

(i) SEQUENCE CHARACTERISTICS:
(A) LENGTH: 100 amino acids
(B) TYPE: amino acid
(D) TOPOLOGY: linear (i i) MOLECULE TYPE: protein (x i) SEQUENCE DESCRIPTION: SEQ ID NO:18:

| Ser | Tyr | Glu | Leu | Thr | Gln | Pro | Pro | Ser | Val | Ser | Val | Ser | Pro | Gly | Gln |
|---|---|---|---|---|---|---|---|---|---|---|---|---|---|---|---|
| 1 | | | | 5 | | | | | 10 | | | | | 15 | |

| Thr | Ala | Ile | Thr | Cys | Ser | Gly | Asp | Xaa | Leu | Xaa | Xaa | Xaa | Tyr | Val | Xaa |
|---|---|---|---|---|---|---|---|---|---|---|---|---|---|---|---|
| | | | 20 | | | | | 25 | | | | | 30 | | |

| Trp | Tyr | Gln | Gln | Lys | Pro | Gly | Gln | Ala | Pro | Val | Leu | Val | Ile | Tyr | Asp |
|---|---|---|---|---|---|---|---|---|---|---|---|---|---|---|---|
| | | | 35 | | | | 40 | | | | 45 | | | | |

| Arg | Pro | Ser | Gly | Ile | Pro | Gln | Arg | Phe | Ser | Gly | Ser | Ser | Thr | Thr | Ala |
|---|---|---|---|---|---|---|---|---|---|---|---|---|---|---|---|
| | 50 | | | | | 55 | | | | | 60 | | | | |

| Thr | Leu | Thr | Ile | Ser | Gly | Val | Gln | Ala | Asp | Glu | Ala | Asp | Tyr | Tyr | Cys |
|---|---|---|---|---|---|---|---|---|---|---|---|---|---|---|---|
| 65 | | | | | 70 | | | | | 75 | | | | | 80 |

| Gln | Xaa | Trp | Asp | Xaa | Xaa | Xaa | Val | Val | Phe | Gly | Gly | Gly | Thr | Lys | Leu |
|---|---|---|---|---|---|---|---|---|---|---|---|---|---|---|---|
| | | | | 85 | | | | | 90 | | | | | 95 | |

| Thr | Val | Leu | Gly |
|---|---|---|---|
| | | | 100 |

(2) INFORMATION FOR SEQ ID NO:19:

(i) SEQUENCE CHARACTERISTICS:
(A) LENGTH: 106 amino acids
(B) TYPE: amino acid
(D) TOPOLOGY: linear (i i) MOLECULE TYPE: protein (x i) SEQUENCE DESCRIPTION: SEQ ID NO:19:

| Asn | Phe | Met | Leu | Thr | Gln | Pro | His | Ser | Val | Ser | Glu | Ser | Pro | Gly | Lys |
|---|---|---|---|---|---|---|---|---|---|---|---|---|---|---|---|
| 1 | | | | 5 | | | | | 10 | | | | | 15 | |

| Thr | Val | Thr | Ile | Ser | Cys | Thr | Xaa | Ser | Xaa | Gly | Ile | Ala | Ser | Xaa | Tyr |
|---|---|---|---|---|---|---|---|---|---|---|---|---|---|---|---|
| | | | 20 | | | | | 25 | | | | | 30 | | |

```
Val Gln Trp Tyr Gln Gln Arg Pro Gly Ser Ala Pro Thr Thr Val Ile
         35                  40                  45

Tyr Glu Asp Asn Arg Pro Ser Gly Val Pro Asp Arg Phe Ser Gly Ser
         50                  55                  60

Ser Ser Asn Ser Ala Ser Leu Thr Ile Ser Gly Leu Lys Thr Glu Asp
 65                  70                  75                  80

Glu Ala Asp Tyr Tyr Cys Gln Ser Tyr Asp Ser Xaa Xaa Trp Val Phe
                 85                  90                  95

Gly Gly Gly Thr Lys Leu Thr Val Leu Gly
            100                 105
```

( 2 ) INFORMATION FOR SEQ ID NO:20:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Lys Asn
         20                  25                  30

Tyr Leu Ala Trp Tyr Gln Gln Lys Pro Gly Gln Pro Pro Lys Leu Leu
         35                  40                  45

Ile Tyr Trp Ala Ser Arg Glu Ser Gly Val Pro Asp Arg Phe Ser Gly
         50                  55                  60

Ser Gly Ser Gly Thr Asp Phe Thr Leu Thr Ile Ser Ser Leu Gln Ala
 65                  70                  75                  80

Gln Asp Val Ala Val Tyr Tyr Cys Gln Gln Tyr Tyr Ser Thr Pro Xaa
                 85                  90                  95

Thr Phe Gly Gly Gly Thr Lys Xaa Gly Ile Lys
            100                 105
```

( 2 ) INFORMATION FOR SEQ ID NO:21:

( i ) SEQUENCE CHARACTERISTICS:
        ( A ) LENGTH: 105 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Ser Glu Leu Thr Gln Pro Pro Ser Val Ser Val Ala Pro Gly Gln Thr
 1               5                  10                  15

Arg Ile Thr Cys Ser Gly Asp Xaa Leu Gly Xaa Tyr Asp Xaa Trp
         20                  25                  30

Tyr Gln Gln Lys Pro Gly Gln Ala Pro Leu Leu Val Ile Tyr Gly Arg
         35                  40                  45

Asn Arg Pro Ser Gly Ile Pro Asp Arg Phe Ser Gly Ser Ser Ser Gly
         50                  55                  60

His Thr Ala Ser Leu Thr Ile Thr Gly Ala Gln Ala Glu Asp Glu Ala
 65                  70                  75                  80

Asp Tyr Tyr Cys Asn Ser Arg Asp Ser Ser Gly Lys Val Leu Phe Gly
                 85                  90                  95

Gly Gly Thr Lys Leu Thr Val Leu Gly
            100                 105
```

( 2 ) INFORMATION FOR SEQ ID NO:22:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Ser Ala Leu Thr Gln Pro Pro Ser Ala Ser Gly Ser Pro Gly Gln Ser
 1               5                  10                  15
Val Thr Ile Ser Cys Thr Gly Thr Ser Ser Val Gly Xaa Xaa Tyr Val
            20                  25                  30
Ser Trp Tyr Gln Gln His Gly Ala Pro Lys Ile Glu Val Arg Pro Ser
        35                  40                  45
Gly Val Pro Asp Arg Phe Ser Gly Ser Lys Ser Asn Thr Ala Ser Leu
    50                  55                  60
Thr Val Ser Gly Leu Ala Glu Asp Glu Ala Asp Tyr Tyr Cys Ser Ser
65                  70                  75                  80
Tyr Xaa Xaa Xaa Xaa Xaa Phe Val Phe Gly Gly Thr Lys Thr Val Leu
                85                  90                  95
```

( 2 ) INFORMATION FOR SEQ ID NO:23:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Xaa Xaa
            20                  25                  30
Xaa Met Xaa Trp Val Arg Gln Ala Pro Gly Lys Gly Leu Glu Trp Val
        35                  40                  45
Xaa Xaa Ile Xaa Xaa Lys Xaa Xaa Gly Xaa Xaa Tyr Ala Asp Ser Val
    50                  55                  60
Lys Gly Arg Phe Thr Ile Ser Arg Asp Asp Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Xaa Xaa Xaa Xaa Xaa Xaa Xaa Xaa Xaa Trp Gly Gln Gly Thr
                100                 105                 110
Leu Val Thr Val Ser Ser
            115
```

( 2 ) INFORMATION FOR SEQ ID NO:24:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Gln Val Gln Leu Val Gln Ser Gly Ala Glu Val Lys Lys Pro Gly Xaa
```

```
  1                     5                           10                          15
  Ser  Val  Xaa  Val  Ser  Cys  Lys  Xaa  Ser  Gly  Tyr  Tyr  Phe  Xaa  Xaa  Tyr
                 20                       25                           30

Xaa  Ile  Xaa  Trp  Val  Arg  Gln  Ala  Pro  Gly  Xaa  Gly  Leu  Glu  Trp  Val
            35                       40                           45

Gly  Xaa  Ile  Xaa  Pro  Xaa  Xaa  Gly  Xaa  Thr  Xaa  Tyr  Ala  Pro  Xaa  Phe
       50                      55                           60

Gln  Gly  Arg  Val  Thr  Xaa  Thr  Arg  Asp  Xaa  Ser  Xaa  Asn  Thr  Ala  Tyr
  65                      70                      75                           80

Met  Glu  Leu  Xaa  Ser  Leu  Arg  Ser  Glu  Asp  Thr  Ala  Val  Tyr  Tyr  Cys
                 85                           90                           95

Ala  Arg  Xaa  Xaa  Xaa  Xaa  Xaa  Xaa  Xaa  Xaa  Xaa  Trp  Gly  Gln  Gly
                 100                      105                      110

Thr  Leu  Val  Thr  Val  Ser  Ser
                 115
```

( 2 ) INFORMATION FOR SEQ ID NO:25:

( i ) SEQUENCE CHARACTERISTICS:
        ( A ) LENGTH: 117 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
  Xaa  Val  Thr  Leu  Xaa  Glu  Ser  Gly  Pro  Xaa  Leu  Val  Leu  Pro  Thr  Gln
  1                   5                        10                          15

Thr  Leu  Thr  Leu  Thr  Cys  Thr  Val  Ser  Gly  Xaa  Ser  Leu  Ser  Xaa  Xaa
                 20                       25                           30

Xaa  Val  Xaa  Trp  Ile  Arg  Gln  Pro  Pro  Gly  Lys  Xaa  Leu  Glu  Trp  Leu
            35                       40                           45

Ala  Xaa  Ile  Xaa  Ile  Asp  Asp  Xaa  Tyr  Xaa  Thr  Ser  Leu  Arg  Ser
       50                      55                      60

Arg  Leu  Thr  Ile  Ser  Lys  Asp  Thr  Ser  Lys  Asn  Gln  Val  Val  Leu  Xaa
  65                      70                      75                           80

Xaa  Xaa  Xaa  Xaa  Asp  Pro  Xaa  Asp  Thr  Ala  Thr  Tyr  Tyr  Cys  Ala  Arg
                 85                           90                           95

Xaa  Xaa  Xaa  Xaa  Xaa  Xaa  Xaa  Xaa  Asp  Val  Trp  Gly  Gln  Gly  Thr  Thr
                 100                      105                      110

Val  Thr  Val  Ser  Ser
                 115
```

( 2 ) INFORMATION FOR SEQ ID NO:26:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
  Asp  Ile  Lys  Met  Thr  Gln  Ser  Pro  Ser  Ser  Met  Tyr  Ala  Ser  Leu  Gly
  1                   5                        10                          15

Glu  Arg  Val  Thr  Ile  Thr  Cys  Lys  Ala  Ser  Gln  Asp  Ile  Asn  Ser  Tyr
                 20                       25                           30

Leu  Ser  Trp  Phe  Gln  Gln  Lys  Pro  Gly  Lys  Ser  Pro  Lys  Thr  Leu  Ile
            35                       40                           45
```

Tyr Arg Ala Asn Arg Leu Val Asp Gly Val Pro Ser Arg Phe Ser Gly
            50                  55                  60

Ser Gly Ser Gly Gln Asp Tyr Ser Leu Thr Ile Ser Ser Leu Asp Tyr
        65                  70                  75                  80

Glu Asp Met Gly Ile Tyr Tyr Cys Gln Gln Tyr Asp Glu Ser Pro Trp
                            85                  90                  95

Thr Phe Gly Gly Gly Thr Lys Leu Glu Ile Lys
                        100                 105

( 2 ) INFORMATION FOR SEQ ID NO:27:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

Asp Ile Gln Met Thr Gln Ser Pro Ser Ser Met Ser Ala Ser Leu Gly
        1               5                   10                  15

Asp Arg Val Thr Ile Thr Cys Arg Ala Ser Gln Asp Ile Asn Ser Tyr
                        20                  25                  30

Leu Ser Trp Phe Gln Gln Lys Pro Gly Lys Ser Pro Lys Thr Leu Ile
                    35                  40                  45

Tyr Arg Ala Asn Arg Leu Val Asp Gly Val Pro Ser Arg Phe Ser Gly
            50                  55                  60

Ser Gly Ser Gly Thr Asp Tyr Thr Leu Thr Ile Ser Ser Leu Gln Tyr
        65                  70                  75                  80

Glu Asp Phe Gly Ile Tyr Tyr Cys Gln Gln Tyr Asp Glu Ser Pro Trp
                            85                  90                  95

Thr Phe Gly Gly Gly Thr Lys Leu Glu Ile Lys
                        100                 105

( 2 ) INFORMATION FOR SEQ ID NO:28:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

Gln Ile Gln Leu Val Gln Ser Gly Pro Glu Leu Lys Lys Pro Gly Glu
        1               5                   10                  15

Thr Val Lys Ile Ser Cys Lys Ala Ser Gly Tyr Thr Phe Thr Asn Tyr
                        20                  25                  30

Gly Met Asn Trp Val Lys Gln Ala Pro Gly Lys Gly Leu Arg Trp Met
                    35                  40                  45

Gly Trp Ile Asn Thr His Thr Gly Glu Pro Thr Tyr Ala Asp Asp Phe
            50                  55                  60

Lys Gly Arg Phe Ala Phe Ser Leu Glu Thr Ser Ala Ser Thr Ala Tyr
        65                  70                  75                  80

Leu Gln Ile Asn Asn Leu Lys Asn Glu Asp Thr Ala Thr Tyr Phe Cys
                            85                  90                  95

Thr Arg Arg Gly Tyr Asp Trp Tyr Phe Asp Val Trp Gly Ala Gly Thr
                        100                 105                 110

Thr Val Thr Val Ser Ser
                    115

( 2 ) INFORMATION FOR SEQ ID NO:29:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Gln Ile Gln Leu Val Gln Ser Gly Pro Gly Leu Lys Lys Pro Gly Gly
 1               5                  10                      15
Ser Val Arg Ile Ser Cys Ala Ala Ser Gly Tyr Thr Phe Thr Asn Tyr
            20                  25                  30
Gly Met Asn Trp Val Lys Gln Ala Pro Gly Lys Gly Leu Arg Trp Met
        35                  40                  45
Gly Trp Ile Asn Thr His Thr Gly Glu Pro Thr Tyr Ala Asp Asp Phe
    50                  55                  60
Lys Gly Arg Phe Thr Phe Ser Leu Asp Thr Ser Lys Ser Thr Ala Tyr
65                  70                  75                  80
Leu Gln Ile Asn Ser Leu Arg Ala Glu Asp Thr Ala Thr Tyr Phe Cys
                85                  90                  95
Thr Arg Arg Gly Tyr Asp Trp Tyr Phe Asp Val Trp Gly Gln Gly Thr
                100                 105                 110
Thr Val Thr Val Ser Ser
            115
```

( 2 ) INFORMATION FOR SEQ ID NO:30:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

```
AGTCGTCGAC ACGATGGACA TGAGGACCCC TGCTCAGTTT CTTGGCATCC TCCTACTCTG    60
GTTTCCAGGT ATCAAATGTG ACATCCAGAT GACTCAGT                            98
```

( 2 ) INFORMATION FOR SEQ ID NO:31:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

```
TGACTCGCCC GGCAAGTGAT AGTGACTCTG TCTCCCAGAC ATGCAGACAT GGAAGATGAG    60
GACTGAGTCA TCTGGATGTC                                                80
```

( 2 ) INFORMATION FOR SEQ ID NO:32:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear (ii) MOLECULE TYPE: DNA (xi) SEQUENCE DESCRIPTION: SEQ ID NO:32:

TCACTTGCCG GGCGAGTCAG GACATTAATA GCTATTTAAG CTGGTTCCAG CAGAAACCAG    60

GGAAATCTCC TAAGACCCT    79

(2) INFORMATION FOR SEQ ID NO:33:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

GATCCACTGC CACTGAACCT TGATGGGACC CCATCTACCA ATCTGTTTGC ACGATAGATC    60

AGGGTCTTAG GAGATTTCC    79

(2) INFORMATION FOR SEQ ID NO:34:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

GGTTCAGTGG CAGTGGATCT GGGACAGATT ATACTCTCAC CATCAGCAGC CTGCAATATG    60

AAGATTTTGG AATTTATTAT TG    82

(2) INFORMATION FOR SEQ ID NO:35:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

GTTTGATTTC AAGCTTGGTG CCTCCACCGA ACGTCCACGG AGACTCATCA TACTGTTGAC    60

AATAATAAAT TCCAAAATCT TC    82

(2) INFORMATION FOR SEQ ID NO:36:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

TGTCGACATC ATGGCTTGGG TGTGGACCTT GCTATTCCTG ATGGCAGCTG CCCAAAGTGC    60

CCAAGCACAG ATCCAGTTGG TGCAG    85

(2) INFORMATION FOR SEQ ID NO:37:

(i) SEQUENCE CHARACTERISTICS:

-continued (A) LENGTH: 85 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:37:

AAGGTATACC CAGAAGCTGC GCAGGAGATT CTGACGGACC CTCCAGGCTT CTTCAGGCCA  60

GGTCCAGACT GCACCAACTG GATCT  85

(2) INFORMATION FOR SEQ ID NO:38:

(i) SEQUENCE CHARACTERISTICS:
(A) LENGTH: 84 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:38:

GCAGCTTCTG GGTATACCTT CACAAACTAT GGAATGAACT GGGTGAAGCA GGCTCCAGGA  60

AAGGGTTTAA GGTGGATGGG CTGG  84

(2) INFORMATION FOR SEQ ID NO:39:

(i) SEQUENCE CHARACTERISTICS:
(A) LENGTH: 85 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:39:

AAAGAGAAGG TAAACCGTCC CTTGAAGTCA TCAGCATATG TTGGCTCTCC AGTGTGGGTG  60

TTTATCCAGC CCATCCACCT TAAAC  85

(2) INFORMATION FOR SEQ ID NO:40:

(i) SEQUENCE CHARACTERISTICS:
(A) LENGTH: 84 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:40:

GACGGTTTAC CTTCTCTTTG GACACGTCTA AGTGCACTGC CTATTTACAG ATCAACAGCC  60

TCAGAGCCGA GGACACGGCT ACAT  84

(2) INFORMATION FOR SEQ ID NO:41:

(i) SEQUENCE CHARACTERISTICS:
(A) LENGTH: 91 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:41:

AGGAGACGGT GACCGTGGTC CCTTGGCCCC AGACATCGAA GTACCAGTCG TAACCCCGTC  60

TTGTACAGAA ATATGTAGCC GTGTCCTCGG C  91

( 2 ) INFORMATION FOR SEQ ID NO:42:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:42:

ACTAGTGTCG ACATCATGGC TTGGGT                                                                           26

( 2 ) INFORMATION FOR SEQ ID NO:43:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:43:

GAGGAGACGG TGACCGTGGT                                                                                   20

( 2 ) INFORMATION FOR SEQ ID NO:44:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:44:

AGTCGTCGAC ACGATGGACA TGAGGAC                                                                          27

( 2 ) INFORMATION FOR SEQ ID NO:45:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:45:

GTTTGATTTC AAGCTTGGTG C                                                                                 21

( 2 ) INFORMATION FOR SEQ ID NO:46:

( i ) SEQUENCE CHARACTERISTICS:
      ( A ) LENGTH: 425 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:46:

ACTAGTGTCG ACATCATGGC TTGGGTGTGG ACCTTGCTAT TCCTGATGGC AGCTGCCCAA      60

AGTGCCCAAG CACAGATCCA GTTGGTGCAG TCTGGACCTG GCCTGAAGAA GCCTGGAGGG    120

TCCGTCAGAA TCTCCTGCGC AGCTTCTGGG TATACCTTCA CAAACTATGG AATGAACTGG    180

```
GTGAAGCAGG CTCCAGGAAA GGGTTTAAGG TGGATGGGCT GGATAAACAC CCACACTGGA      240

GAGCCAACAT ATGCTGATGA CTTCAAGGGA CGGTTTACCT TCTCTTTGGA CACGTCTAAG      300

AGCACTGCCT ATTACAGAT  CAACAGCCTC AGAGCCGAGG ACACGGCTAC ATATTTCTGT      360

ACAAGACGGG GTTACGACTG GTACTTCGAT GTCTGGGGCC AAGGGACCAC GGTCACCGTC      420

TCCTC                                                                   425
```

( 2 ) INFORMATION FOR SEQ ID NO:47:

( i ) SEQUENCE CHARACTERISTICS:
        ( A ) LENGTH: 401 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

```
AGTCGTCGAC ACGATGGACA TGAGGACCCC TGCTCAGTTT CTTGGCATCC TCCTACTCTG       60

GTTTCCAGGT ATCAAATGTG ACATCCAGAT GACTCAGTCT CCATCTTCCA TGTCTGCATC      120

TCTGGGAGAC AGAGTCACTA TCACTTGCCG GGCGAGTCAG GACATTAATA GCTATTTAAG      180

CTGGTTCCAG CAGAAACCAG GGAAATCTCC TAAGACCCTG ATCTATCGTG CAAACAGATT      240

GGTAGATGGG GTCCCATCAA GGTTCAGTGG CAGTGGATCT GGGACAGATT ATACTCTCAC      300

CATCAGCAGC CTGCAATATG AAGATTTTGG AATTTATTAT TGTCAACAGT ATGATGAGTC      360

TCCGTGGACG TTCGGTGGAG GCACCAAGCT TGAAATCAAA C                         401
```

( 2 ) INFORMATION FOR SEQ ID NO:48:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:48:

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Asn Thr Trp
            20                  25                  30

Leu Ala Trp Tyr Gln Gln Lys Pro Gly Lys Ala Pro Lys Leu Leu Met
        35                  40                  45

Tyr Lys Ala Ser Ser Leu Glu Ser Gly Val Pro Ser Arg Phe Ile Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Asp Ser Lys
                85                  90                  95

Met Phe Gly Gln Gly Thr Lys Val Glu Val Lys
                100                 105
```

( 2 ) INFORMATION FOR SEQ ID NO:49:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:49:

| Gln | Ile | Val | Leu | Thr | Gln | Ser | Pro | Ala | Ile | Met | Ser | Ala | Ser | Pro | Gly |
| 1 | | | | 5 | | | | | 10 | | | | | 15 | |

| Glu | Lys | Val | Thr | Ile | Thr | Cys | Ser | Ala | Ser | Ser | Ser | Ile | Ser | Tyr | Met |
| | | | 20 | | | | | 25 | | | | | 30 | | |

| His | Trp | Phe | Gln | Gln | Lys | Pro | Gly | Thr | Ser | Pro | Lys | Leu | Trp | Ile | Tyr |
| | | 35 | | | | | 40 | | | | | 45 | | | |

| Thr | Thr | Ser | Asn | Leu | Ala | Ser | Gly | Val | Pro | Ala | Arg | Phe | Ser | Gly | Ser |
| | 50 | | | | | 55 | | | | | 60 | | | | |

| Gly | Ser | Gly | Thr | Ser | Tyr | Ser | Leu | Thr | Ile | Ser | Arg | Met | Glu | Ala | Glu |
| 65 | | | | | 70 | | | | | 75 | | | | | 80 |

| Asp | Ala | Ala | Thr | Tyr | Tyr | Cys | His | Gln | Arg | Ser | Thr | Tyr | Pro | Leu | Thr |
| | | | | 85 | | | | | 90 | | | | | 95 | |

| Phe | Gly | Ser | Gly | Thr | Lys | Leu | Glu | Leu | Lys | | | | | | |
| | | | 100 | | | | | 105 | | | | | | | |

( 2 ) INFORMATION FOR SEQ ID NO:50:

( i ) SEQUENCE CHARACTERISTICS:
    ( A ) LENGTH: 106 amino acids
    ( B ) TYPE: amino acid
    ( D ) TOPOLOGY: linear ( i i ) MOLECULE TYPE: protein ( x i ) SEQUENCE DESCRIPTION: SEQ ID NO:50:

| Asp | Ile | Gln | Leu | Thr | Gln | Ser | Pro | Ser | Ser | Met | Ser | Ala | Ser | Pro | Gly |
| 1 | | | | 5 | | | | | 10 | | | | | 15 | |

| Asp | Arg | Val | Thr | Ile | Thr | Cys | Arg | Ala | Ser | Ser | Ser | Ile | Ser | Tyr | Met |
| | | | 20 | | | | | 25 | | | | | 30 | | |

| His | Trp | Phe | Gln | Gln | Lys | Pro | Gly | Lys | Ser | Pro | Lys | Leu | Trp | Ile | Tyr |
| | | 35 | | | | | 40 | | | | | 45 | | | |

| Thr | Thr | Ser | Asn | Leu | Ala | Ser | Gly | Val | Pro | Ser | Arg | Phe | Ser | Gly | Ser |
| | 50 | | | | | 55 | | | | | 60 | | | | |

| Gly | Ser | Gly | Thr | Ser | Tyr | Thr | Leu | Thr | Ile | Ser | Ser | Met | Gln | Ala | Glu |
| 65 | | | | | 70 | | | | | 75 | | | | | 80 |

| Asp | Phe | Ala | Thr | Tyr | Tyr | Cys | His | Gln | Arg | Ser | Thr | Tyr | Pro | Leu | Thr |
| | | | | 85 | | | | | 90 | | | | | 95 | |

| Phe | Gly | Gln | Gly | Thr | Lys | Leu | Glu | Leu | Lys | | | | | | |
| | | | 100 | | | | | 105 | | | | | | | |

( 2 ) INFORMATION FOR SEQ ID NO:51:

( i ) SEQUENCE CHARACTERISTICS:
    ( A ) LENGTH: 106 amino acids
    ( B ) TYPE: amino acid
    ( D ) TOPOLOGY: linear ( i i ) MOLECULE TYPE: protein ( x i ) SEQUENCE DESCRIPTION: SEQ ID NO:51:

| Asp | Ile | Gln | Met | Thr | Gln | Ser | Pro | Ser | Thr | Leu | Ser | Ala | Ser | Val | Gly |
| 1 | | | | 5 | | | | | 10 | | | | | 15 | |

| Asp | Arg | Val | Thr | Ile | Thr | Cys | Ser | Ala | Ser | Ser | Ser | Ile | Ser | Tyr | Met |
| | | | 20 | | | | | 25 | | | | | 30 | | |

| His | Trp | Tyr | Gln | Gln | Lys | Pro | Gly | Lys | Ala | Pro | Lys | Leu | Leu | Ile | Tyr |
| | | 35 | | | | | 40 | | | | | 45 | | | |

| Thr | Thr | Ser | Asn | Leu | Ala | Ser | Gly | Val | Pro | Ala | Arg | Phe | Ser | Gly | Ser |
| | 50 | | | | | 55 | | | | | 60 | | | | |

```
Gly Ser Gly Thr Glu Phe Thr Leu Thr Ile Ser Ser Leu Gln Pro Asp
 65              70                  75                      80

Asp Phe Ala Thr Tyr Tyr Cys His Gln Arg Ser Thr Tyr Pro Leu Thr
                 85              90                  95

Phe Gly Gln Gly Thr Lys Val Glu Val Lys
                100             105
```

( 2 ) INFORMATION FOR SEQ ID NO:52:

( i ) SEQUENCE CHARACTERISTICS:
           ( A ) LENGTH: 117 amino acids
           ( B ) TYPE: amino acid
           ( D ) TOPOLOGY: linear ( i i ) MOLECULE TYPE: protein ( x i ) SEQUENCE DESCRIPTION: SEQ ID NO:52:

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Arg Ser
                 20                  25                  30

Ala Ile Ile Trp Val Arg Gln Ala Pro Gly Gln Gly Leu Glu Trp Met
             35                  40                  45

Gly Gly Ile Val Pro Met Phe Gly Pro Pro Asn Tyr Ala Gln Lys Phe
         50                  55                  60

Gln Gly Arg Val Thr Ile Thr Ala Asp Glu Ser Thr Asn Thr Ala Tyr
 65              70                  75                      80

Met Glu Leu Ser Ser Leu Arg Ser Glu Asp Thr Ala Phe Tyr Phe Cys
                 85                  90                  95

Ala Gly Gly Tyr Gly Ile Tyr Ser Pro Glu Glu Tyr Asn Gly Gly Leu
                100             105                 110

Val Thr Val Ser Ser
             115
```

( 2 ) INFORMATION FOR SEQ ID NO:53:

( i ) SEQUENCE CHARACTERISTICS:
           ( A ) LENGTH: 116 amino acids
           ( B ) TYPE: amino acid
           ( D ) TOPOLOGY: linear ( i i ) MOLECULE TYPE: protein ( x i ) SEQUENCE DESCRIPTION: SEQ ID NO:53:

```
Gln Val Gln Leu Gln Gln Ser Gly Ala Glu Leu Ala Lys Pro Gly Ala
 1               5                  10                  15

Ser Val Lys Met Ser Cys Lys Ala Ser Gly Tyr Thr Phe Thr Ser Tyr
                 20                  25                  30

Arg Met His Trp Val Lys Gln Arg Pro Gly Gln Gly Leu Glu Trp Ile
             35                  40                  45

Gly Tyr Ile Asn Pro Ser Thr Gly Tyr Thr Glu Tyr Asn Gln Lys Phe
         50                  55                  60

Lys Asp Lys Ala Thr Leu Thr Ala Asp Lys Ser Ser Ser Thr Ala Tyr
 65              70                  75                      80

Met Gln Leu Ser Ser Leu Thr Phe Glu Asp Ser Ala Val Tyr Tyr Cys
                 85                  90                  95

Ala Arg Gly Gly Gly Val Phe Asp Tyr Trp Gly Gln Gly Thr Thr Leu
                100             105                 110

Thr Val Ser Ser
         115
```

(2) INFORMATION FOR SEQ ID NO:54:

(i) SEQUENCE CHARACTERISTICS:
(A) LENGTH: 116 amino acids
(B) TYPE: amino acid
(D) TOPOLOGY: linear (ii) MOLECULE TYPE: protein (xi) SEQUENCE DESCRIPTION: SEQ ID NO:54:

| Gln | Val | Gln | Leu | Gln | Gln | Ser | Gly | Ala | Glu | Val | Ala | Lys | Pro | Gly | Ala |
|---|---|---|---|---|---|---|---|---|---|---|---|---|---|---|---|
| 1 | | | | 5 | | | | | 10 | | | | | 15 | |
| Ser | Val | Lys | Met | Ser | Cys | Lys | Ala | Ser | Gly | Tyr | Thr | Phe | Thr | Ser | Tyr |
| | | | 20 | | | | | 25 | | | | | 30 | | |
| Arg | Met | His | Trp | Val | Lys | Gln | Ala | Pro | Gly | Gln | Gly | Leu | Glu | Trp | Ile |
| | | 35 | | | | | 40 | | | | | 45 | | | |
| Gly | Tyr | Ile | Asn | Pro | Ser | Thr | Gly | Tyr | Thr | Glu | Tyr | Asn | Gln | Lys | Phe |
| | 50 | | | | | 55 | | | | | 60 | | | | |
| Lys | Gly | Lys | Ala | Thr | Leu | Thr | Ala | Asp | Lys | Ser | Ser | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Gly | Gly | Gly | Val | Phe | Asp | Tyr | Trp | Gly | Gln | Gly | Thr | Thr | Leu |
| | | | 100 | | | | | 105 | | | | | 110 | | |
| Thr | Val | Ser | Ser | | | | | | | | | | | | |
| | | 115 | | | | | | | | | | | | | |

(2) INFORMATION FOR SEQ ID NO:55:

(i) SEQUENCE CHARACTERISTICS:
(A) LENGTH: 116 amino acids
(B) TYPE: amino acid
(D) TOPOLOGY: linear (ii) MOLECULE TYPE: protein (xi) SEQUENCE DESCRIPTION: SEQ ID NO:55:

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Arg | Met | His | Trp | Val | Arg | Gln | Ala | Pro | Gly | Gln | Gly | Leu | Glu | Trp | Ile |
| | | 35 | | | | | 40 | | | | | 45 | | | |
| Gly | Tyr | Ile | Asn | Pro | Ser | Thr | Gly | Tyr | Thr | Glu | Tyr | Asn | Gln | Lys | Phe |
| | 50 | | | | | 55 | | | | | 60 | | | | |
| Lys | Asp | Lys | Ala | Thr | Ile | Thr | Ala | Asp | Glu | Ser | Thr | Asn | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Gly | Gly | Gly | Val | Phe | Asp | Tyr | Trp | Gly | Gln | Gly | Thr | Leu | Val |
| | | | 100 | | | | | 105 | | | | | 110 | | |
| Thr | Val | Ser | Ser | | | | | | | | | | | | |
| | | 115 | | | | | | | | | | | | | |

(2) INFORMATION FOR SEQ ID NO:56:

(i) SEQUENCE CHARACTERISTICS:
(A) LENGTH: 85 base pairs
(B) TYPE: nucleic acid
(C) STRANDEDNESS: single ( D ) TOPOLOGY: linear ( i i ) MOLECULE TYPE: DNA ( x i ) SEQUENCE DESCRIPTION: SEQ ID NO:56:

TGTCGACATC ATGGCTTGGG TGTGGACCTT GCTATTCCTG ATGGCAGCTG CCCAAAGTGC    60

CCAAGCAGAG ATCCAGTTGG TGCAG    85

( 2 ) INFORMATION FOR SEQ ID NO:57:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

AAGGTATACC CAGAAGCTGC GCAGGAGATT CTGACGGACC CTCCAGGCTT CACCAGGCCT    60

CCTCCAGACT GCACCAACTG GATCTC    86

( 2 ) INFORMATION FOR SEQ ID NO:58:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

GCAGCTTCTG GGTATACCTT CACAAACTAT GGAATGAACT GGGTGCGCCA GGCTCCAGGA    60

AAGAATTTAG AGTGGATGGG CTGG    84

( 2 ) INFORMATION FOR SEQ ID NO:59:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:59:

AAAGAGAAGG TAAACCGTCC CTTGAAAGAA TCAGCATATG TTGGCTCTCC AGTGTGGGTG    60

TTTATCCAGC CCATCCACTC TAAAC    85

( 2 ) INFORMATION FOR SEQ ID NO:60:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:60:

GACGGTTTAC CTTCTCTTTG GACGATTCTA AGAACACTGC CTATTTACAG ATCAACAGCC    60

TCAGAGCCGA GGACACGGCT GTGTATT    87

( 2 ) INFORMATION FOR SEQ ID NO:61:

( i ) SEQUENCE CHARACTERISTICS:
    ( A ) LENGTH: 92 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:61:

```
GAGGAGACGG TGACCGTGGT CCCTTGGCCC CAGACATCGA AGTACCAGTC GTAACCCCGT      60
CTTGTACAGA AATACACAGC CGTGTCCTCG GC                                    92
```

( 2 ) INFORMATION FOR SEQ ID NO:62:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:62:

```
TGACTCGCCC GGCAAGTGAT AGTGACTCTG TCTCCTACAG ATGCAGACAG GGAAGATGGA      60
GACTGAGTCA TCTGGATGTC                                                  80
```

( 2 ) INFORMATION FOR SEQ ID NO:63:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:63:

```
TCACTTGCCG GGCGAATCAG GACATTAATA GCTATTTAAG CTGGTTCCAG CAGAAACCAG      60
GGAAAGCTCC TAAGACCCT                                                   79
```

( 2 ) INFORMATION FOR SEQ ID NO:64:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:64:

```
GATCCACTGC CACTGAACCT TGATGGGACC CCAGATTCCA ATCTGTTTGC ACGATAGATC      60
AGGGTATTAG GAGCTTTCC                                                   79
```

( 2 ) INFORMATION FOR SEQ ID NO:65:

( i ) SEQUENCE CHARACTERISTICS:
    ( A ) LENGTH: 107 amino acids
    ( B ) TYPE: amino acid
    ( D ) TOPOLOGY: linear ( i i ) MOLECULE TYPE: protein ( x i ) SEQUENCE DESCRIPTION: SEQ ID NO:65:

```
Asp Ile Gln Met Thr Gln Ser Pro Ser Ser Leu Ser Ala Ser Val Gly
 1               5                  10                  15
```

```
Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Tyr
65                  70                  75                  80

Glu Asp Phe Gly Ile Tyr Tyr Cys Gln Gln Tyr Asp Glu Ser Pro Trp
                85                  90                  95

Thr Phe Gly Gly Gly Thr Lys Leu Glu Ile Lys
                100             105
```

( 2 ) INFORMATION FOR SEQ ID NO:66:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:66:

```
Gln Ile Gly Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Arg Trp Met
        35                  40                  45

Gly Trp Ile Asn Thr His Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Thr Arg Arg Gly Tyr Asp Trp Tyr Phe Asp Val Trp Gly Ala Gly Thr
                100             105                 110

Thr Val Thr Val Ser Ser
            115
```

( 2 ) INFORMATION FOR SEQ ID NO:67:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:67:

```
Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Thr Arg Thr Phe Ser Leu Asp Asp Ser Lys Asn Thr Ala Tyr
```

| 65 | | | | | 70 | | | | | 75 | | | | | 80 |
|---|---|---|---|---|---|---|---|---|---|---|---|---|---|---|---|
| Leu | Gln | Ile | Asn | Ser | Leu | Arg | Ala | Glu | Asp | Thr | Ala | Val | Tyr | Phe | Cys |
| | | | | 85 | | | | | 90 | | | | | 95 | |
| Thr | Arg | Arg | Gly | Tyr | Asp | Trp | Tyr | Phe | Asp | Val | Trp | Gly | Gln | Gly | Thr |
| | | | 100 | | | | | 105 | | | | | 110 | | |
| Thr | Val | Thr | Val | Ser | Ser | | | | | | | | | | |
| | | 115 | | | | | | | | | | | | | |